(12) United States Patent
Zhou et al.

(10) Patent No.: US 7,789,943 B2
(45) Date of Patent: Sep. 7, 2010

(54) MESH-ADJUSTABLE MOLECULAR SIEVE

(75) Inventors: Hong-Cai Zhou, Oxford, OH (US);
Shengqian Ma, Oxford, OH (US)

(73) Assignee: Miami University, Oxford, OH (US)

( * ) Notice: Subject to any disclaimer, the term of this patent is extended or adjusted under 35 U.S.C. 154(b) by 264 days.

(21) Appl. No.: 12/025,167

(22) Filed: Feb. 4, 2008

(65) Prior Publication Data

US 2008/0184881 A1    Aug. 7, 2008

Related U.S. Application Data

(60) Provisional application No. 60/899,115, filed on Feb. 2, 2007.

(51) Int. Cl.
*B01D 53/02* (2006.01)
*B01J 20/22* (2006.01)

(52) U.S. Cl. ............... 95/116; 95/143; 95/902; 556/1; 556/170; 502/401

(58) Field of Classification Search ............ 95/90, 95/116, 130, 143, 902; 96/108; 556/1, 27, 556/170; 502/401, 439, 526
See application file for complete search history.

(56) References Cited

U.S. PATENT DOCUMENTS

| 6,930,193 | B2 | 8/2005 | Yaghi et al. |
| 2004/0225134 | A1 | 11/2004 | Yaghi et al. |
| 2006/0057057 | A1 | 3/2006 | Muller et al. |
| 2006/0185388 | A1 | 8/2006 | Muller et al. |
| 2006/0210458 | A1 | 9/2006 | Mueller et al. |
| 2006/0252641 | A1 | 11/2006 | Yaghi et al. |
| 2008/0184883 | A1* | 8/2008 | Zhou et al. ............ 95/127 |

OTHER PUBLICATIONS

Ma, Shengqian et al.; A Mesh-Adjustable Molecular Sieve for General Use in Gas Separation; Angewandte Chemie, International Edition, journal; 2007; pp. 2458-2462; vol. 46.
Ma, Shengqian et al.; Preparation and Gas Adsorption Studies of Three Mesh-Adjustable Molecular Sieve with a Common Structure; J. Am. Chem. Soc. 2009, 131; pp. 6445-6451.
Long Pan et al; Porous Lanthanide-Organic Frameworks: Synthesis, Characterization, and Unprecedented Gas Adsorption Properties; JACS, Feb. 12, 2003; vol. 125, No. 10; 3062-2067.

(Continued)

*Primary Examiner*—Frank M Lawrence
(74) *Attorney, Agent, or Firm*—Jason H. Foster; Kremblas & Foster

(57) ABSTRACT

Temperature-adjustable pore size molecular sieves comprise a plurality of metal clusters bound with a plurality of amphiphilic ligands, each ligand comprising a functionalized hydrophobic moiety and a functionalized hydrophilic moiety, and wherein the metal clusters and amphiphilic ligand hydrophilic moieties form a metal cluster layer, the metal cluster layer forming at least one hydrophilic pore. On each side of the metal cluster layer, a plurality of associated amphiphilic ligand hydrophobic moieties cooperate with the metal cluster layer to form a tri-layer and a plurality of tri-layers are held in proximity with each other to form at least one hydrophobic chamber.

24 Claims, 40 Drawing Sheets

OTHER PUBLICATIONS

Long Pan et al; Zn(tbip) (H2tbip+5-tert-Butyl Isopthalic Acid): A Highly Stable Guest-Free Microporous Metal Organic Framework with Unique Gas Separation Capability; JACS, Mar. 14, 2006; vol. 128, No. 13; 4180-4181.

Jasra et al; Separation of Gases by Pressure Swing Adsorption; Separation Science and Technology; 1991; vol. 26; 885-930.

Yaghi, Omar et al; Reticular Synthesis and the Design of New Materials; Review Article; Jun. 12, 2003; vol. 423; 705-715; Nature Publishing Group.

Daofeng Sun et al; Construction of Open Metal-Organic Frameworks Based on Predesigned Carboxylate Isomers: From Achiral to Chiral Nets; Chem.Eur.J.; 12; 2006; 3768-3776.

Daofeng Sun et al; Temperature-Dependent Supramolecular Stereoisomerism in Porous Copper Coordination Networks Based on a Designed Carboxylate Ligand; Chem. Commun.; 2005; 5447-5449.

Susumu Kitagawa et al; Functional Porous Coordination Polymers; Review; 2004; Angew. Chem. Int. Ed.; 43; 2334-2375.

Susumu Kitagawa et al; Dynamic Porous Properties of Coordination Polymers Inspired by Hydrogen Bonds; Tutorial Review; 2005; Chem. Soc. Rev.; 109-119.

Daofeng Sun et al; An Interweaving MOF with High Hydrogen Uptake; J.Am.Chem.Soc.; 2006; 3896-3897.

Shengqian Ma et al; A Metal-Organic Framework with Entatic Metal Centers Exhibiting High Gas Adsorption Affinity; J.Am.Chem.Soc.; 2006; 11734-11735.

Daeho Ko et al; Optimization of a Pressure-Swing Adsorption Process Using Zeolite 13X for CO2 Sequestration; Ind. Eng. Chem. Res.; 42; 2003; 339-348.

Davis, Mark E.; Ordered Porous Materials for Emerging Applications; Nature; vol. 417; Jun. 20, 2002; 813-821.

Shivaji Sircar et al; Gas Separation by Zeolites; No. 22; p. 063.

Cheetham et al; Open-Framework Inorganic Materials; Angew. Chem. Int. Ed. 1999; 38; 3268-3292.

Kuznicki et al; A Titanosilicate Molecular Sieve with Adjustable Pores for Size-Selective Adsorption of Molecules; Nature; vol. 412; Aug. 16, 2001; 720-724.

Kazuhiro Uemura et al; Flexible Microporous Coordination Polymers; Journal of Solid State Chemistry; 178; 2005; 2420-2429.

Ockwig et al; Reticular Chemistry: Occurrence and Taxonomy of Nets and Grammar for the Design of Frameworks; Acc. Chem. Res.; 38; 2005; 176-182.

Stuart R. Batten; Glorious Uncertainty-Challenges for Network Design; Journal of Solid State Chemistry; 178; 2005; 2475-2479.

Jung Soo Seo et al; A Homochiral Metal-Organic Porous Material for Enantioselective Separation and Catalysis; Nature; vol. 404; Apr. 27, 2000; 982-986.

Ru-Qiang Zou et al; Preparation, Adsorption Properties, and Catalytic Activity of 3D Porous Metal-Organic Frameworks Composed of Cubic Building Blocks and Alkali-Metal Ions; Angew. Chem. Int. Ed.; 45; 2006; 2542-2546.

Danil N. Dybtsev et al; A Homochiral Metal-Organic Material with Permanent Porosity, Enantioselective Sorption Properties, and Catalytic Activity; Angew. Chem. Int. Ed.; 45; 2006; 916-920.

Ryotaro Matsuda et al; Highly Controlled Acetylene Accommodation in a Metal-Organic Microporous Material; Nature; vol. 436; Jul. 14, 2005; 238-241.

Mircea Dinca et al; Strong H2 Binding and Selective Gas Adsorption within the Microporous Coordination Solid Mg3 (02C-C10H6-CO2)3; J. Am. Chem. Soc.; 127; 2005; 9376-9377.

Danil N. Dybtsev et al; Microporous Manganese Formate: A Simple Metal-Organic Porous Material with High Framework Stability and Highly Selective Gas Sorption Properties; J. Am. Chem. Soc.; 126; 2004; 32-33.

Banglin Chen et al; A Microporous Metal-Organic Framework for Gas-Chromatographic Separation of Alkanes; Angew. Chem. Int. Ed.; 45; 2006; 1390-1393.

Long Pan et al; Separation of Hydrocarbons with a Microporous Metal-Organic Framework; Angew. Chem. Int. Ed.; 45; 2006; 616-619.

Banglin Chen et al; Rationally Designed Micropores within a Metal-Organic Framework for Selective Sorption of Gas Molecules; Inorganic Chemistry; vol. 46, No. 4; 2007; 1233-1236.

Rowsell et al; Strategies for Hydrogen Storage in Metal-Organic Frameworks; Angew. Chem. Int. Ed.; 44; 2005; 4670-4679.

Banglin Chen et al; High H2 Adsorption in a Microporous Metal-Organic Framework with Open Metal Sites; Angew. Chem. Int. Ed.; 44; 2005; 4745-4749.

Rowsell et al; Effects of Functionalization, Catenation, and Variation of the Metal Oxide and Organic Linking Units on the Low-Pressure Hydrogen Adsorption Properties of Metal-Organic Frameworks; J. Am. Chem. Soc.; 128; 2006; 1304-1315.

Mohamed Eddaoudi et al; Systematic Design of Pore Size and Functionality in Isoreticular MOFs and Their Application in Methane Storage; Science 295; 2002; 469.

Millward et al; Metal-Organic Frameworks with Exceptionally High Capacity for Storage of Carbon Dioxide at Room Temperature; J. Am. Chem. Soc.; 126; 2005; 17998-17999.

P. Sozzani et al; Methane and Carbon Dioxide Storage in a Porous van der Waals Crystal; Angew. Chem. Int. Ed.; 44; 2005; 1816-1820.

Atwood et al; Guest Transport in a Nonporous Organic Soilid via Dynamic van der Waals Cooperativity; Science 298; 1000; 2002.

Qisheng Huo et al; Generalized Synthesis of Periodic Surfactant/Inorganic Composite Materials; Nature; vol. 368; Mar. 24, 1994; 317-321.

Yanxiong Ke et al; Synthesis and Structure of Cuboctahedral and Anticuboctahedral Cages Containing 12 Quadruply Bonded Dimolybdenum Units; Inorganic Chemistry; vol. 44, No. 12; 2005; 4154-4156.

A. Bondi; van der Waals Volumes and Radii; The Journal of Physical Chemistry; vol. 68, No. 3; Mar. 16, 1964; 441-451.

Beck; Adsorption by Dehydrated Zeolite Crystals; Table 8.14—Table of Dimensions for Various Molecules (66); 636.

Omar M. Yaghi et al; Synthetic Strategies, Structure Patterns, and Emerging Properties in the Chemistry of Modular Porous Solids; Accounts of Chemical Research; vol. 31, No. 8; 1998; 474-484.

Moulton et al; From Molecules to Crystal Engineering: Supramolecular Isomerism and Polymorphism in Network Solids; Chem. Rev. 2001; 101; 1629-1658.

Banu Kesanli et al; Highly Interpenetrated Metal-Organic Frameworks for Hydrogen Storage; Angew. Chem. Int. Ed.; 44; 2005; 72-75.

Mircea Dinca et al; Hydrogen Storage in a Microporous Metal-Organic Framework with Exposed Mn2+ Coordination Sites; J. Am. Chem. Soc.; 128; 2006; 16876-16883.

Banglin Chen et al; Hydrogen Adsorption in an Interpenetrated Dynamic Metal-Organic Framework; Inorganic Chemistry; vol. 45; No. 15; 2006; 5718-5720.

Xi-Sen Wang et al; A Mesoporous Metal-Organic Framework with Permanent Porosity; J. Am. Chem. Soc.; 128; 2006; 16474-16475.

Shengqian Ma et al; Framework-Catenation Isomerism in Metal-Organic Frameworks and its Impact on Hydrogen Uptake; J. Am. Chem. Soc.; 129; 2007; 1858-1859.

Shengqian Ma et al; Metal-Organic Framework from an Anthracene Derivative Containing Nanoscopic Cages Exhibiting High Methane Uptake; J. Am. Chem. Soc.; 130; 2008; 1012-1016.

Aiguo Hu et al; Chiral Porous Hybrid Solids for Practical Heterogeneous Asymmetric Hydrogenation of Aromatic Ketones; J. Am. Chem. Soc.; 125; 2003; 11490-11491.

Halder et al; Guest-Dependent Spin Crossover in a Nanoporous Molecular Framework Material; Science 298; 1762; 2002.

Janiak, Christopher; Engineering Coordination Polymers Towards Applications; The Royal Society of Chemistry; 2003; 2781-2804.

Yan-Zhen Zheng et al; Assembling Magnetic Nanowires into Networks: A Layered COII Carboxylate Coordination Polymer Exhibiting Single-Chain-Magnet Behavior; Angew. Chem. Int. Ed.; 45; 2006; 6310-6314.

Chengtao Yu et al; Magnetic Properties of a Noninterpenetrating Chiral Porous Cobalt Metal-Organic Framework; Journal of Applied Physics; 101; 2007; 09E108-1-09E108-3.

Humphrey et al; Porous Cobalt(II)-Organic Frameworks with Corrugated Walls: Structurally Robust Gas-Sorption Materials; Angew. Chem. Int. Ed.; 46; 2007; 272-275.

Shengqian Ma et al; Metal-Organic Framework Based on a Trinickel Secondary Building Unit Exhibiting Gas-Sorption Hysteresis; Inorganic Chemistry; vol. 46; No. 9; 2007; 3432-3434.

Shengqian Ma et al; Ultramicroporous Metal-Organic Framework Based on 9, 10-Anthracenedicarboxylate for Selective Gas Adsorption; Inorganic Chemistry; vol. 46; No. 21; 2006; 8499-8501.

Banglin Chen et al; A Triply Interpenetrated Microporous Metal-Organic Framework for Selective Sorption of Gas Molecules; Inorganic Chemistry; vol. 46; No. 21; 2007; 8490-8492.

D. Bradshaw et al; Design, Chirality, and Flexibility in Nanoporous Molecule-Based Materials; Acc. Chem. Res.; 38; 2005; 273-282.

Shengqian Ma et al; A Mesh-Adjustable Molecular Sieve for General Use in Gas Separation; Angew. Chem. Int. Ed.; 46; 2007; 2458-2462.

A. L. Spek; Single-Crystal Structure Validation with the Program PLATON; J. Appl. Cryst.; 36; 2003; 7-13.

R. E. Rondeau; Slush baths; Journal of Chemical and Engineering Data; 1965; 124.

Phipps et al; General Purpose Low Temperature Dry-Ice Baths; Journal of Chemical Education; 664.

Danil N. Dybtsev et al; Rigid and Flexible: A Highly Porous Metal-Organic Framework with Unusual Guest-Dependent Dynamic Behavior; Angew. Chem. Int. Ed.; 43; 2004; 5033-5036.

Hyungphil Chun et al; Synthesis, X-ray Crystal Structures, and Gas Sorption Properties of Pillared Square Grid Nets Based on Paddle-Wheel Motifs: Implications for Hydrogen Storage in Porous Materials; Chem. Eur. J.; 11; 2005; 3521-3529.

Bao-Qing Ma et al; Microporous Pillared Paddle-Wheel Frameworks Based on Mixed-Ligand Coordination of Zinc Ions; Inorganic Chemistry; vol. 44; No. 14; 2005; 4912-4914.

Eun-Young Choi et al; Benzene-Templated Hydrothermal Synthesis of Metal-Organic Frameworks with Selective Sorption Properties; Chem. Eur. J.; 10; 2004; 5535-5540.

Banglin Chen et al; Selective Gas Sorption within a Dynamic Metal-Organic Framework; Inorganic Chemistry; vol. 46; No. 21; 2007; 8705-8709.

Rosseinsky; Recent Developments in Metal-Organic Framework Chemistry: Design, Discovery, Permanent Porosity and Flexibility; Microporous and Mesoporous Materials; 73; 2004; 15-30.

Rowsell; Metal-Organic Frameworks: A New Class of Porous Materials; Microporous and Mesoporous Materials; 73; 2004; 3-14.

Lawrence Jr., Frank M.; Notice of Allowance and Fees Due; U.S. Appl. No. 11/738,730; dated October 26, 2009.

Author(s) Unknown: Coordination Complex; Wikipedia; en.wikipedia.org/Coordinationcomplex; last viewed Mar. 12, 2010.

Author(s) Unknown; Ligand; Wikipedia; en.wikipedia.org/wiki/Ligand; last viewed Mar. 12, 2010.

Messler, Gary L. and Tarr, Donald A.; Inorganic Chemistry, Second Ed., 1999, p. 286, Prentice Hall.

* cited by examiner

○ Ni
◉ O
⊘ μ$_3$-OH
● H$_2$O
⊘ C

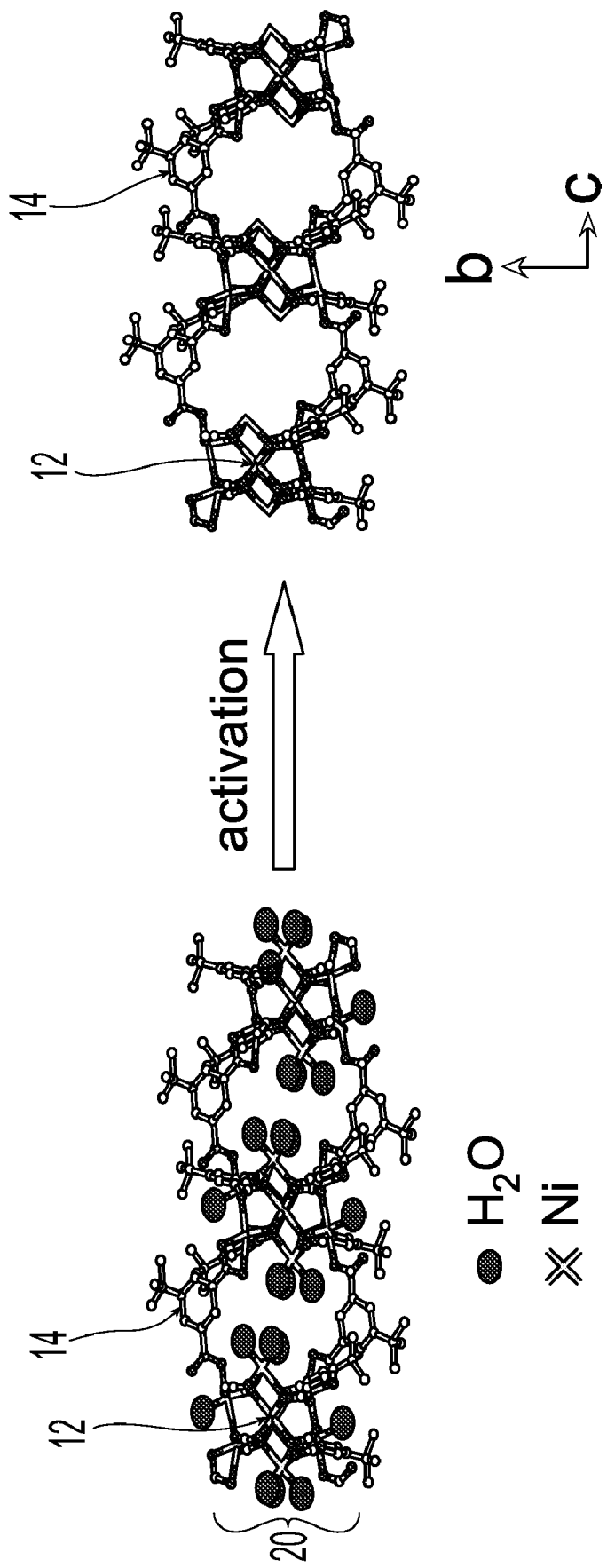

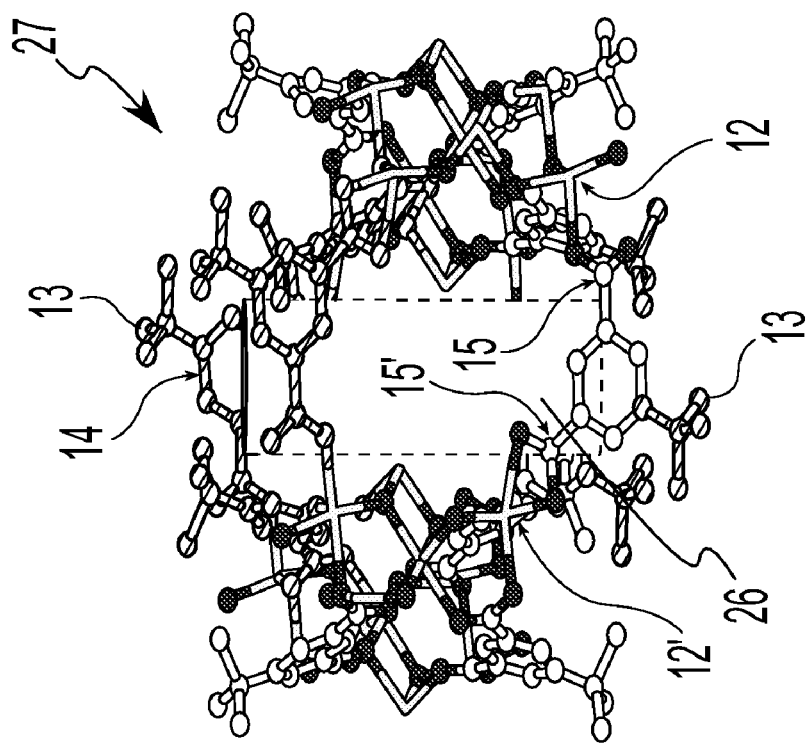
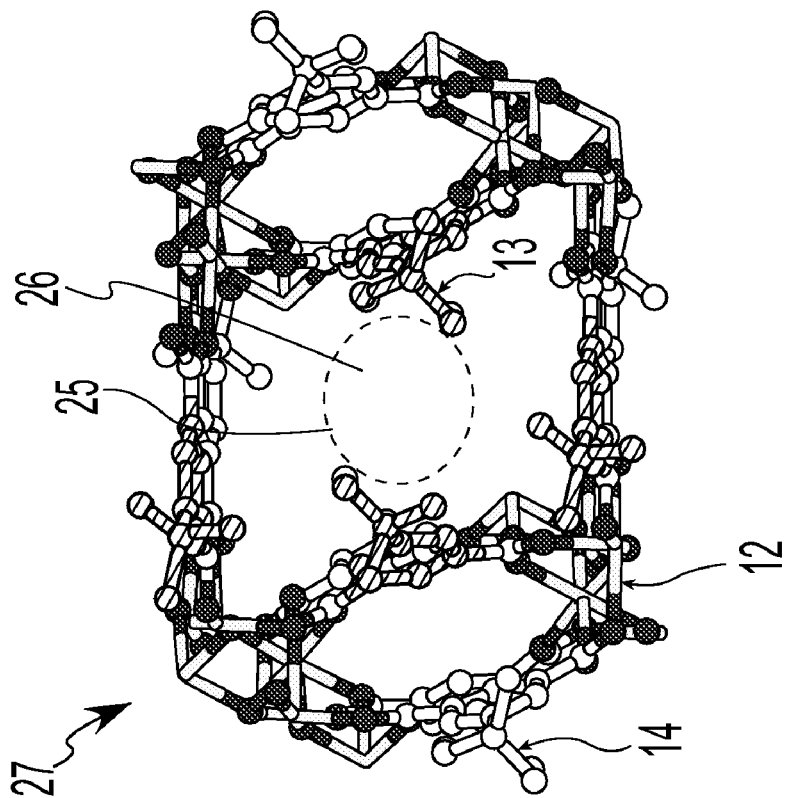
• H₂O
✕ Ni
FIG. 4b
FIG. 4a

4'-tert-butyl-biphenyl-3,5-dicarboxylate
BBPDC

4'-methyl-biphenyl-3,5-dicarboxylate
MBPDC 5-isopropyl-1,3-benzene-dicarboxylate
PBDC 4'-isopropyl-biphenyl-3,5-dicarboxylate
PBPDC 4'-trifluoromethyl-biphenyl-3,5-dicarboxylate
TFMBPDC 3',5'-di-tert-butyl-biphenyl-3,5-dicarboxylate
DBBPDC 3',5'-bis-trifluormethyl-biphenyl-3,5-dicarboxylate
BTFMBPDC 3',5'-diisopropyl-biphenyl-3,5-dicarboxylate
DPBPDC 3,5-di-tert-butyl-benzoate
DBB 3,5-di-tert-butyl-4-hydroxy-benzoate
DBHB 4-tert-butyl-benzoate
TBB 4-isopropyl-benzoate
IPB 5-tert-butyl-1,3-benzenediimidazolate

BBDI 5-tert-butyl-1,3-benzenedi(3'-pyridine)

3'-BBDP 5-tert-butyl-1,3-benzenedi(4'-pyridine)

4'-BBDP 5-tert-butyl-1,3-benzenedi(3'H-3'pyrizole)

3'-BBDPz 5-tert-butyl-1,3-benzenedi(3'H-4'pyrizole)

4'-BBDPz 5-tert-butyl-1,3-benzene dicarboxylate
BBDC 5-butoxy-1,3-benzenedicarboxylate
BOBDC 5-butylsulfonyl-1,3-benzenedicarboxylate
BSBDC 5-tert-butyl-1,3-benzeneditetrazolate
BBDT

MESH-ADJUSTABLE MOLECULAR SIEVE

CROSS-REFERENCES TO RELATED APPLICATIONS

This application claims the benefit of U.S. Provisional Application No. 60/899,115 filed Feb. 2, 2007.

STATEMENT REGARDING FEDERALLY-SPONSORED RESEARCH AND DEVELOPMENT

This invention was made in the course of research partially supported by a grant from the National Science Foundation (CHE-0449634). The government has certain rights in this invention.

REFERENCE TO AN APPENDIX (Not Applicable)

BACKGROUND OF THE INVENTION

1. Field of the Invention

This invention relates generally to metal-organic framework-based molecular sieves for selective gas adsorption and particularly to such sieves which provide thermally-dynamic pore sizes which are continuously adjustable.

2. Description of the Related Art

Gas separation is an important operation in many industries and conventional processes include distillation, absorption, and molecular sieves. However, using such processes to separate, for example, mixtures comprising chemical pairs of similarly-sized molecules or those with similar boiling points such as ethylene and propylene, methane and ethylene, nitrogen and methane, nitrogen and oxygen, hydrogen and carbon monoxide, and hydrogen and nitrogen can be difficult.

Recently, metal-organic frameworks (MOFs) have been utilized to produce porous materials suitable as molecular sieves for adsorbing specific molecular species. Such frameworks, which comprise metal clusters linked together in a reticular structure with linking ligands, can provide predetermined pore size and functionality. However, when the size disparity of the gas pairs to be separated is small, a molecular sieve with the optimum pore size is not always readily available and a mismatch inevitably leads to an inefficient operation. Furthermore, the pore size of even MOFs is fixed upon activation. Therefore, the need exists for a molecular sieve capable of dynamically providing a continuum of pore sizes. Particularly, the need exists for a molecular sieve having a continuum of pore sizes in the range of most commercially important gas separations.

SUMMARY OF THE INVENTION

To meet these needs, the present invention features a composition of matter that contains pores with a temperature-adjustable pore opening. This feature allows the composition to be used with mixtures of molecules by the mere expedient of adjusting the composition to a pre-selected temperature that fixes the temperature-adjustable pore opening to a size that allows for the passage of molecules having a size less than the size of the pre-selected temperature-adjustable pore opening.

The composition of matter comprises a plurality of metal clusters and a plurality of amphiphilic ligands with each ligand comprising a hydrophobic moiety, a first hydrophilic moiety, and a second hydrophilic moiety. The first hydrophilic moiety bonds to a first metal cluster while the second hydrophilic moiety bonds to a second metal cluster. The plurality of metal clusters are bonded to a plurality of amphiphilic ligands to form a tri-layer with the tri-layer comprising a first layer of amphiphilic ligands and a second layer of amphiphilic ligands. The plurality of metal clusters are located between and bonded to the first amphiphilic ligand layer and the second amphiphilic ligand layer to form a third layer of the tri-layer. A plurality of tri-layers are held in proximity with each other with intermolecular forces such as van der Waals forces to form the composition and contain pores with temperature-adjustable pore openings.

The temperature-adjustable pore openings are associated with hydrophobic pores and are formed by a plurality of hydrophobic moieties. In addition, a plurality of hydrophobic chambers are formed in the plurality of tri-layers and are molecularly accessible through the hydrophobic pores having a temperature-adjustable pore opening. A plurality of hydrophilic pores are in communication with the temperature-adjustable pore openings and at least a portion of the hydrophilic pores extend to the boundaries of the composition.

The tri-layers are held in proximity with each other by van der Waals interactions between the hydrophobic moieties of the first amphiphilic ligand layer of a first tri-layer and the second amphiphilic ligand layer of a second tri-layer.

The metal clusters are formed from a wide variety of metal cations including cations of aluminum, gallium, germanium, the transition metals including scandium through zinc, yttrium through cadmium, lanthanum through mercury, and actinium, the lanthanides from cerium through lutetium, and the actinides from thorium to the last known element. The amphiphilic ligand is selected from a group of compounds represented by the formulas:

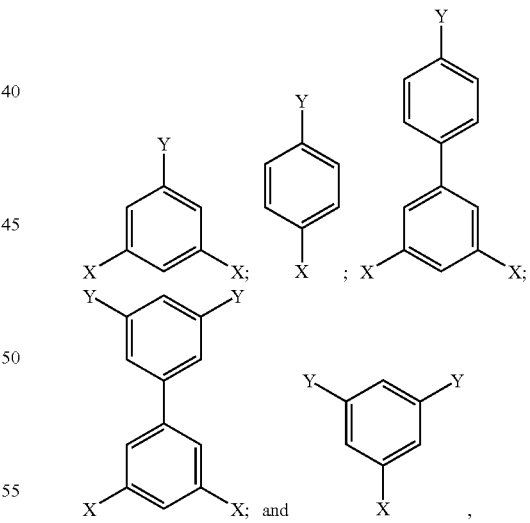

where X is at least one of carboxylate, cyano, phosphonate, sulfonate, imidazolate, pyridine, pyrazole, and tetrazolate; and Y is at least one of tert-butyl, methyl, isopropyl, trifluoromethyl, butoxyl, butylsulfonyl, alkyl, halogenated alkyl, alkenyl, alkynyl, and alkoxyl.

More specifically, the amphiphilic ligand is selected from the following ligands: 4'-tert-butyl-biphenyl-3,5-dicarboxylate; 4'-methyl-biphenyl-3,5-dicarboxylate; 5-isopropyl-1,3-benzene-dicarboxylate; 4'-isopropyl-biphenyl-3,5-dicarboxylate; 4'-trifluoromethyl-biphenyl-3,5-dicarboxylate; 3',5'-di-tert-butyl-biphenyl-3,5-dicarboxylate; 3,5-di-tert-butyl-benzoate; 3,5-di-tert-butyl-4-hydroxy-benzoate; 4-tert-butyl-benzoate; 4-isopropyl-benzoate; 3',5'-bis-trifluormethyl-biphenyl-3,5-dicarboxylate; 3',5'-diisopropyl-biphenyl-3,5-dicarboxylate; 5-tert-butyl-1,3-benzenediimidazolate; 5-tert-butyl-1,3-benzenedi(3'-pyridine); 5-tert-butyl-1,3-benzenedi(4'-pyridine); 5-tert-butyl-1,3-benzenedi(3'H-3'pyrizole); 5-tert-butyl-1,3-benzenedi(3'H-4'pyrizole); 5-tert-butyl-1,3-benzenedicarboxylate; 5-butoxy-1,3-benzenedicarboxylate; 5-butylsulfonyl-1,3-benzenedicarboxylate; and 5-tert-butyl-1,3-benzeneditetrazolate.

The 4'-methyl-biphenyl-3,5-dicarboxylate amphiphilic ligand was prepared according to the steps set forth in the flow chart shown in FIG. 6.

The metal-ligand composition of matter of the present invention is prepared by dissolving a metal ion salt of the metal ions and amphiphilic ligands in a solvent to form a solution, forming the metal-ligand composition of matter by solvothermal reaction of the solution of metal ions and the amphiphilic ligand ions; and then crystallizing the metal-ligand composition from the resultant solution of the solvothermal reaction.

The temperature-dependent pore openings of the metal-ligand composition are defined by the equation: $D=D_0+\alpha T$, where D is the kinetic opening, in Angstroms, of the temperature-adjustable pore opening, $D_0$ is the temperature-adjustable pore opening at 0 deg. Kelvin, $\alpha$ is a constant related to the amphiphilic ligand, and T is the temperature in degrees K.

The metal-ligand composition of the present invention is used to separate molecules of various sizes from each other. Separation is accomplished by maintaining the metal-ligand composition at a preselected temperature to set the size of the temperature-adjustable pore opening to the size necessary for separation and contacting a gaseous mixture with the metal-ligand composition to selectively adsorb one or more gases from the mixture with a molecular size smaller than the size of the temperature-dependent pore opening. For example, by setting the metal-ligand composition to the desired temperature mixtures of gases such as $H_2/N_2$, $H_2/CO$, $N_2/O_2$, $N_2/CH_4$, $CH_4/C_2H_4$, and $C_2H_4/C_3H$ can be separated from each other.

An example of the metal-ligand composition of the present invention, the desolvated form, has the molecular formula $Ni_8(\mu_3\text{-}OH)_4(C_{12}H_{12}O_4)_6$ where $C_{12}H_{12}O_4$ is the molecular formula of the ligand 5-tert-butyl-1,3-benzenedicarboxylate (BBDC) while its solvated form, which is in its initial form after preparation and crystallization from solution, has the formula $Ni_8(\mu_3\text{-}OH)_4(C_{12}H_{12}O_4)_6(H_2O)_8.8H_2O$. The temperature-dependent pore openings of the desolvated from of this metal-ligand complex are defined by the equation $D=0.0076$ T+2.76, where D is the kinetic opening in Angstroms of the temperature-adjustable pore opening and T is the temperature in degrees Kelvin. The hydrophilic channels have an atom-to-atom distance of about 8 Å and about 5 Å considering van der Waals radii which limits the overall size of the molecule than can be adsorbed. By setting the metal-ligand composition to the desired temperature according to the above equation, mixtures of gases such as $H_2/N_2$, $H_2/CO$, $N_2/O_2$, $N_2/CH_4$, $CH_4/C_2H_4$, and $C_2H_4/C_3H$ can be separated from each other.

Other examples of the metal-ligand composition are:
$Zn_2((CH_3)_3CC_6H_4C_6H_3(CO_2)_2)_2$,
$Co_2((CH_3)_3CC_6H_4C_6H_3(CO_2)_2)_2$, and
$Cu_2((CH_3)_3CC_6H_4C_6H_3(CO_2)_2)_2$, where $(CH_3)_3CC_6H_4C_6H_3(CO_2)_2$ is the molecular formula for 4'-tert-butyl-biphenyl-3,5-dicarboxylate (BBPDC). The temperature-adjustable pore openings of all of these compositions are defined by the equation D=0.0073 T+2.83, where D is the kinetic opening of the temperature-dependent pore opening in Angstroms and T is the temperature in degrees Kelvin. The metal-ligand composition of the present invention is used to separate molecules of various sizes from each other. For example, by setting the metal-ligand composition to the desired temperature mixtures of gases such as $H_2/N_2$, $H_2/CO$, $N_2/O_2$, $N_2/CH_4$, $CH_4/C_2H_4$, and $C_2H_4/C_3H$ can be separated from each other. The solvated forms of three metal-ligand compositions have the molecular formulas:

$Zn_2(H_2O)_2((CH_3)_3CC_6H_4C_6H_3(CO_2)_2)_2.3(HCON(CH_3)_2$, $Co_2(H_2O)_2((CH_3)_3CC_6H_4C_6H_3(CO_2)_2)_2.3(CH_3CON(CH_3)_2)$, and $Cu_2(H_2O)_2((CH_3)_3CC_6H_4C_6H_3(CO_2)_2)_2.3(HCON(CH_3)_2)$.

The foregoing and other objects, features and advantages of the invention will become apparent from the following disclosure in which one or more preferred embodiments of the invention are described in detail and illustrated in the accompanying drawings. It is contemplated that variations in procedures, structural features, and arrangement of parts may appear to a person skilled in the art without departing from the scope of or sacrificing any of the advantages of the invention.

BRIEF DESCRIPTION OF THE SEVERAL VIEWS OF THE DRAWINGS

FIG. 1b is a three-dimensional graphical rendition of the defined pores and chambers illustrated in FIG. 1a.

FIG. 3c is a three-dimensional graphical rendition of an exemplary octa-nickel metal cluster layer and including bound ligands before and after activation.

FIGS. 4a and 4b are three-dimensional graphical renditions of two views of an exemplary molecular gate-like structure.

DETAILED DESCRIPTION OF THE INVENTION

Figure 1A:
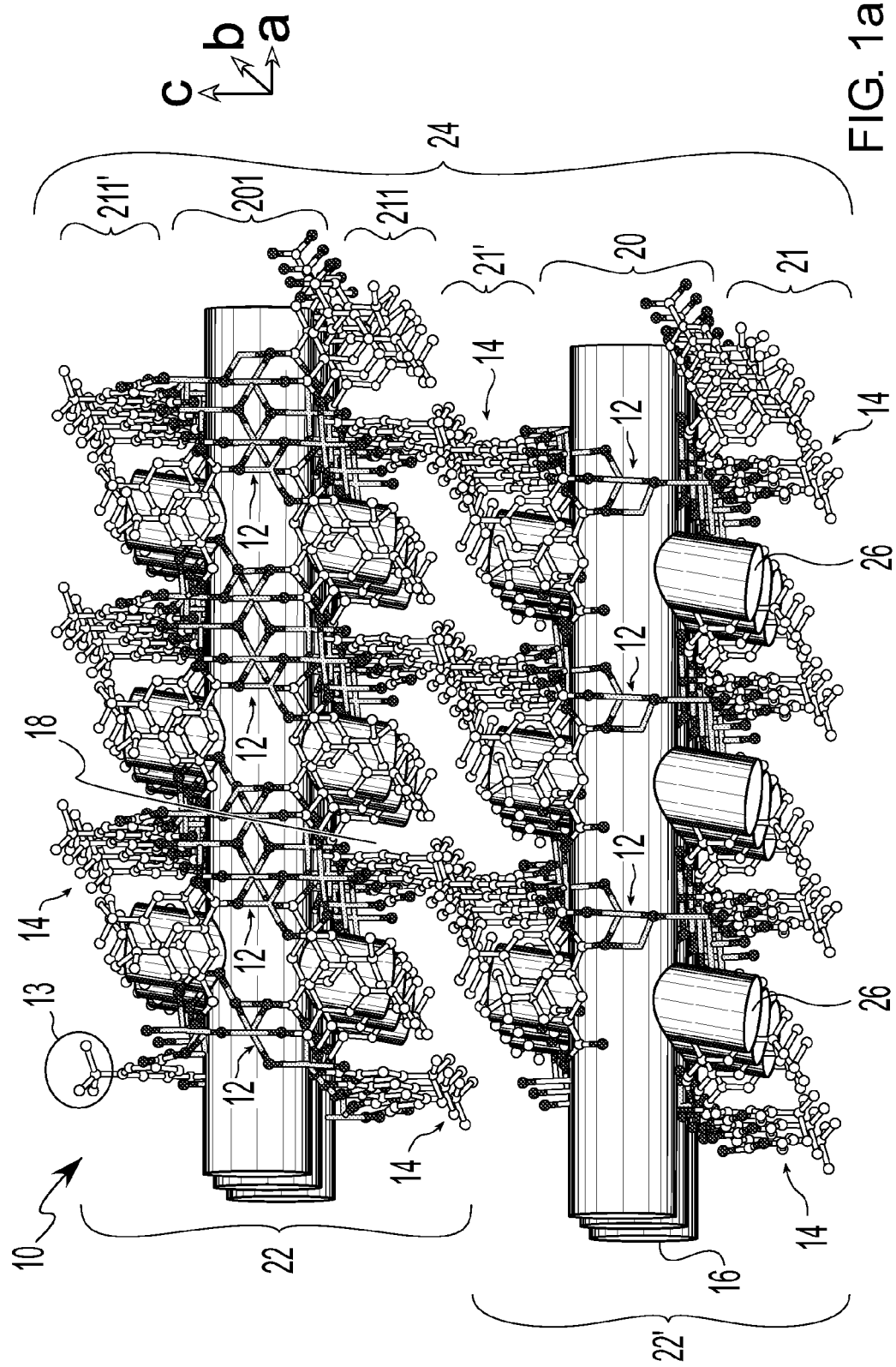
FIG. 1a is a three-dimensional graphical rendition of $Ni_8(\mu_3\text{-}OH)_4$(5-tert-butyl-1,3-benzenedicarboxylate)$_6$ $(Ni_8(\mu_3\text{-}OH)_4(BBDC)_6)$ illustrating the multiple tri-layer structure with the attendant hydrophilic and hydrophobic pores and hydrophobic chambers.

An exemplary embodiment, a nickel-BBDC-based composition of matter 10 is shown in FIG. 1a. The composition of matter 10 comprises a plurality of $Ni_8(\mu_3\text{-}OH)_4$ metal clusters 12 and a plurality of BBDC amphiphilic ligands 14. Each ligand 14 comprises a hydrophobic moiety 13, a first hydrophilic moiety 15 (best seen in FIG. 4b), and a second hydrophilic moiety 15' (best seen in FIG. 4b). The first hydrophilic moiety 15 bonds to a first metal cluster 12 and the second hydrophilic moiety 15' bonds to a second metal cluster 12'. While the hydrophilic moieties 15, 15' are shown, for example, in the instant example, as encompassing the carboxylate, in fact, as will be appreciated by those skilled in the art, each oxygen may itself function as a hydrophilic moiety and, thus, a single carboxylate may bond to both a first metal cluster 12 and a second metal cluster 12'. The plurality of metal clusters 12 are bonded to a plurality of amphiphilic ligands 14 to form a tri-layer 22, 22' and the tri-layer 22 comprises a first layer of amphiphilic ligands 211, and a second layer of amphiphilic ligands 211'. The plurality of metal clusters 12 are located between, and bonded to, the first amphiphilic ligand layer 211 and the second amphiphilic ligand layer 211' to form a third layer of the tri-layer, a metal cluster layer 201. A plurality of tri-layers 22, 22' are held in proximity by van der Waals forces between the hydrophobic moieties 13 of the first amphiphilic ligand layer 211 of a first tri-layer 22 and the hydrophobic moieties 13 of a second amphiphilic ligand layer 21' of a second tri-layer 22' to form a multi-tri-layer structure 24. While not wishing to be bound by any particular theory, it is believed that temperature-adjustable pore size hydrophobic pores 26 (also shown in 4a and 4b) are formed by a plurality of adjacent hydrophobic moieties 13 in a first amphiphilic ligand layer 211 and temperature-adjustable pore size hydrophobic pores 26 are formed by a plurality of adjacent hydrophobic moieties 13 in a second amphiphilic ligand layer 211' of the tri-layer 201. Adjacent pluralities of hydrophobic moieties 13 may then cooperate as a hydrophobic gate 27 (FIGS. 2b, 2c, 4a, and 4b) about the hydrophobic pore 26. A plurality of hydrophobic chambers 18 are formed in a plurality of tri-layer structures 22, 22' and are accessible through the temperature-adjustable pore size hydrophobic pores 26. A plurality of hydrophilic pores 16 are formed in the metal cluster layer 20, 201 and the plurality of hydrophilic pores 16 are in communication with the temperature-adjustable pore size hydrophobic pores 26 and the hydrophilic pores 16 extend to the boundaries of the composition of matter.

Figure 1B:
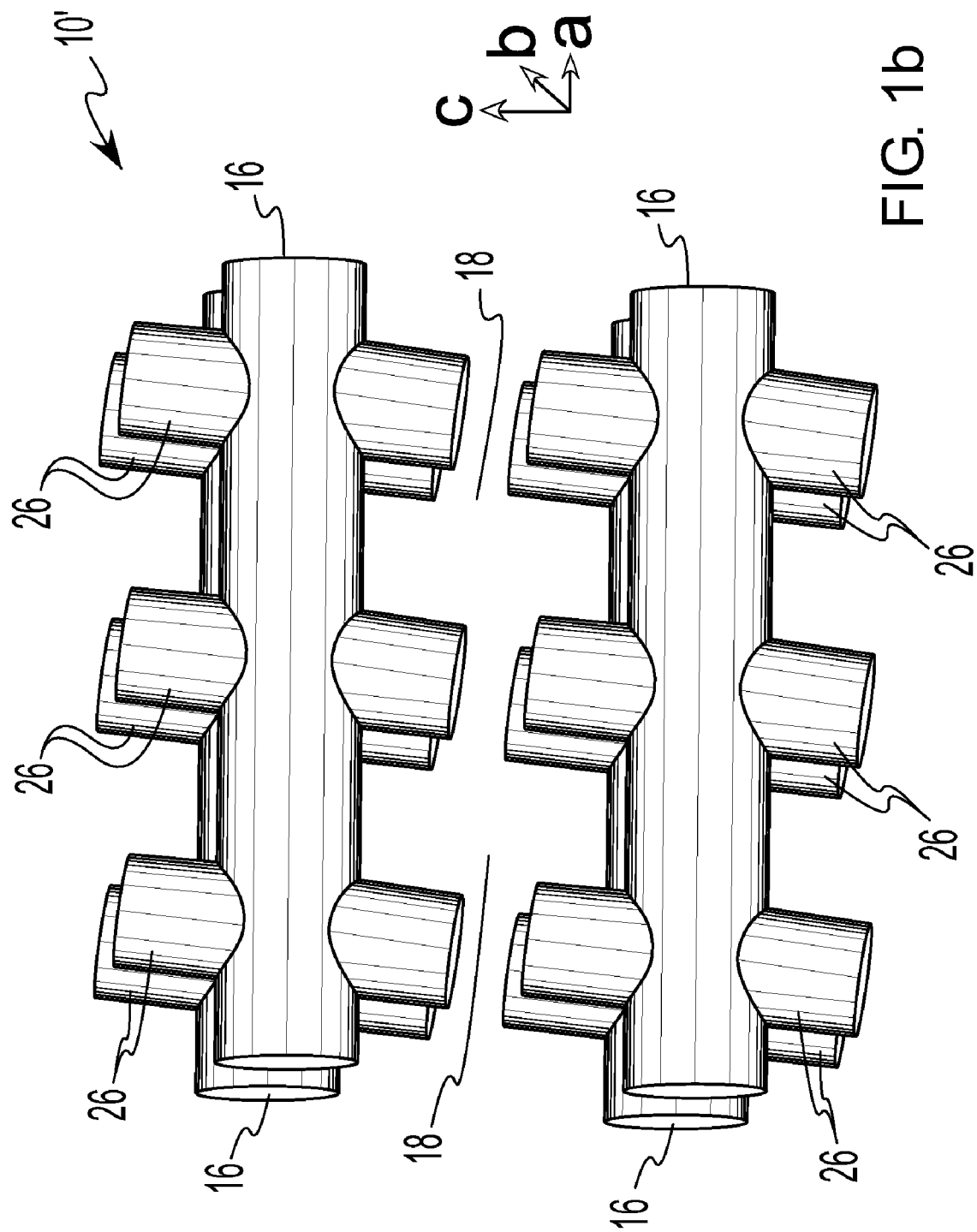

FIG. 1b, with the molecular structures of FIG. 1a removed, better illustrates the interconnected hydrophilic pores 16, hydrophobic chambers 18, and temperature-adjustable pore size hydrophobic pores 26.

Figure 2A:
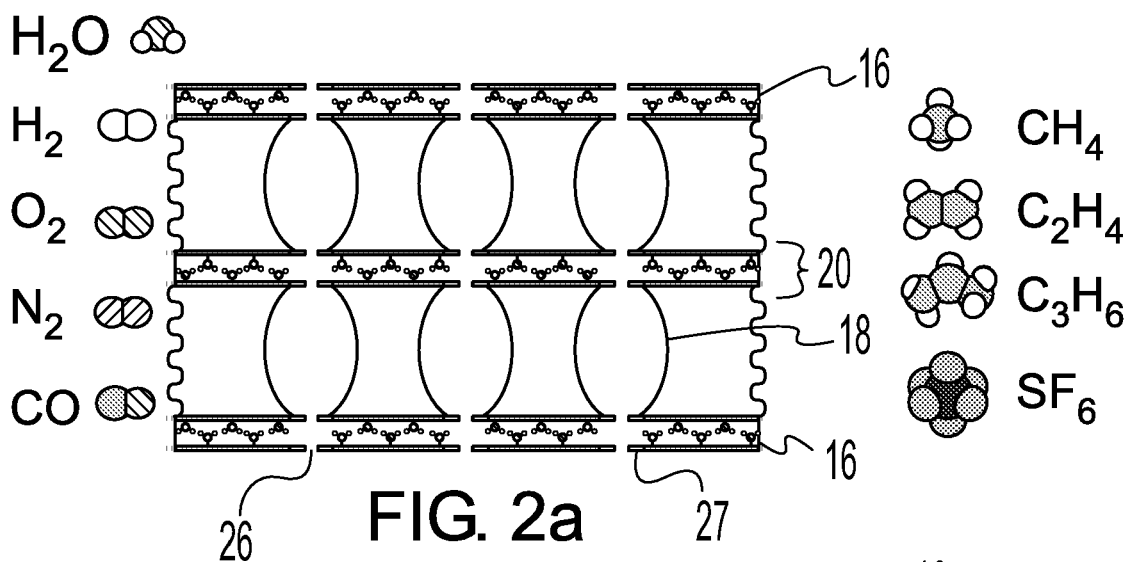
FIGS. 2a-2c are two-dimensional graphical renditions of the compound of FIG. 1a illustrating the defined pores, chambers, activation, and separable molecules.

FIG. 2a is a simplified cross-sectional view of the drawing of FIG. 1a illustrating interconnected hydrophilic pores 16, hydrophobic chambers 18, temperature-adjustable pore size hydrophobic pores 26, and temperature-adjustable pore size hydrophobic pore opening 25. As shown, the size of the opening 25 of the temperature-adjustable pore size hydrophobic pores 26 is controlled by the hydrophobic gates 27 which comprise the hydrophobic moieties 13 of the amphiphilic ligands 14. The hydrophobic chambers 18 are not accessible when the hydrophobic gates 27 do not allow access through the temperature-adjustable pore size hydrophobic pores 26.

Figure 2B:
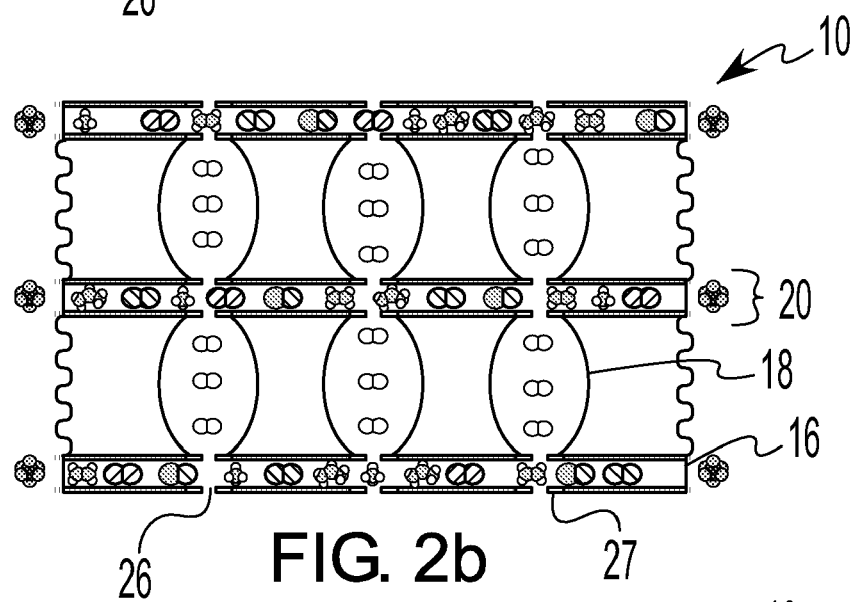
Figure 2C:
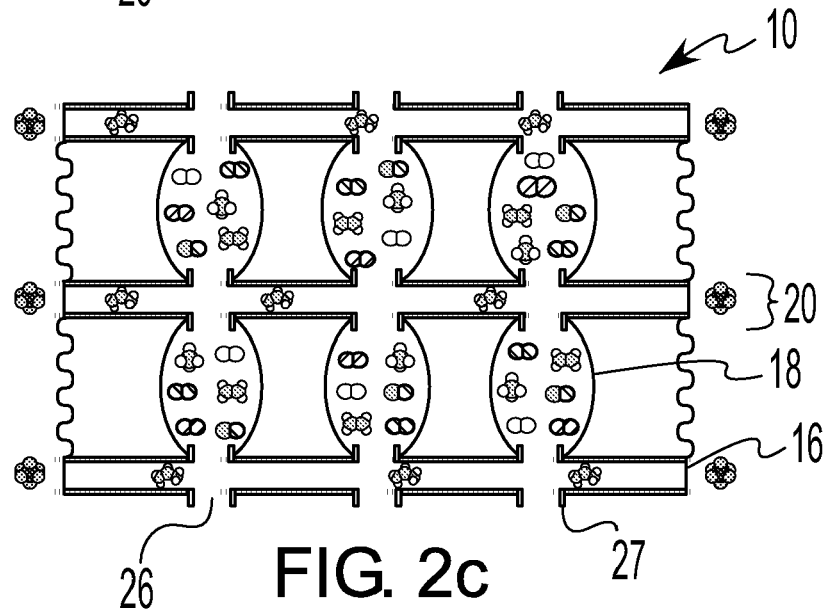
Figure 12:
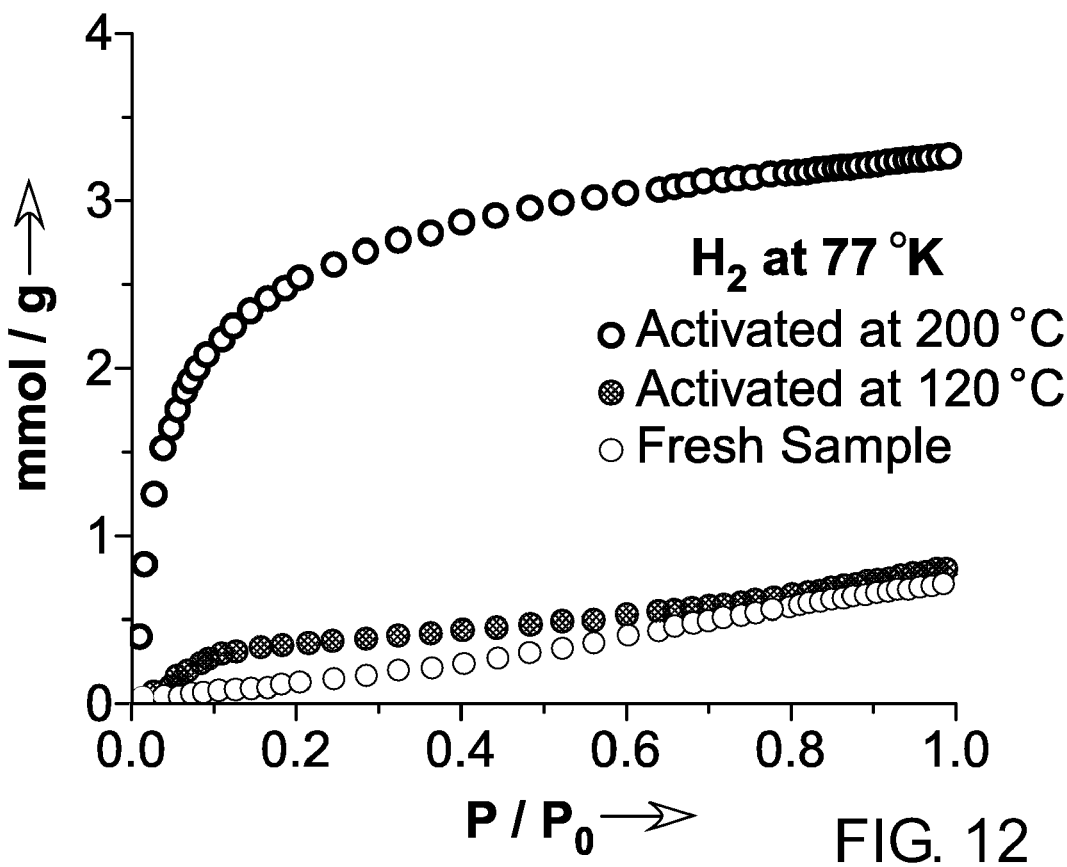
FIG. 12 shows $H_2$ adsorption isotherms at 77 deg. K. for fresh (solvated) $Ni_8(\mu_3\text{-}OH)_4(BBDC)_6$, $Ni_8(\mu_3\text{-}OH)_4(BBDC)_6$ activated at 120 deg. C, and $Ni_8(\mu_3\text{-}OH)_4(BBDC)_6$ activated at 200 deg. C.
Figure 13:
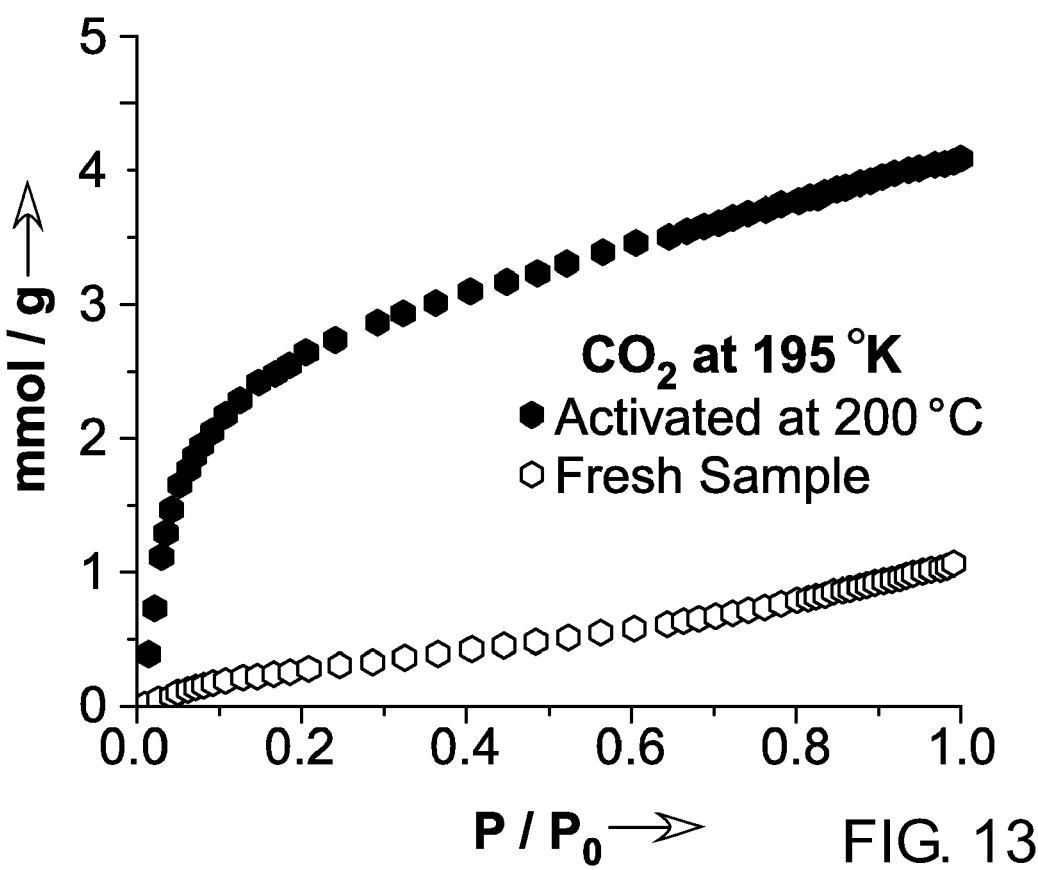
FIG. 13 shows $CO_2$ adsorption isotherms at 195 deg. K. for fresh (solvated) $Ni_8(\mu_3\text{-}OH)_4(BBDC)_6$ and $Ni_8(\mu_3\text{-}OH)_4(BBDC)_6$ activated at 200 deg. C.

This can be inferred from the crystal structure and is consistent with the gas adsorption data (e.g., FIGS. 12 and 13). A non-activated sample had very low uptake of either $H_2$ or $CO_2$. As shown in FIG. 2b, the water molecule guests and bound water must be removed for the compound to be active for gas adsorption. As shown in FIG. 2c, the temperature must be sufficient to allow molecules of interest to be adsorbed.

Figure 5:
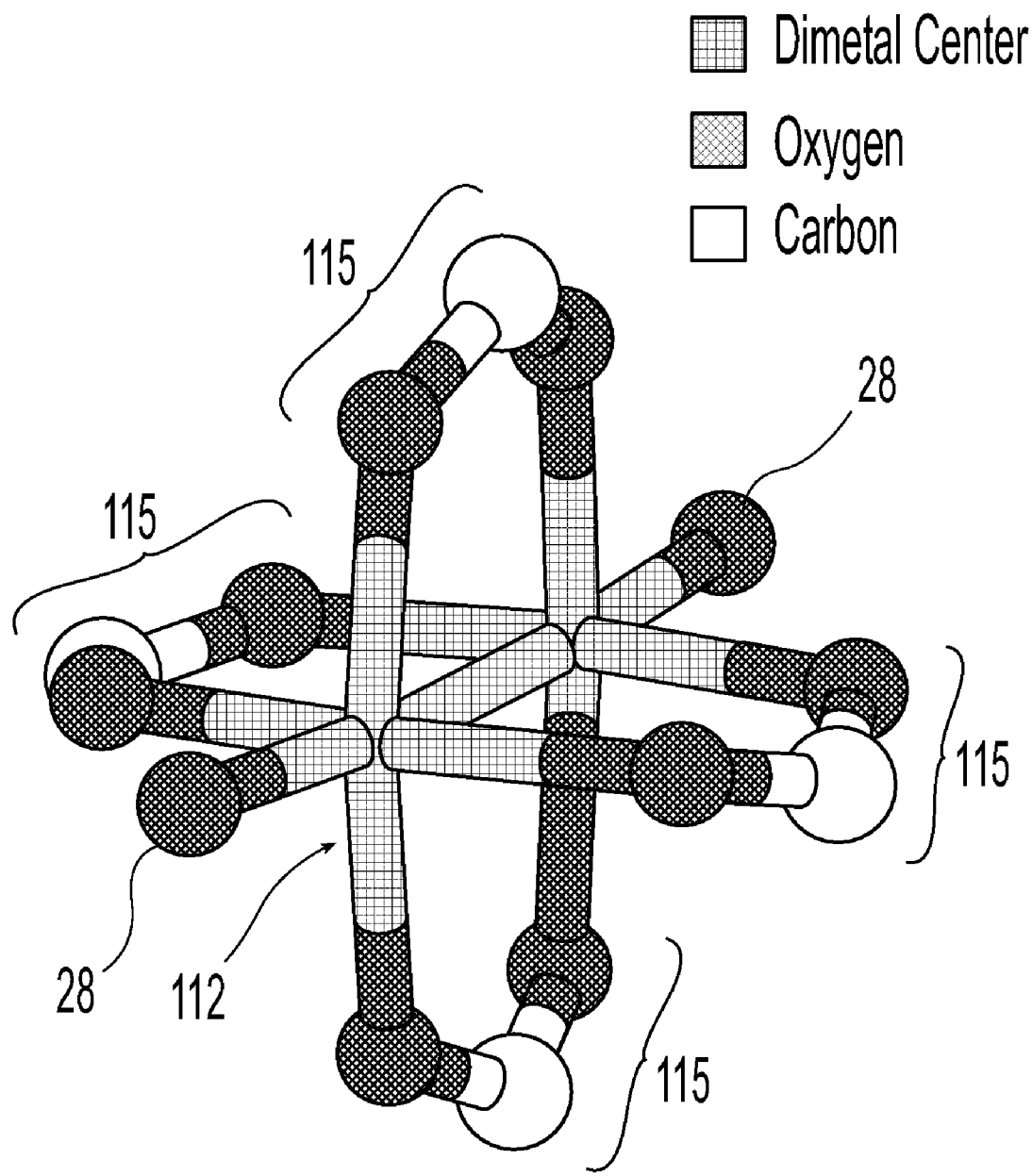
FIG. 5 is a three-dimensional graphical rendition of an exemplary bi-metal cluster bound with carboxylate groups of exemplary ligands and including aqua axial elements.

Nickel has been used for forming the metal clusters 12, while zinc, cobalt, and copper have been used to form dimetal clusters 112 (FIG. 5). Other metals may include those selected from the group consisting of aluminum, gallium, germanium, the other transition metals, including scandium through iron, yttrium through cadmium, lanthanum through mercury, and actinium, the lanthanides from cerium through lutetium, and the actinides from thorium to the last known element.

A number of exemplary amphiphilic ligands are shown in FIGS. 8a-8e. More generally, such ligands have the following form:

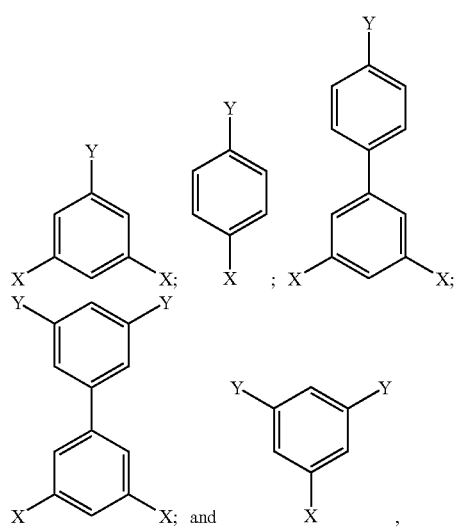

where X is at least one of carboxylate, cyano, phosphonate, sulfonate, imidazolate, pyridine, pyrazole, and tetrazolate and Y is at least one of tert-butyl, methyl, isopropyl, trifluoromethyl, butoxyl, butylsulfonyl, alkyl, halogenated alkyl, alkenyl, alkynyl, and alkoxyl.

As shown in FIGS. 1a, 3a-3c, 4a, and 4b, the hydrophilic moiety 15 covalently bonds to the metal ions to help form the metal cluster 12. Bonding of two clusters 12 by a single amphiphilic ligand 14 creates the tri-layered structure (e.g., 22, 22', FIG. 1a). While not wishing to be bound by any particular theory, it is believed vibration of the hydrophobic moiety 13 of the ligands 14 effects the observed temperature-adjustable molecular adsorption.

Specifically, the following ligands (including suggestive acronyms) are shown in FIGS. 8a-8e: 4'-tert-butyl-biphenyl-3,5-dicarboxylate (BBPDC); 4'-methyl-biphenyl-3,5-dicarboxylate (MPBDC); 5-isopropyl-1,3-benzene-dicarboxylate (PBDC); 4'-isopropyl-biphenyl-3,5-dicarboxylate (PBPDC); 4'-trifluoromethyl-biphenyl-3,5-dicarboxylate (TFMBPDC); 3',5'-di-tert-butyl-biphenyl-3,5-dicarboxylate (DBBPDC); 3,5-di-tert-butyl-benzoate (DBB); 3,5-di-tert-butyl-4-hydroxy-benzoate (DBHB); 4-tert-butyl-benzoate (TBB); 4-isopropyl-benzoate (IPB); 3',5'-bis-trifluormethyl-biphenyl-3,5-dicarboxylate (BTFMBPDC); 3',5'-diisopropyl-biphenyl-3,5-dicarboxylate (DPBPDC); 5-tert-butyl-1,3-benzenediimidazolate (BBDI); 5-tert-butyl-1,3-benzenedi(3'-pyridine) (3'-BBDP); 5-tert-butyl-1,3-benzenedi(4'-pyridine) (4'-BBDP); 5-tert-butyl-1,3-benzenedi(3'H-3'pyrizole) (3'-BBDPz); 5-tert-butyl-1,3-benzenedi(3'H-4'pyrizole) (4'-BBDPz); 5-tert-butyl-1,3-benzenedicarboxylate (BBDC); 5-butoxy-1,3-benzenedicarboxylate (BOBDC); 5-butylsulfonyl-1,3-benzenedicarboxylate (BSBDC); and 5-tert-butyl-1,3-benzeneditetrazolate (BBDT).

Generally, temperature-adjustable pore size molecular sieves are produced by dissolving a source of metal ions chosen from the list consisting of aluminum, gallium, germanium, the transition metals, including scandium through zinc, yttrium through cadmium, lanthanum through mercury, and actinium, the lanthanides from cerium through lutetium, and the actinides from thorium to the last known element and a source of amphiphilic ligands ions, the amphiphilic ligand ions chosen from the list consisting of:

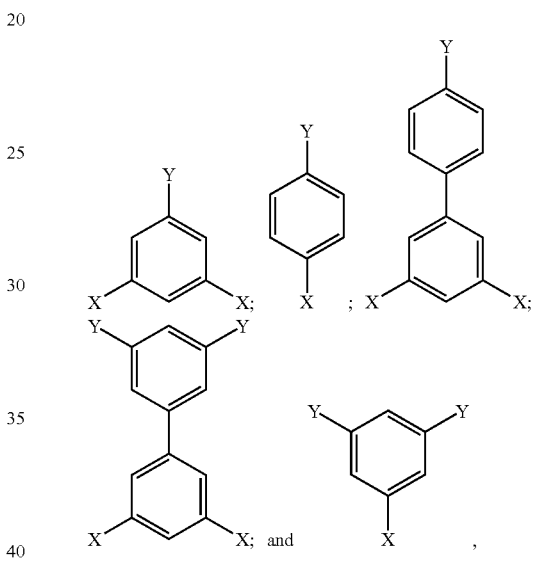

where X is at least one of carboxylate, cyano, phosphonate, sulfonate, imidazolate, pyridine, pyrazole, and tetrazolate and Y is at least one of tert-butyl, methyl, isopropyl, trifluoromethyl, butoxyl, and butylsulfonyl, alkyl, halogenated alkyl, alkenyl, alkynyl, and alkoxyl, forming the temperature-adjustable pore size molecular sieve by solvothermal reaction of the metal ions and the amphiphilic ligand ions, and crystallizing the temperature-adjustable pore size molecular sieve from the resultant solution. Specific, detailed syntheses are presented below for specific temperature-adjustable pore size molecular sieves.

Figure 3A:
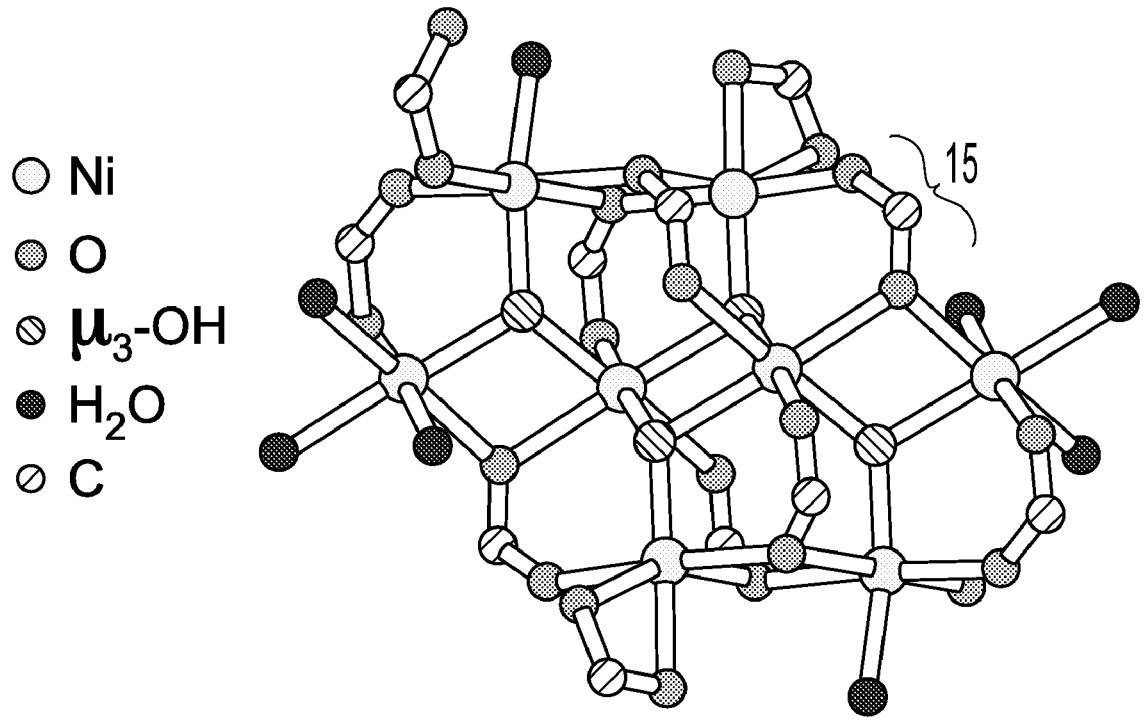
FIG. 3a is a three-dimensional graphical rendition of an exemplary octa-nickel metal cluster bound with carboxylate groups prior to activation.
Figure 3B:
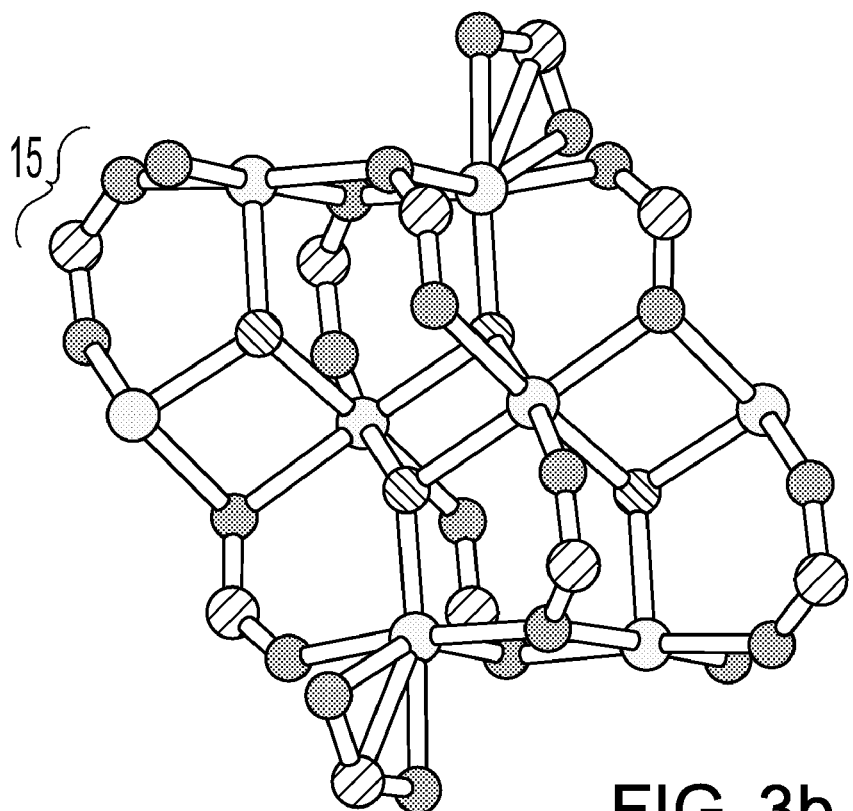
FIG. 3b is a three-dimensional graphical rendition of an exemplary octa-nickel metal cluster bound with carboxylate groups after activation.
Figure 10:
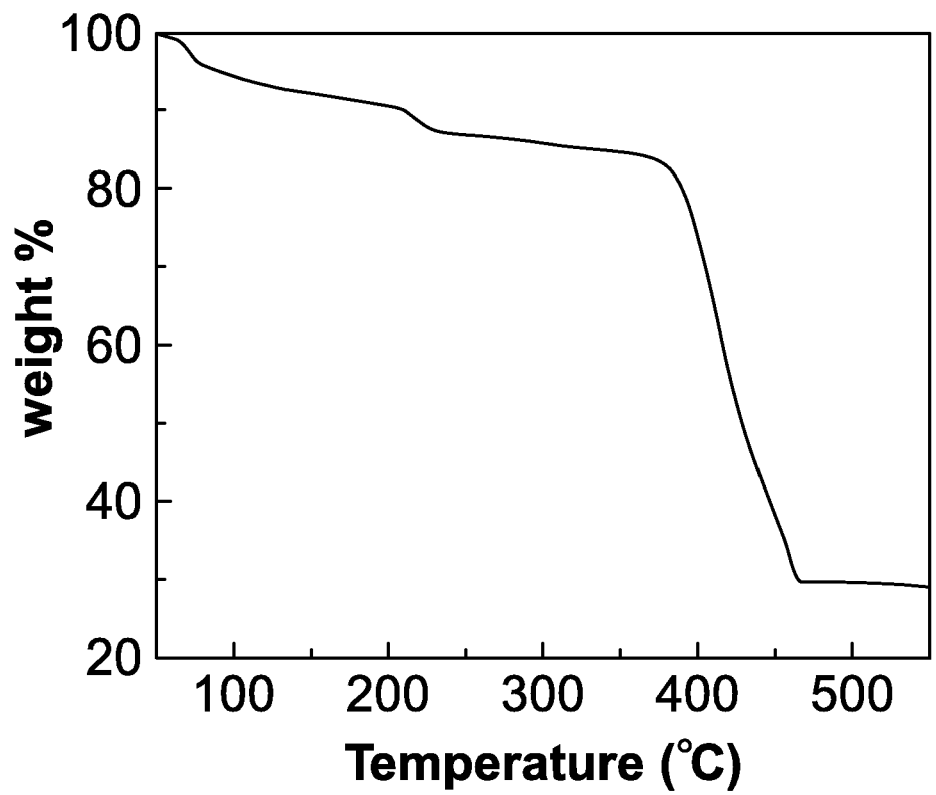
FIG. 10 is a thermogravimetric analysis (TGA) of $Ni_8(\mu_3\text{-}OH)_4(BBDC)_6$.
Figure 14:
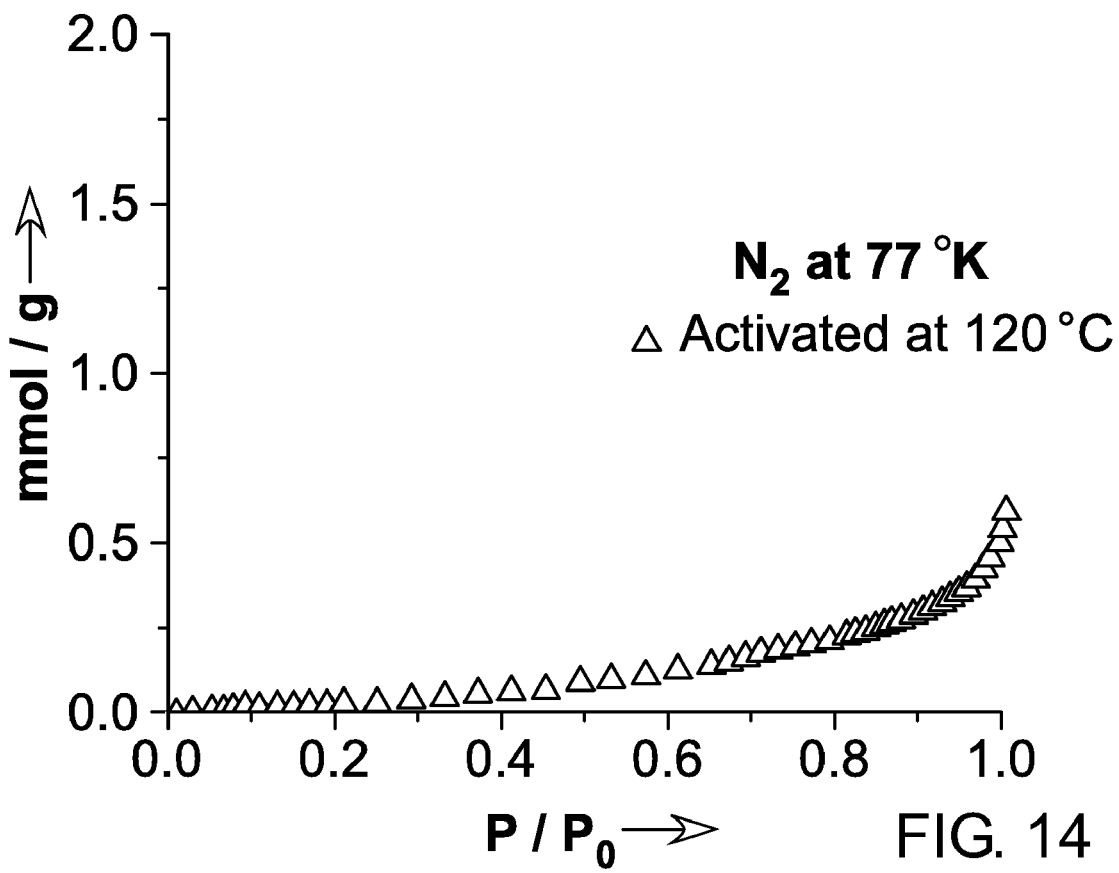
FIG. 14 is a $N_2$ adsorption isotherm at 77 deg. K. for $Ni_8(\mu_3\text{-}OH)_4(BBDC)_6$ activated at 120 deg. C.
Figure 15:
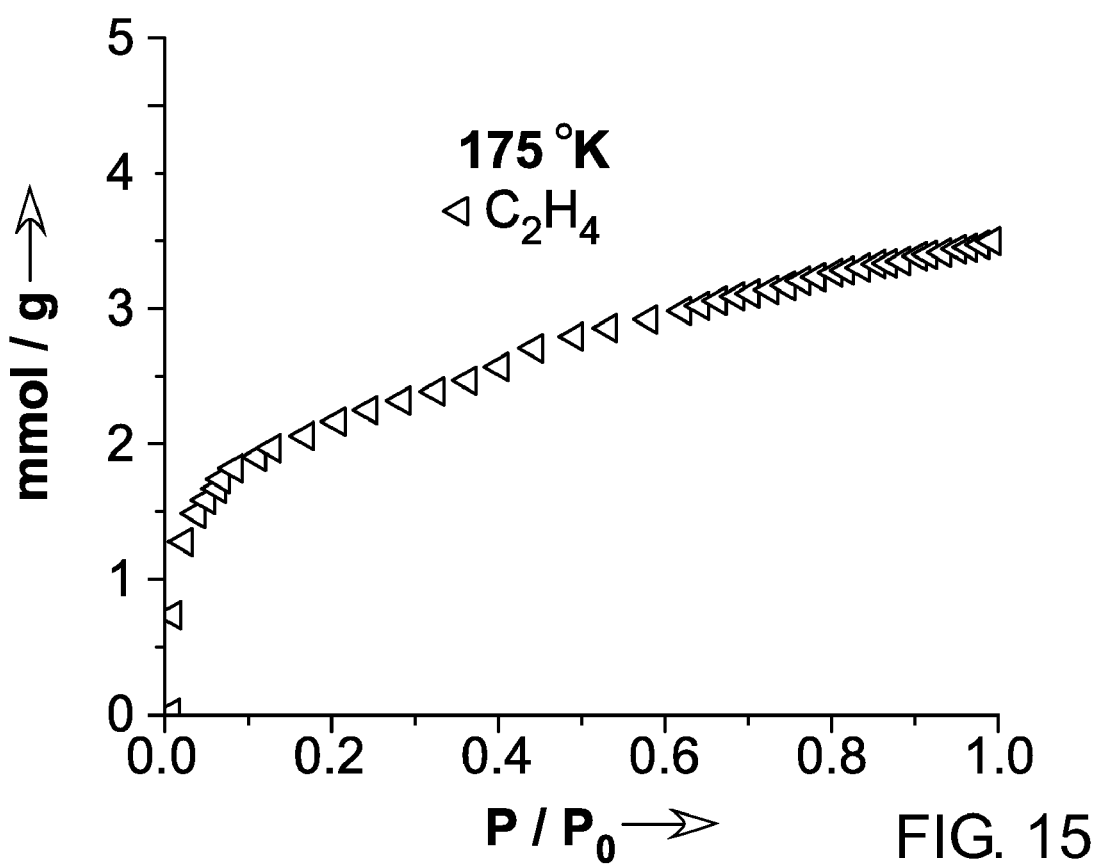
FIG. 15 is a $C_2H_4$ adsorption isotherm at 175 deg. K. for $Ni_8(\mu_3\text{-}OH)_4(BBDC)_6$.
Figure 16:
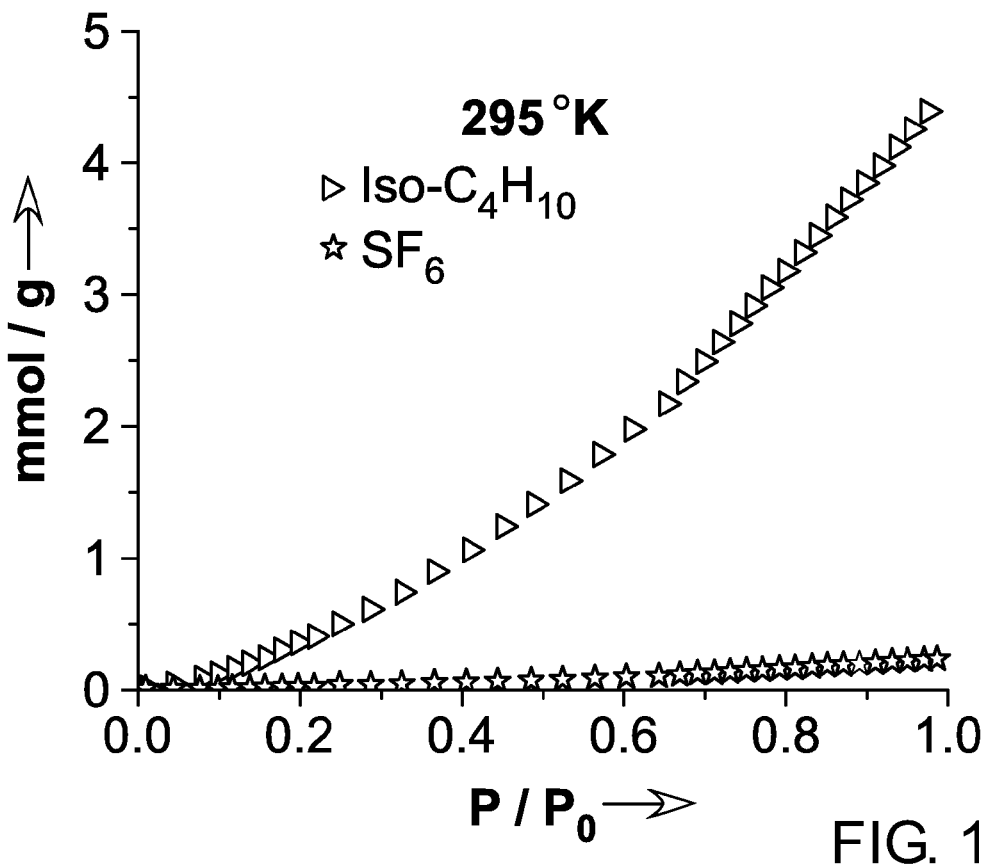
FIG. 16 shows iso-$C_4H_{10}$ and $SF_6$ adsorption isotherms at 295 deg. K. for $Ni_8(\mu_3\text{-}OH)_4(BBDC)_6$.
Figure 25:
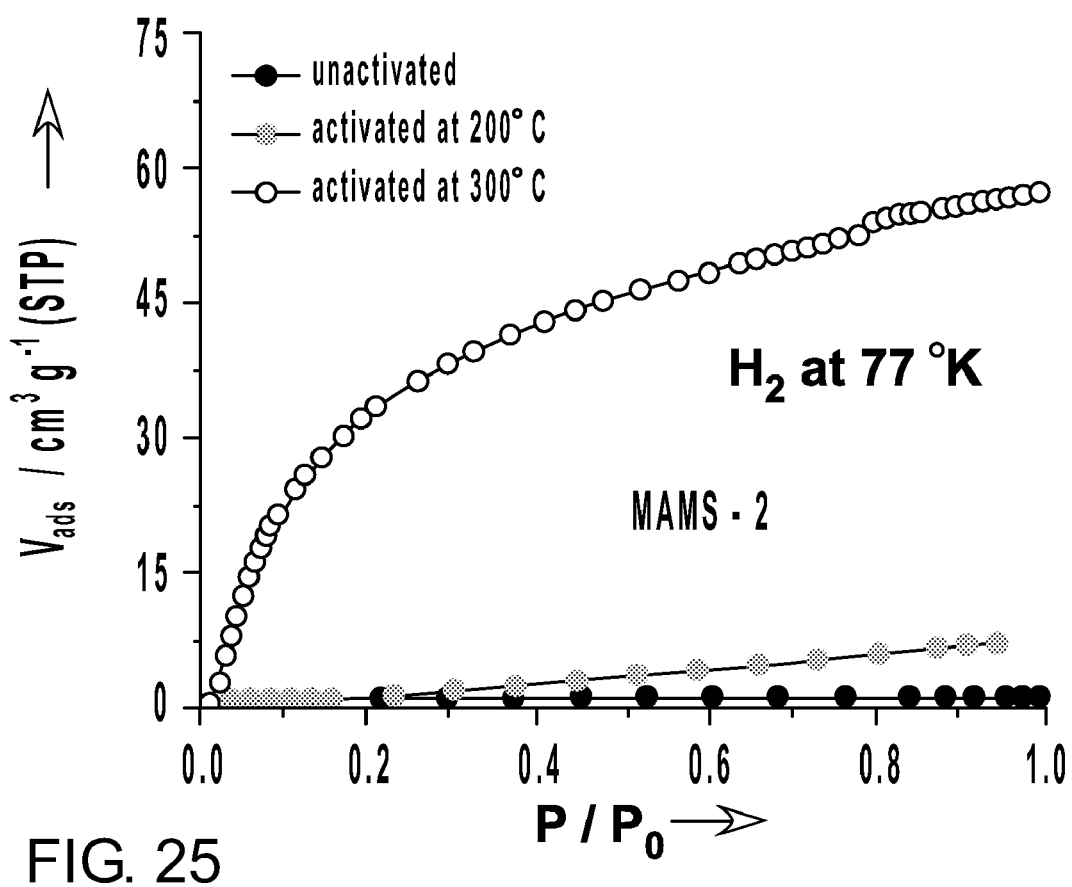
FIG. 25 illustrates $H_2$ adsorption isotherms at 77 deg. K. for fresh (solvated) $Zn_2(BBPDC)_2$, $Zn_2(BBPDC)_2$ activated at 200 deg. C., and $Zn_2(BBPDC)_2$ activated at 300 deg. C.
Figure 33:
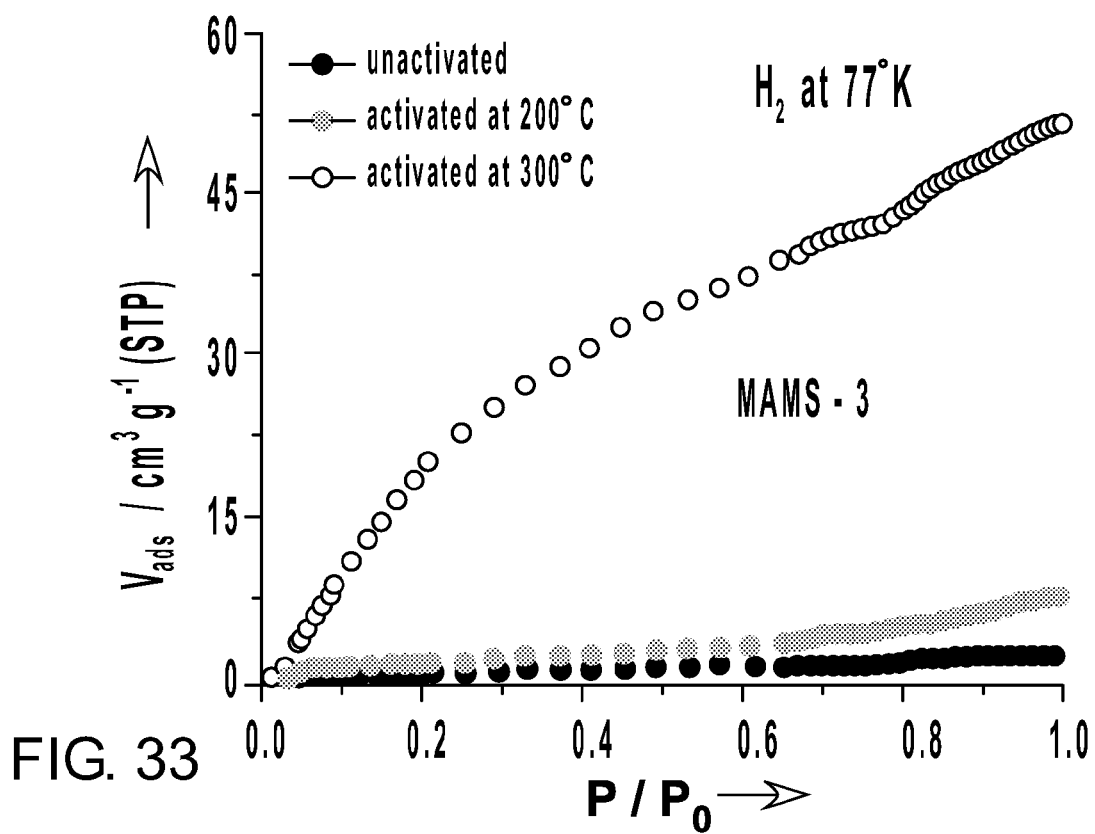
FIG. 33 shows $H_2$ adsorption isotherms at 77 deg. K. for fresh (solvated) $Co_2(BBPDC)_2$, $Co_2(BBPDC)_2$ activated at 200 deg. C., and $Co_2(BBPDC)_2$ activated at 300 deg. C.
Figure 39:
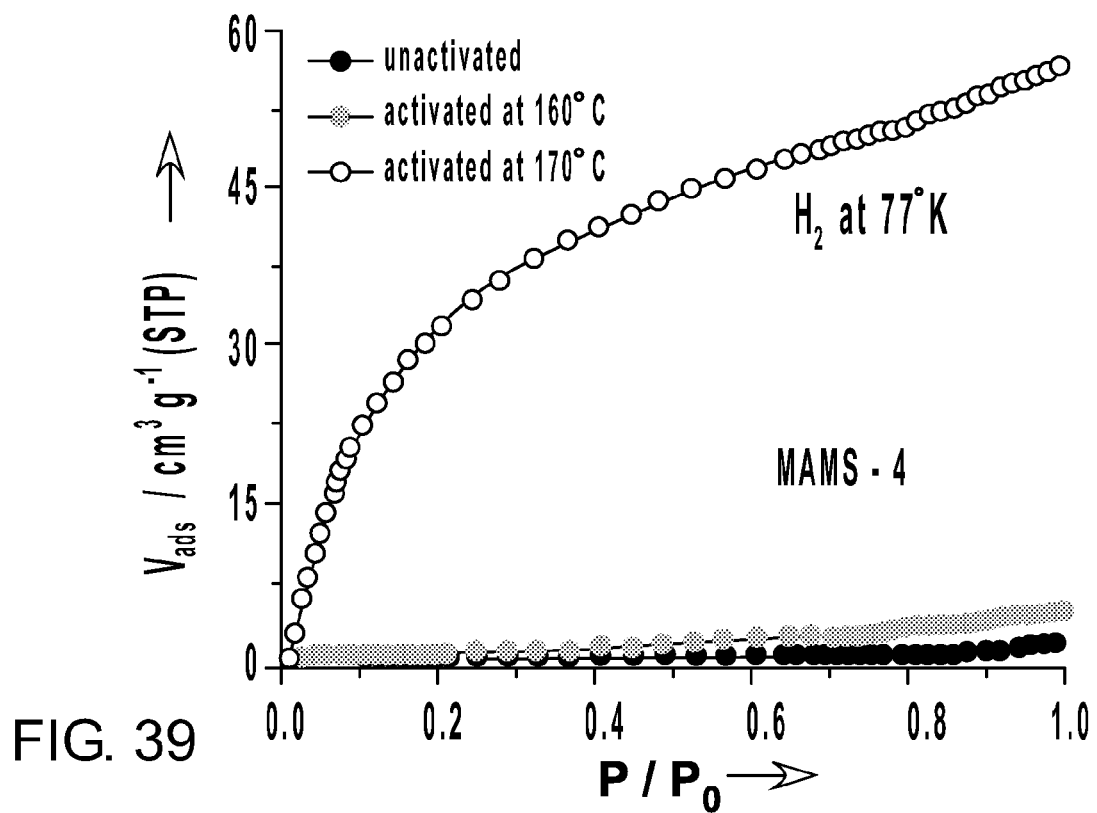
FIG. 39 shows $H_2$ adsorption isotherms at 77 deg. K. for fresh (solvated) $Cu_2(BBPDC)_2$, $Cu_2(BBPDC)_2$ activated at 160 deg. C., and $Cu_2(BBPDC)_2$ activated at 170 deg. C.

As freshly synthesized and isolated, temperature-adjustable pore size molecular sieves are solvated and are not active for adsorption. This is shown conceptually in FIG. 2a for non-activated temperature-adjustable pore size molecular sieves and in FIGS. 2b and 2c for activated temperature-adjustable pore size molecular sieves. FIGS. 3a and 3b illustrate the presence and absence, respectively, of solvate compounds. Heating to a sufficient temperature is necessary to de-solvate the temperature-adjustable pore size molecular sieves as shown, by example, for $Ni_8(\mu_3\text{-OH})_4(BBDC)_6$ in FIGS. 12-14. A thermogravimetric analysis of $Ni_8(\mu_3\text{-OH})_4(BBDC)_6$, for example, revealed a loss of eight guest water molecules from 50 deg. C. to 120 deg. C. and the release of eight bound aqua ligands per formula unit when heated to 250 deg. C. (FIG. 10). Examples for other synthesized temperature-adjustable pore size molecular sieves are shown in FIGS. 25, 33, and 39.

Figure 9A:
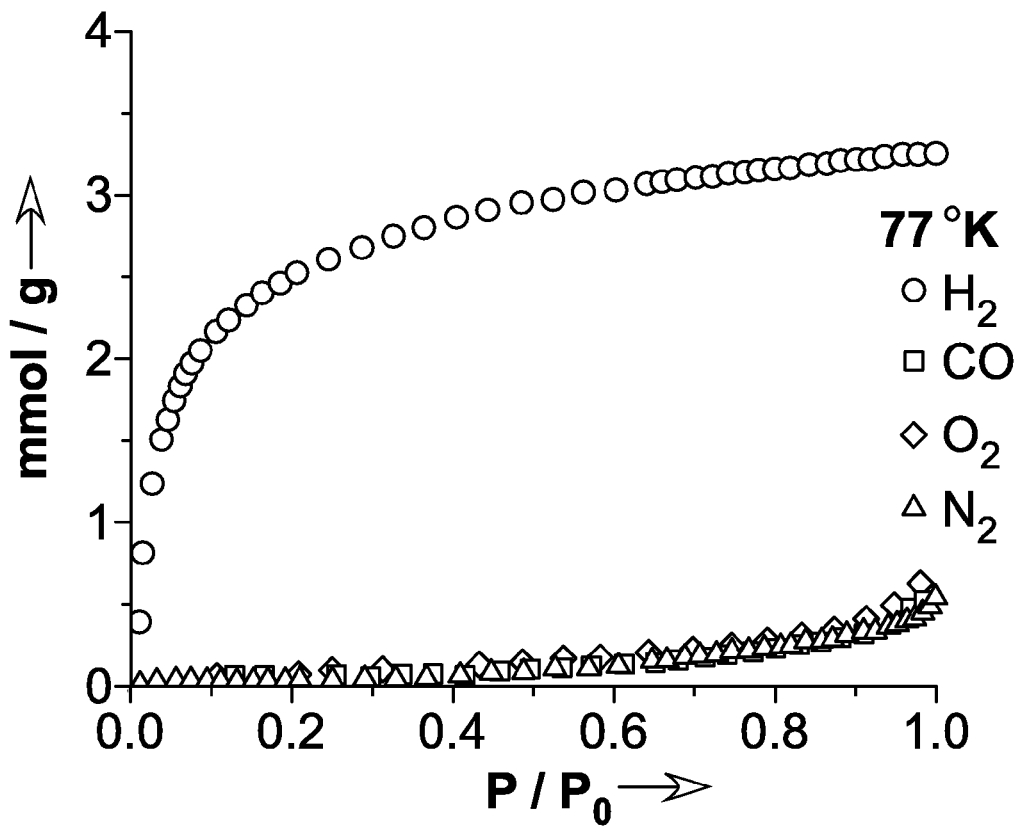
FIGS. 9a-9f are gas adsorption isotherms for selected molecular species mixtures at selected temperatures for $Ni_8(\mu_3\text{-}OH)_4(BBDC)_6$.
Figure 34:
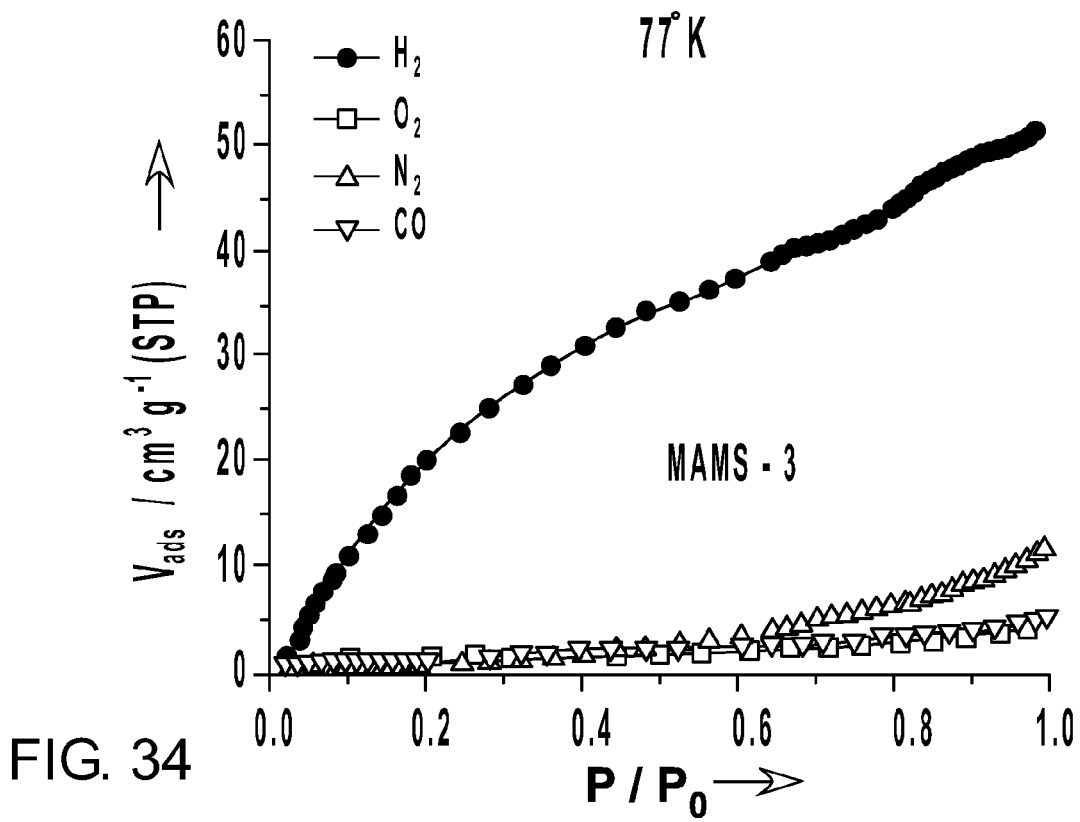
FIGS. 34-38 are gas adsorption isotherms for selected molecular species mixtures at selected temperatures for $Co_2(BBPDC)_2$.
Figure 35:
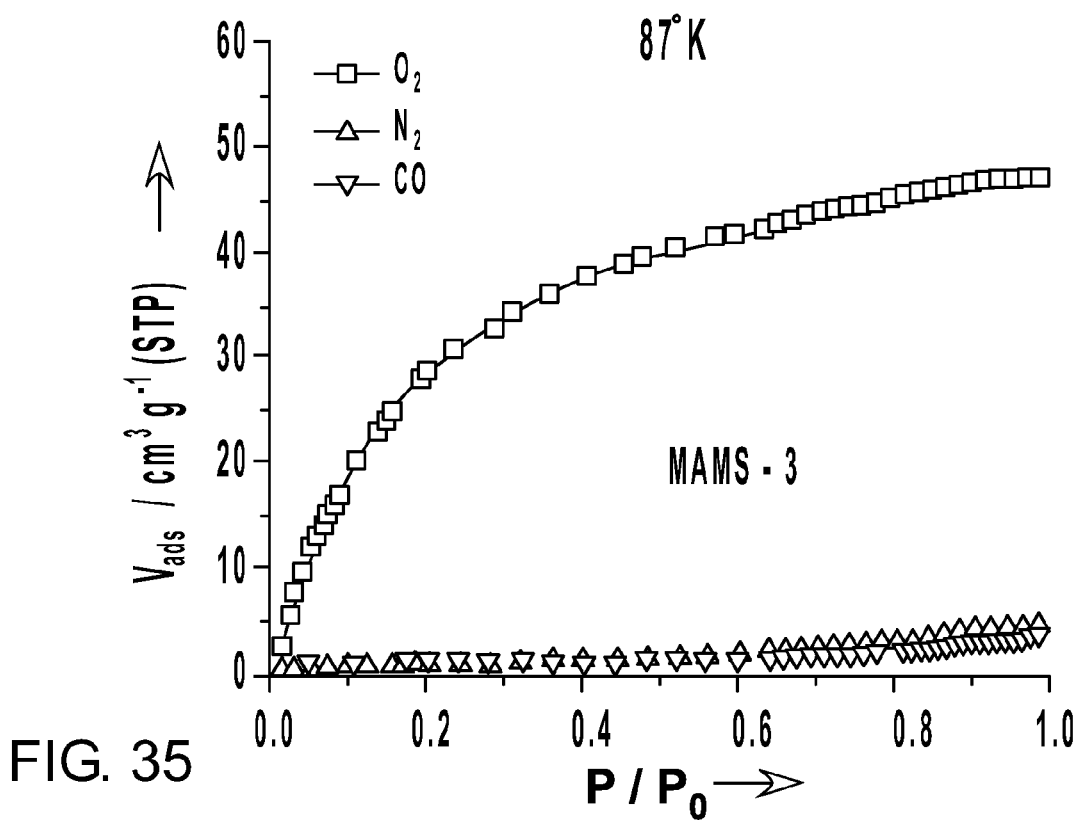
Figure 36:
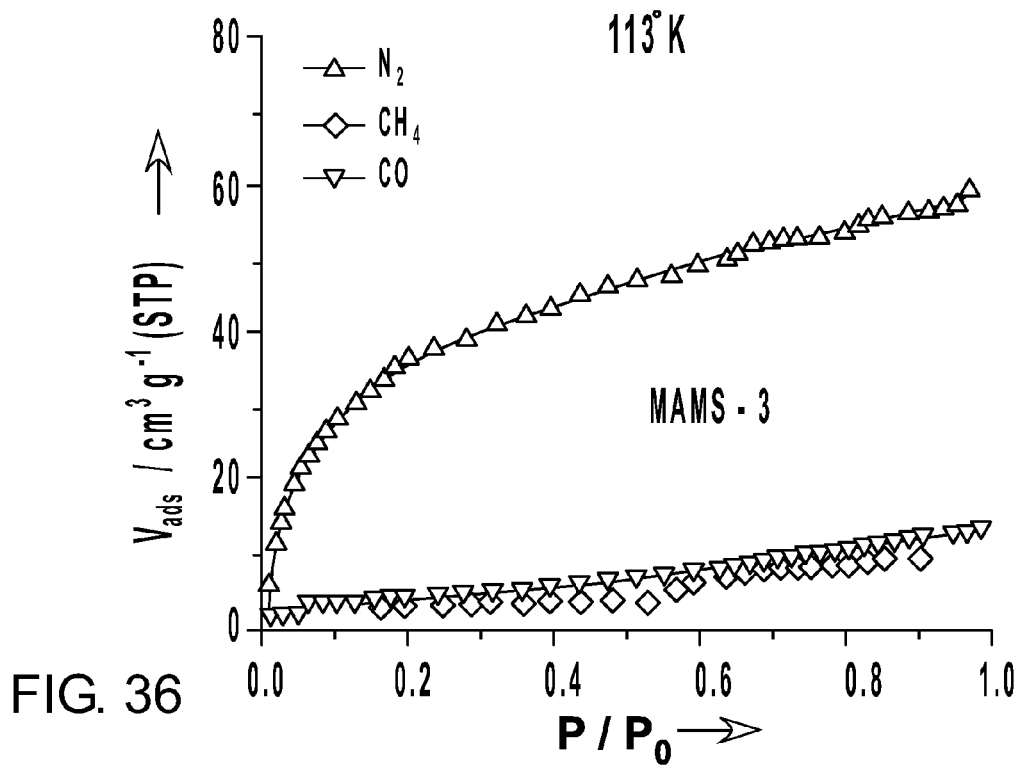
Figure 37:
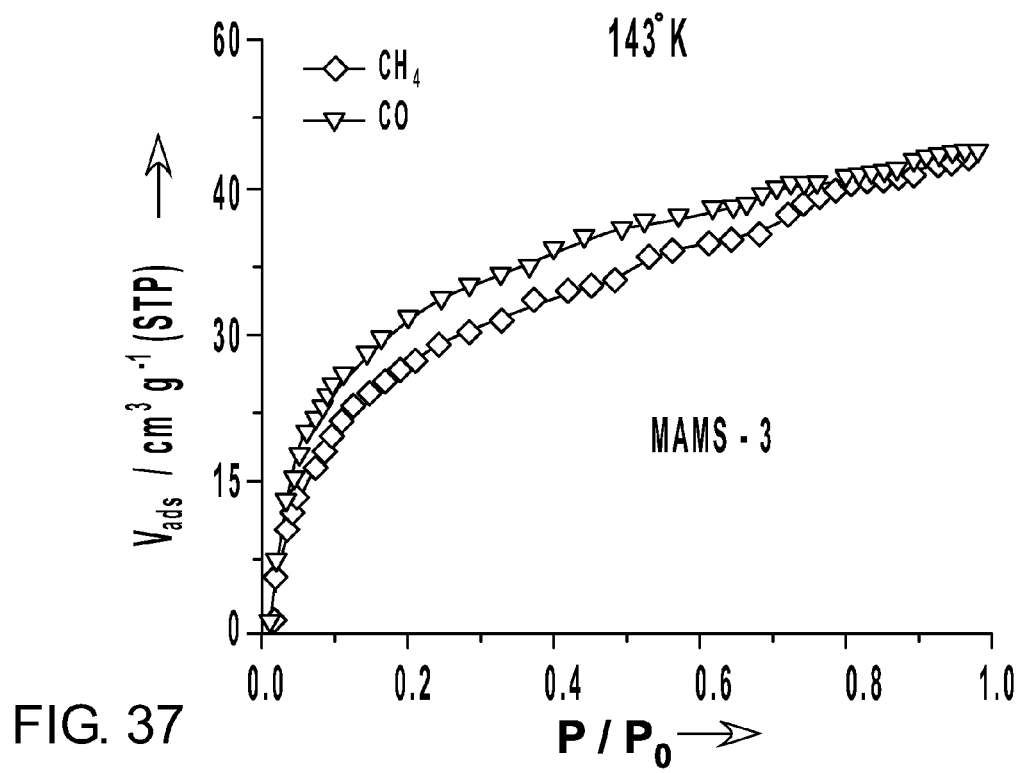
Figure 38:
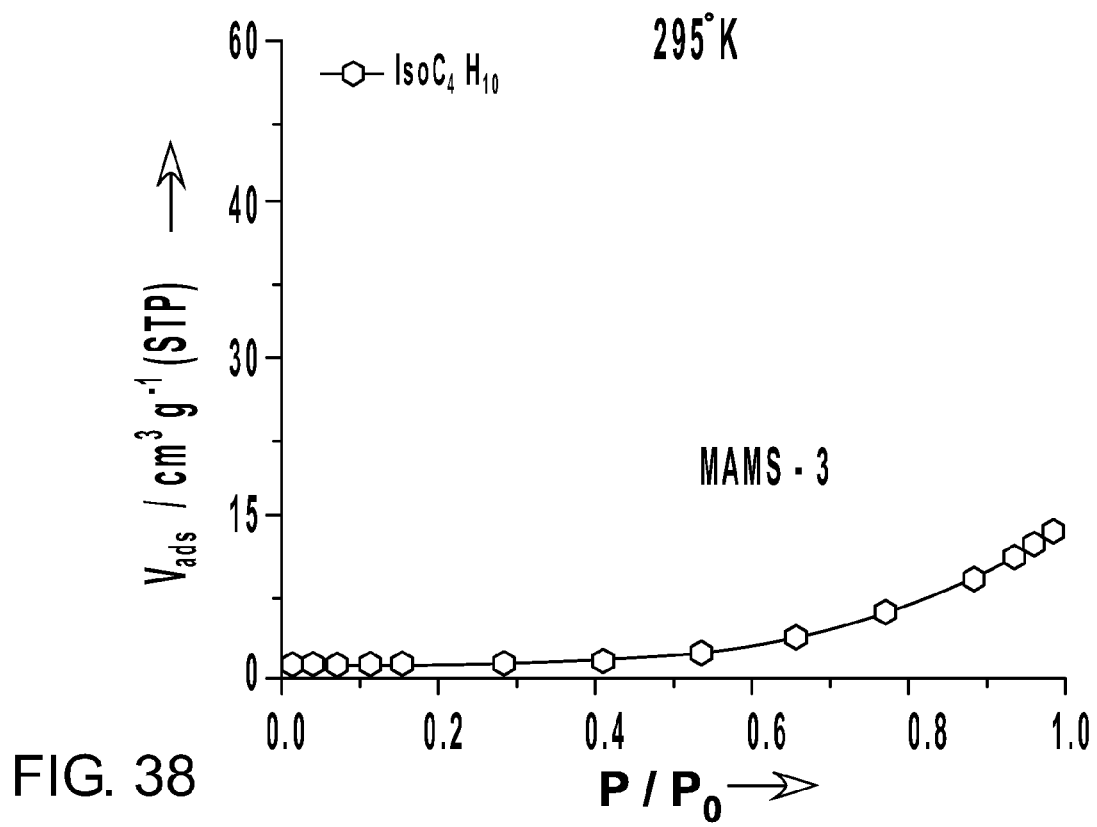
Figure 40:
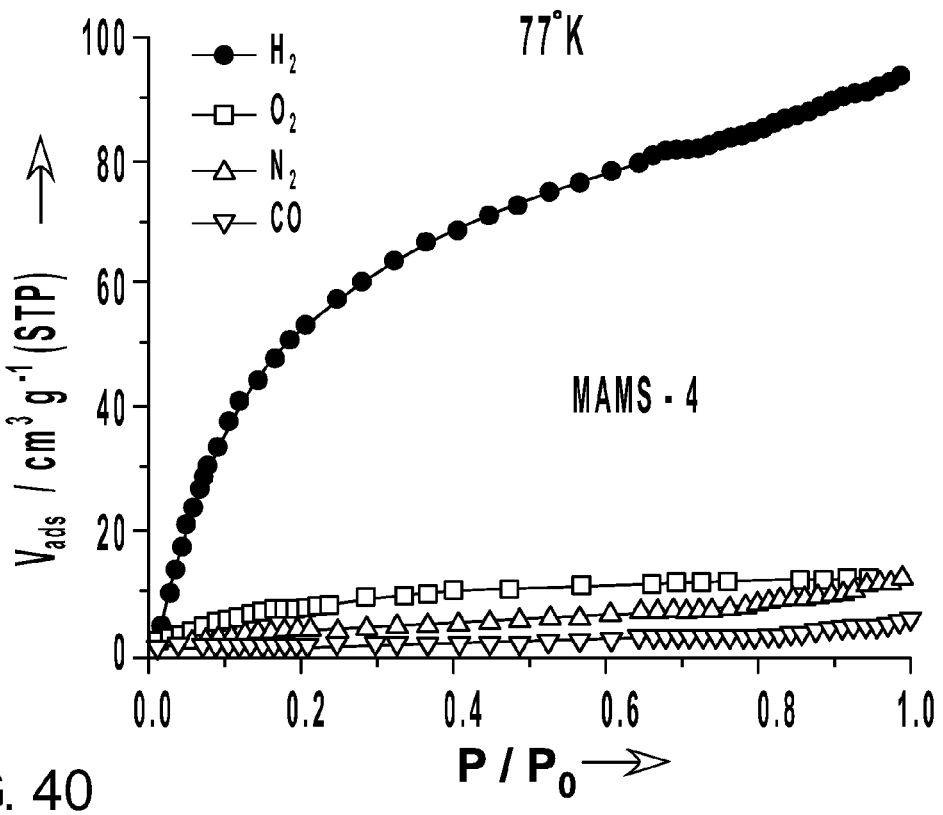
FIGS. 40-44 are gas adsorption isotherms for selected molecular species mixtures at selected temperatures for $Cu_2(BBPDC)_2$.
Figure 41:
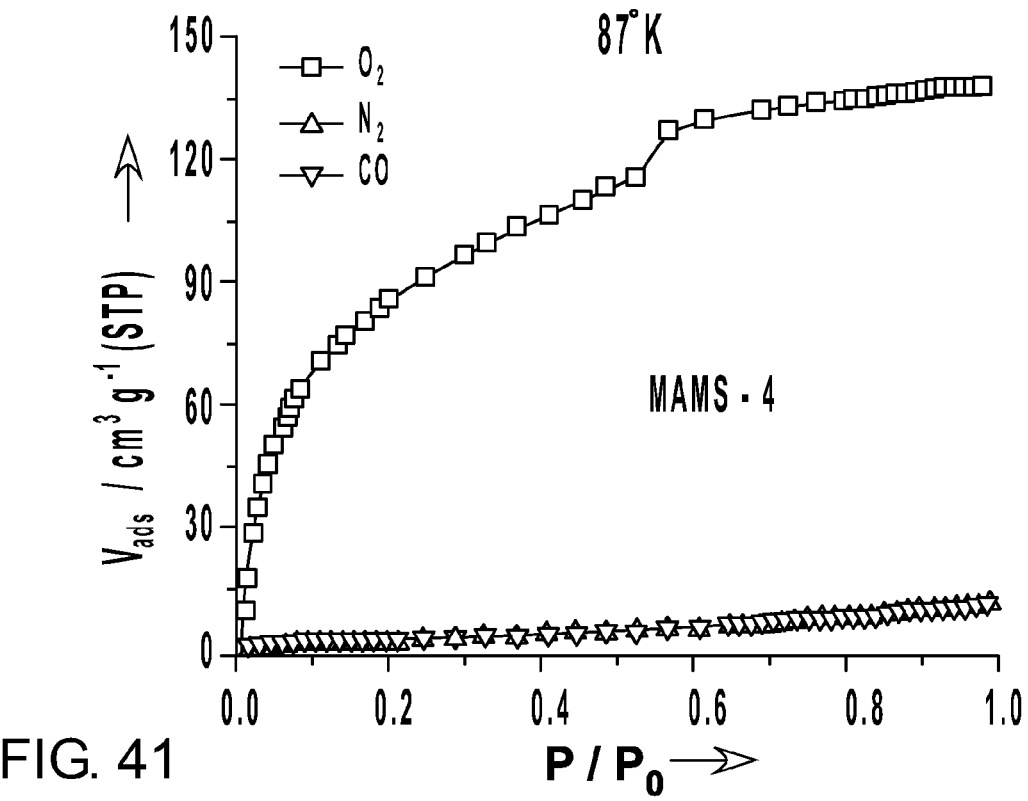
Figure 42:
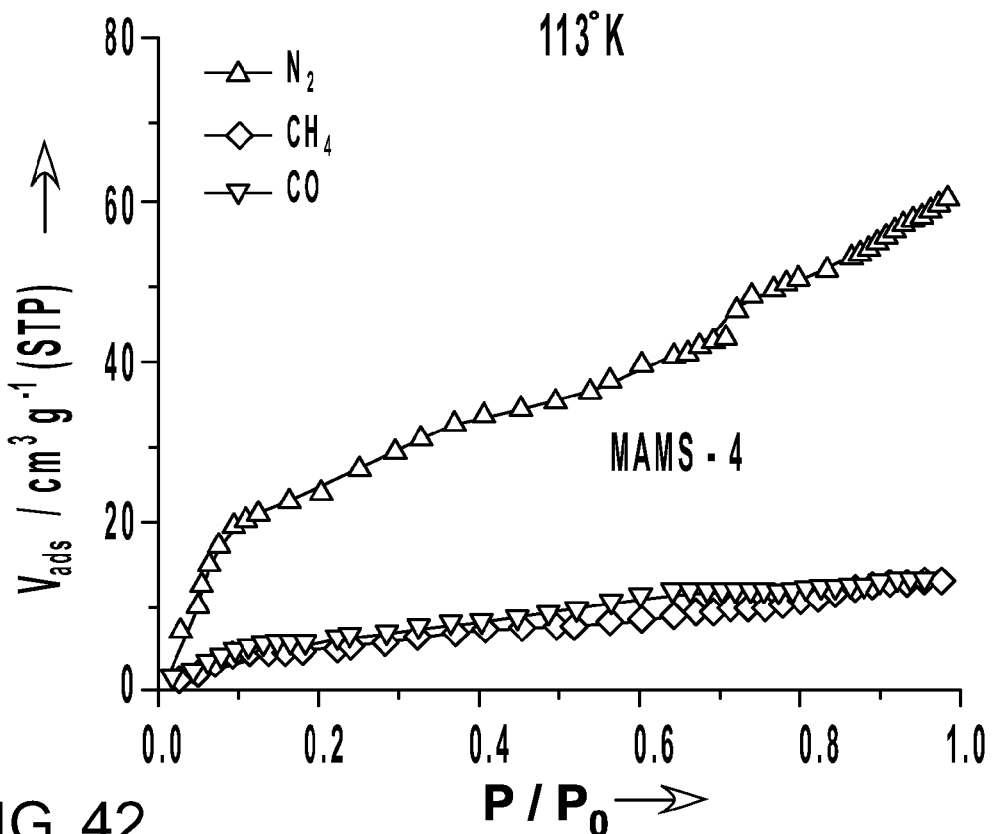
Figure 43:
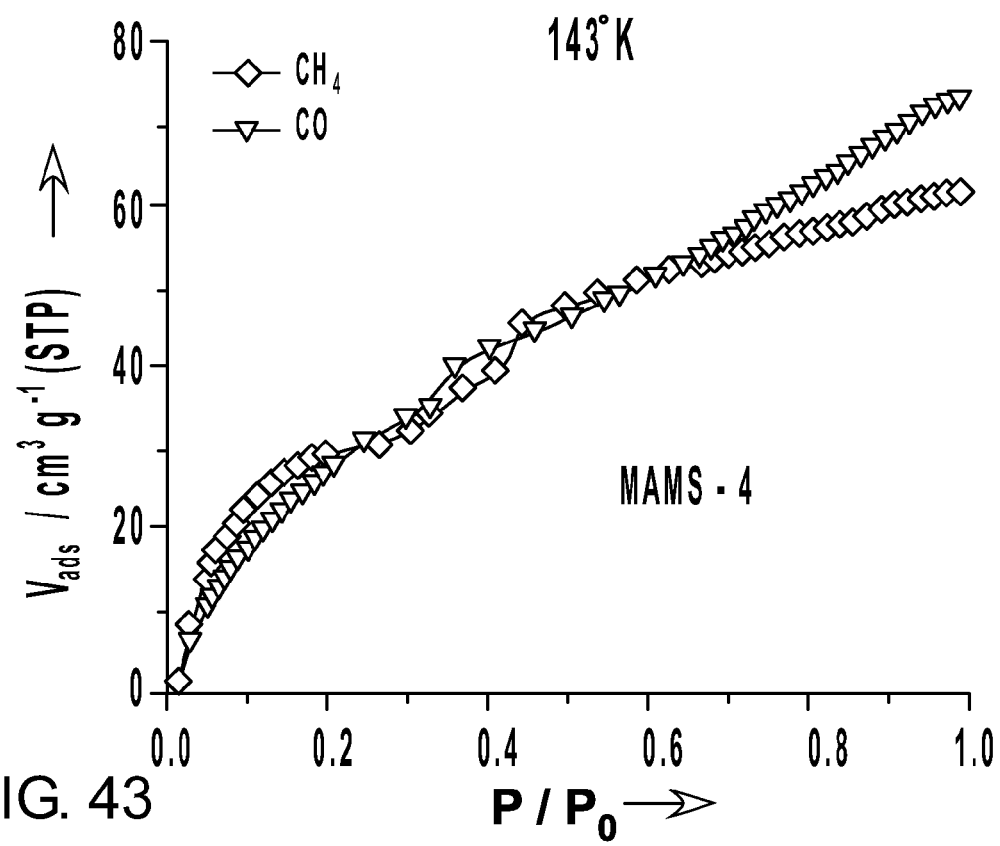
Figure 44:
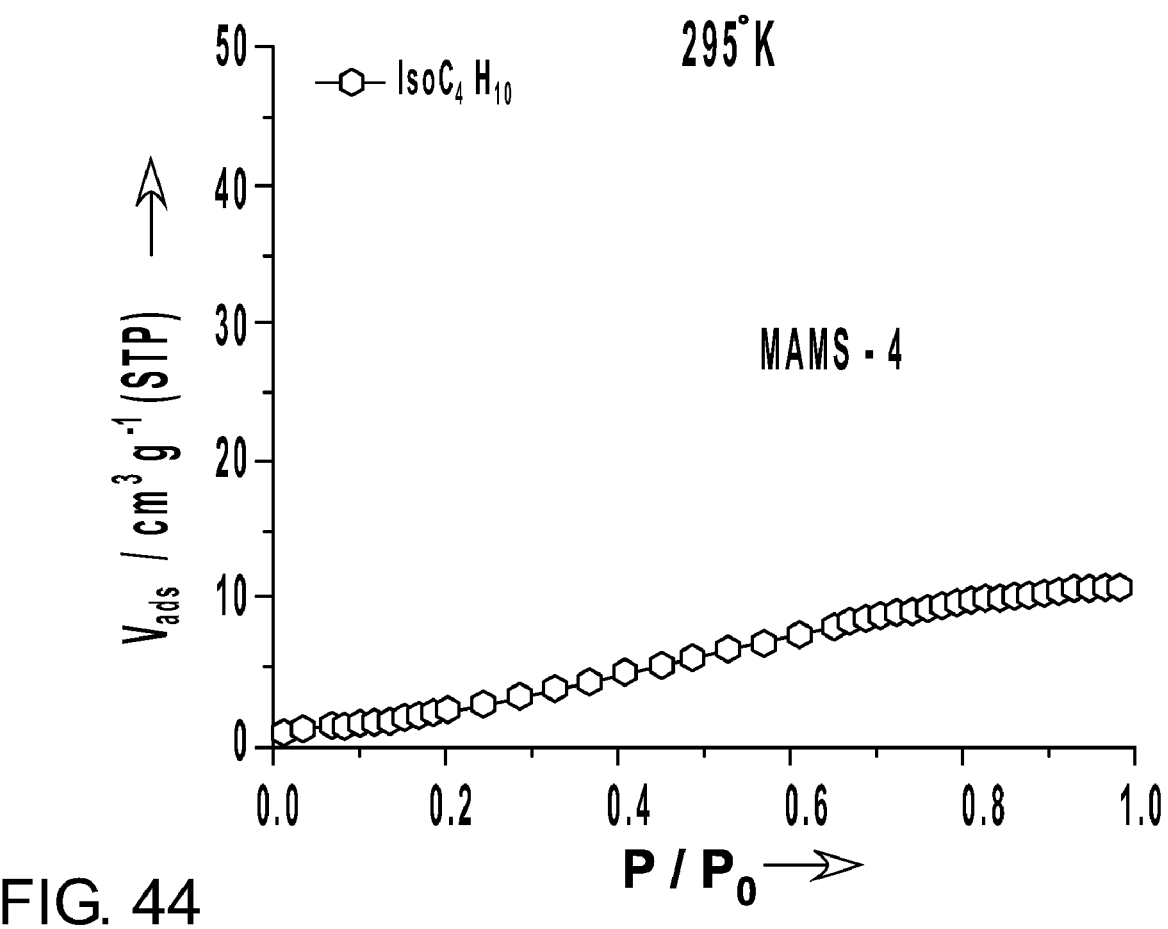

As shown in FIGS. 4a and 4b, the hydrophobic moieties 13 of the ligands 14 form temperature-adjustable pore size hydrophobic pores 26. As shown in graphical fashion in FIGS. 2a-2c, when the temperature-adjustable pore size hydrophobic pores 26 are accessible via the hydrophobic gates 27 comprising hydrophobic moieties 13, the hydrophilic pores 16 and hydrophobic chambers 18 are all connected, giving rise to a three-dimensional container with space continuity, which would account for the high uptake of selected molecular species (e.g., FIG. 9a). (See, also, FIGS. 1a, 4a, 4b, 9b-9f, 26-31, 34-36, and 40-42.) For example, in view of the kinetic diameters of $H_2$ (2.89 Å), $O_2$ (3.46 Å), $N_2$ (3.64 Å), CO (3.76 Å), one may infer the size of the temperature-adjustable pore size hydrophobic pore 26 for $Ni_8(\mu_3\text{-}OH)_4(BBDC)_6$ (described in detail below) at 77 deg. K. is between about 3.0 Å to about 3.4 Å. (FIG. 9a.) Similar results were seen with $Zn_2(BBPDC)_2$ (FIG. 26), $Co_2(BBPDC)_2$ (FIG. 34), and $Cu_2(BBPDC)_2$ (FIG. 40). The noted $Zn_2(BBPDC)_2$, $Co_2(BBPDC)_2$, and $Cu_2(BBPDC)_2$ are also described in detail below. Additional adsorption studies and results are shown in FIGS. 9b-9f, 15, 16, 26-32, 34-38, and 40-44. As described more fully below, the hydrophilic pores 16 alone appear to not be responsible for the gas uptake. In fact, they seem to account for a very minor part of the adsorption. As shown for $Ni_8(\mu_3\text{-}OH)_4(BBDC)_6$, for example, in FIG. 9a, at 77 deg. K., only $H_2$ can enter the hydrophobic chambers 18, showing significant uptake. At 77 deg. K., other molecules (CO, $O_2$, and $N_2$) cannot move beyond the hydrophilic pores 16 and the uptake of these gases is very low.

Figure 23:
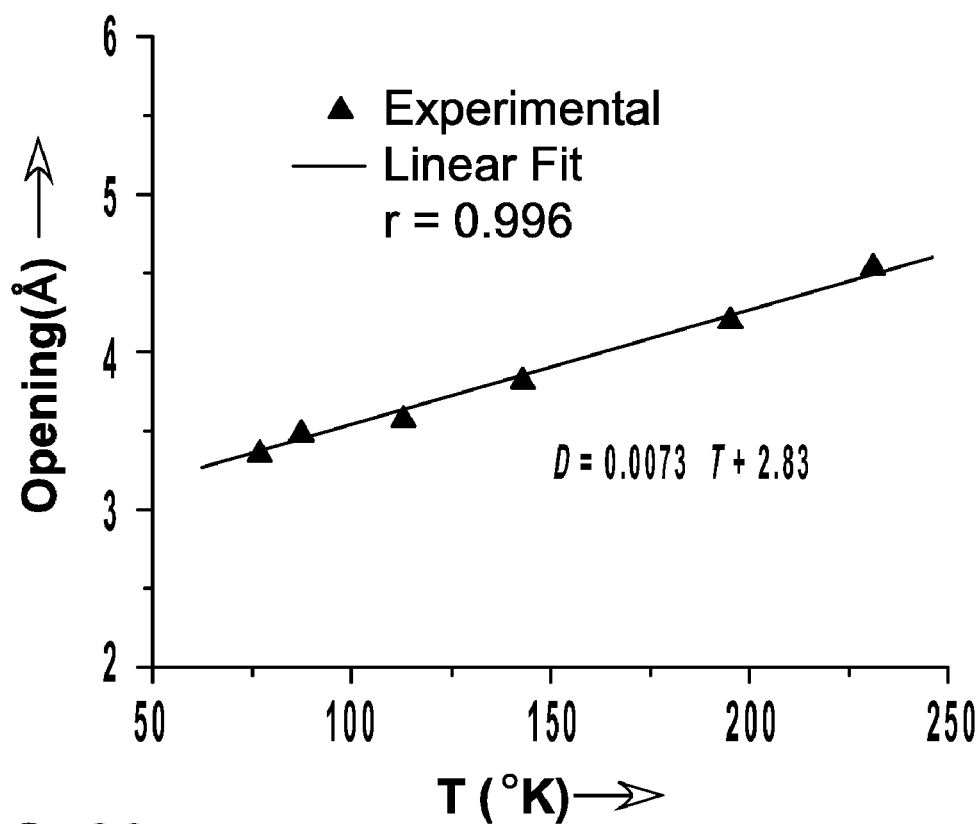
FIG. 23 illustrates the temperature-adjustable gating opening effect of $Zn_2(BBPDC)_2$, $Co_2(BBPDC)_2$, and $Cu_2(BBPDC)_2$.

In general, the temperature-adjustable molecular adsorption exhibits a temperature-adjustable pore opening 25 defined by the equation $D=D_0+\alpha T$, where D is the exhibited kinetic opening, in Angstroms, of the opening of the temperature-adjustable pore, $D_0$ is the exhibited temperature-adjustable pore opening at 0 deg. K., $\alpha$ is a constant related to the amphiphilic ligand, and T is the temperature in degrees Kelvin. (See, e.g., FIGS. 20 and 23.)

As described more fully below, and as can be seen in the accompanying figures, contacting a gaseous mixture with the composition of matter can result in selective adsorption of the gas with the smallest molecular size. For example, the following pairs of molecules may be separated: $H_2/N_2$, $H_2/CO$, $N_2/O_2$, $N_2/CH_4$, $CH_4/C_2H_4$, and $C_2H_4/C_3H_6$.

As will be appreciated by those skilled in the art, it is likely that the gate effect is not just the result of thermal vibration of the hydrophobic moiety 13 alone as the other portions of the molecular structure, particularly the phenyl ring, for example, will also contribute somewhat. When the temperature is precisely controlled, any effect within this range can be accurately attained. This size range covers almost all commercially-important gas separations. For example, $H_2/N_2$, $H_2/CO$, $N_2/O_2$, $N_2/CH_4$, $CH_4/C_2H_4$ and $C_2H_4/C_3H_6$, wherein the molecules are separated from their respective pair. Exemplary kinetic diameters include $H_2$ (2.89 Å), $O_2$ (3.46 Å), $N_2$ (3.64 Å), CO (3.76 Å), $CH_4$ (3.8 Å), $C_2H_4$, (3.8 Å), $C_3H_6$, (4.5 Å), and $SF_6$ (5.5 Å).

In operation, gas molecules enter the hydrophobic chambers 18 through the hydrophilic pores 16 and temperature-adjustable pore size hydrophobic pores 26. (FIGS. 1a, 1b, and 2a-2c.) It has been found, for example, that when the kinetic diameter of the gas molecule (e.g., $SF_6$ at 5.5 Å) exceeds the size of the hydrophilic pores 16 (5.0 Å considering van der Waals radii), no meaningful uptake was observed in an adsorption study. (FIGS. 2a-2c and 16.) The upper limit of the hydrophilic pore 16 is also consistent with an adsorption study on iso-$C_4H_{10}$ (5.0 Å) which entered $Ni_8(\mu_3\text{-}OH)_4(BBDC)_6$ at room temperature (295 deg. K.). See FIG. 16.

Figure 20:
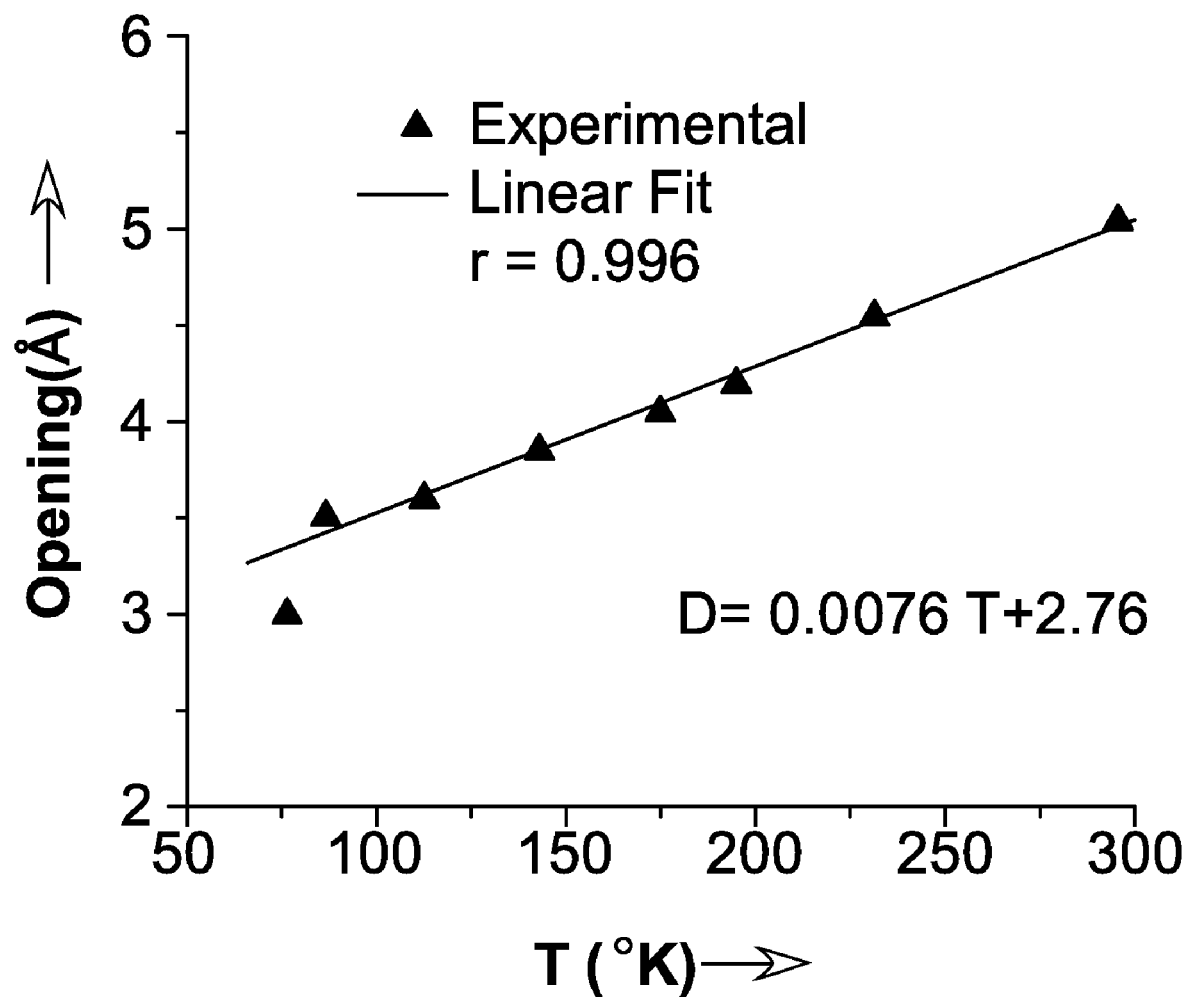
FIG. 20 illustrates the temperature-adjustable gating effect of $Ni_8(\mu_3\text{-}OH)_4(BBDC)_6$.
Figure 21:
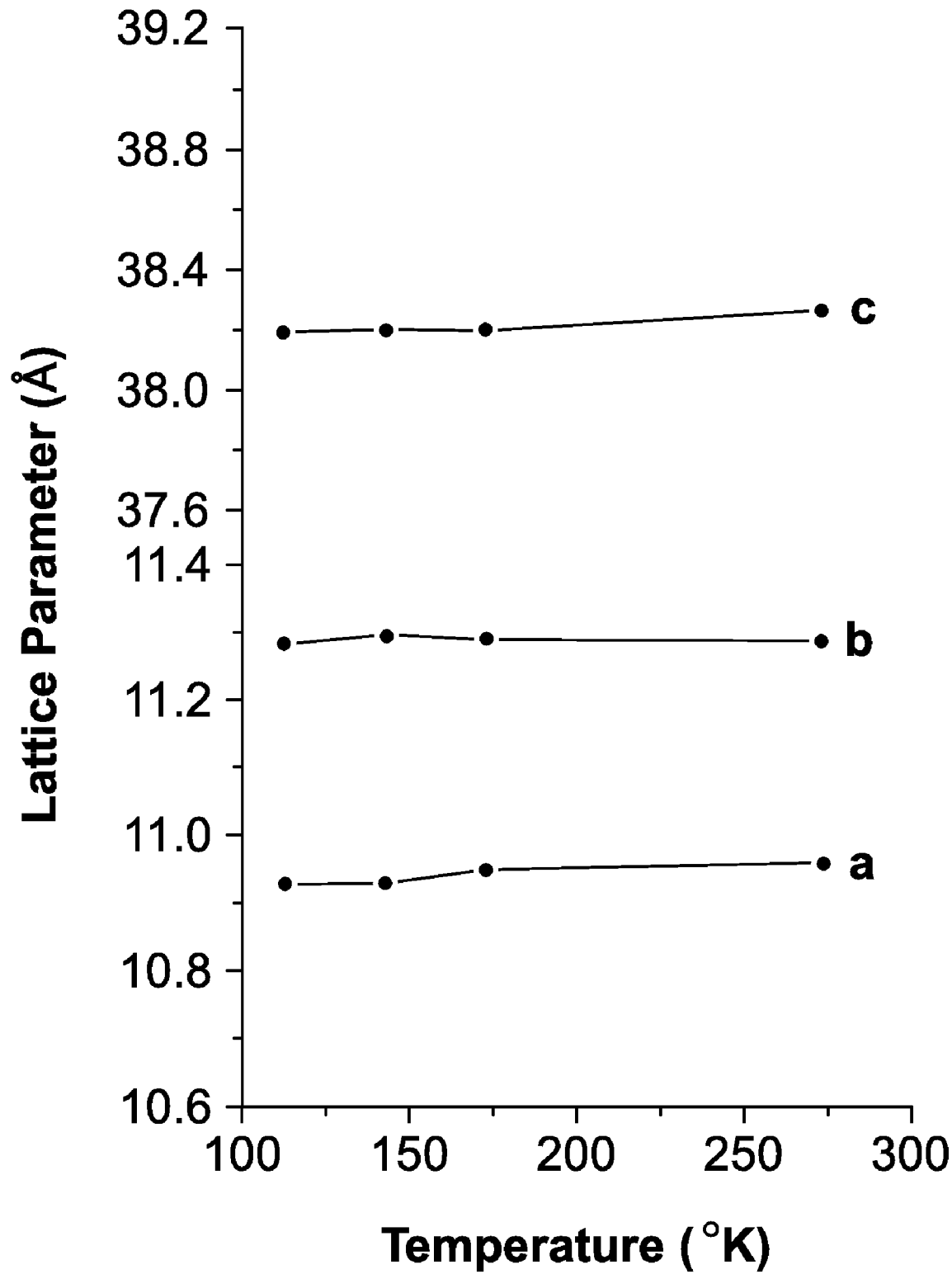
FIG. 21 illustrates cell various lattice parameters at different temperatures for $Ni_8(\mu_3\text{-}OH)_4(BBDC)_6$.

The temperature-adjustable molecular-gating effect does not appear to arise from simple thermal expansion of the framework of the temperature-adjustable pore size molecular sieve 10. As shown in FIG. 21, for example, the lattice size parameters for $Ni_8(\mu_3\text{-}OH)_4(BBDC)_6$ 10 show virtually no response to temperature over a wide range. (See, also, FIG. 24.) The opening 25 of the temperature-adjustable pore size hydrophobic pore 26 appears to be controlled by the amplitude of thermal vibration of the hydrophobic moieties 13. FIG. 20, for example, shows temperature versus size of the molecule allowed to pass through the opening for $Ni_8(\mu_3\text{-}OH)_4(BBDC)_6$. (See, also, FIG. 23.) The data point in FIG. 20 at 77 deg. K. gives an under-estimation of the opening because a gas molecule with a size between 2.89 Å ($H_2$) and 3.40 Å (Ar) is not available for gas adsorption studies. Ignoring the point at 77 deg. K., the temperature-adjustable pore size hydrophobic pore opening D in Angstroms, and temperature T deg. K., can be related by a linear equation $$D=0.0076T+2.76,$$

with a correlation coefficient of 0.996. This equation can be used to predict if a gas molecule will be able to enter the hydrophobic chamber 18 at a certain temperature. It may also be used to find the best temperature for the separation of a mixture. More generally, the linear relationship between temperature-adjustable pore size and temperature can be represented as $$D=D_0+\alpha T,$$

where D is the exhibited kinetic opening, in Angstroms (Å) at temperature T (deg. K.), $D_0$ is the exhibited temperature-adjustable pore opening in Angstroms at 0 deg. K., and $\alpha$ is a constant.

In synthesizing a MOF-based temperature-adjustable pore size molecular sieve 10, a source of metal ions and a source of amphiphilic ligands 14 (FIGS. 8a-8e), each ligand comprising a functionalized hydrophobic moiety 14 and a functionalized hydrophilic moiety (FIGS. 8a-8e), are mixed together in a suitable solvent. The mixture is then heated to a first temperature, optionally at a first heating rate, held at the first temperature for a suitable length of time, and cooled to a second temperature. Suitable solvents include, but are not limited to, $H_2O$/ethylene glycol, dimethyl sulfoxide (DMSO), dimethylacetamide (DMA), and dimethylformamide (DMF). First temperatures range, for example, between 75 deg. C to 210 deg. C. Suitable hold temperatures range, for example, between 18 hours and 24 hours. After washing, the fresh (solvated) temperature-adjustable pore size molecular sieves are activated by suitable heating and pressure to remove guest solvent molecules and bound solvent molecules. See, e.g., FIGS. 12, 13, 25, 33, and 39.

Solvothermal reactions of the amphiphilic ligand 4'-tert-butyl-biphenyl-3,5-dicarboxylate (BBPDC) with transition metals zinc ($Zn(NO_3)_2$), cobalt ($Co(NO_3)_2$), and copper (Cu $(NO_3)_2$ gave di-metal-cluster-based compounds designated, for convenience, $Zn_2(BBPDC)_2$, $Co_2(BBPDC)_2$, and $Cu_2(BBPDC)_2$, respectively. These three temperature-adjustable pore size molecular sieves are isostructural and all exhibit temperature-adjustable pore size molecular sieving effects. As compared with the amphiphilic ligand used for $Ni_8(\mu_3\text{-}OH)_4(BBDC)_6$ (BBDC), the ligand used for $Zn_2(BBPDC)_2$, $Co_2(BBPDC)_2$ and $Cu_2(BBPDC)_2$ (BBPDC) is characterized by an additional phenyl group. See FIGS. 8a and 8e.

The referenced three BBPDC-based temperature-adjustable pore size molecular sieves adopt the $[M_2][(COO)_4]$ paddle-wheel structure shown conceptually in FIG. 5. The two aqua axial elements are removed at a high activation temperature.

Figure 47:
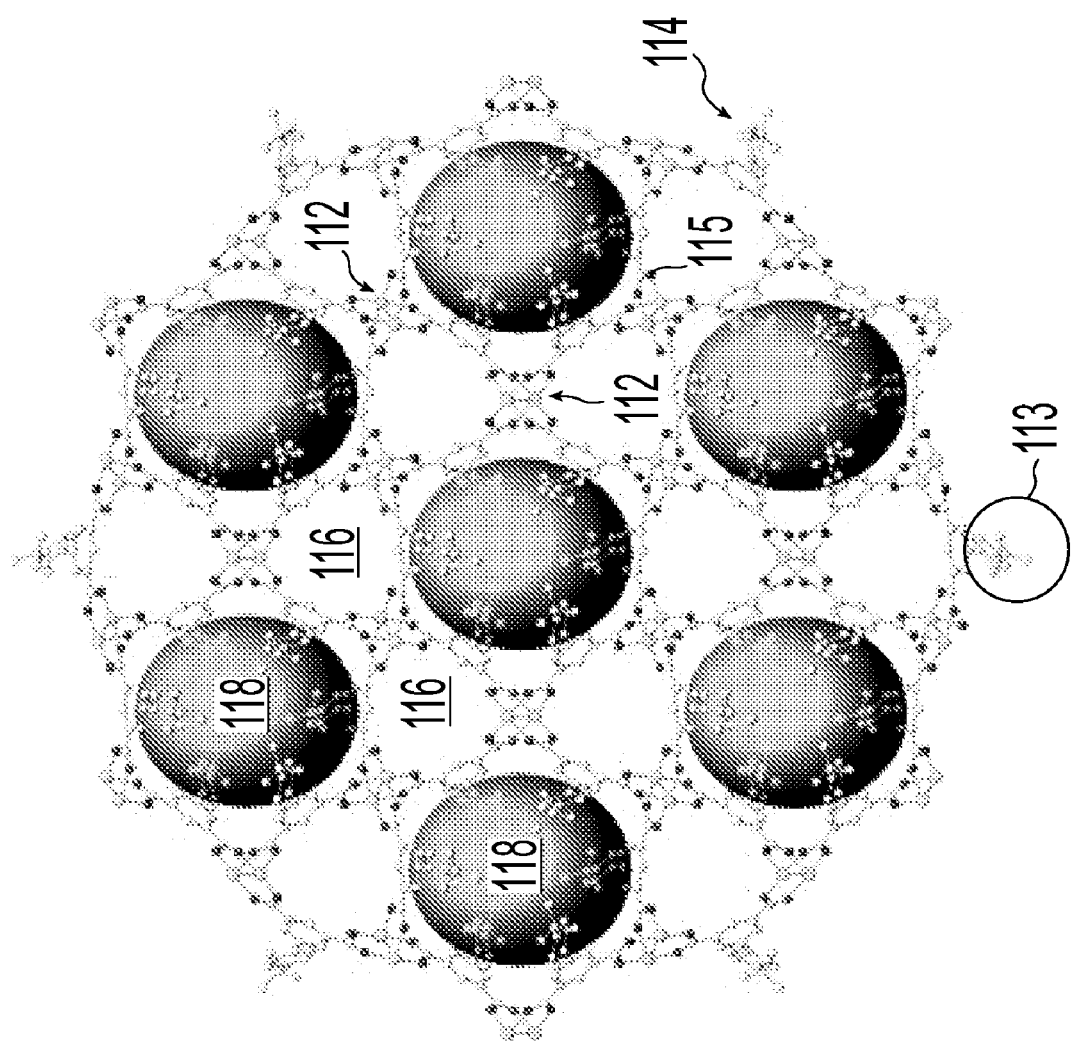
FIGS. 47-50 are three-dimensional graphical renditions of portions of $M_2((CH_3)_3CC_6H_4C_6H_3(CO_2)_2)_2$. wherein M is zinc, cobalt, or copper and $(CH_3)_3CC_6H_4C_6H_3(CO_2)_2$ is the molecular formula for 4'-tert-butyl-biphenyl-3,5-dicarboxylate (BBPDC).
Figure 48:
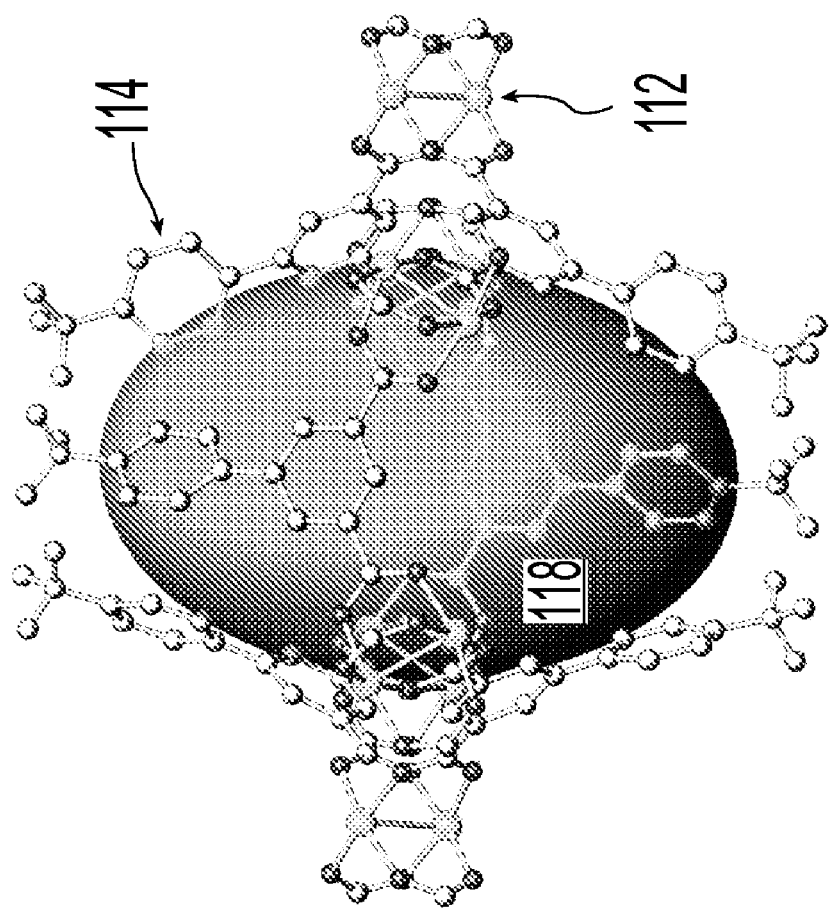
Figure 49:
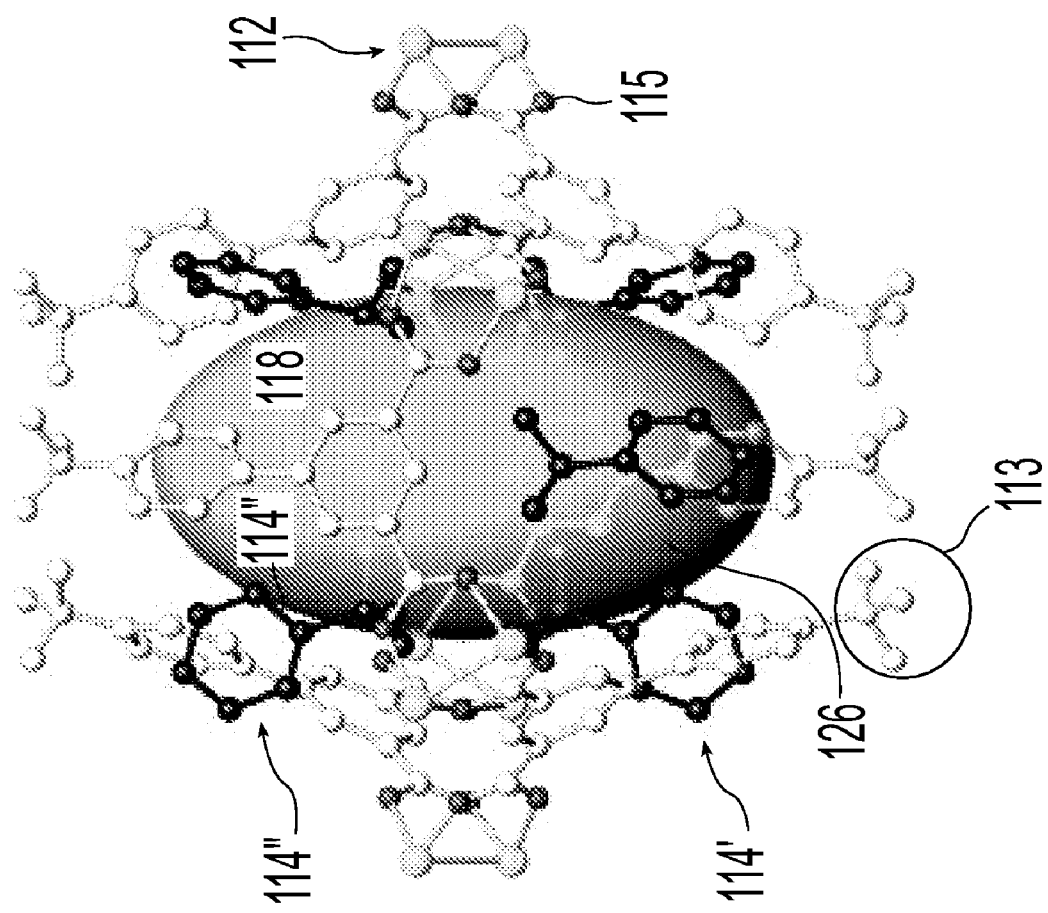
Figure 50:
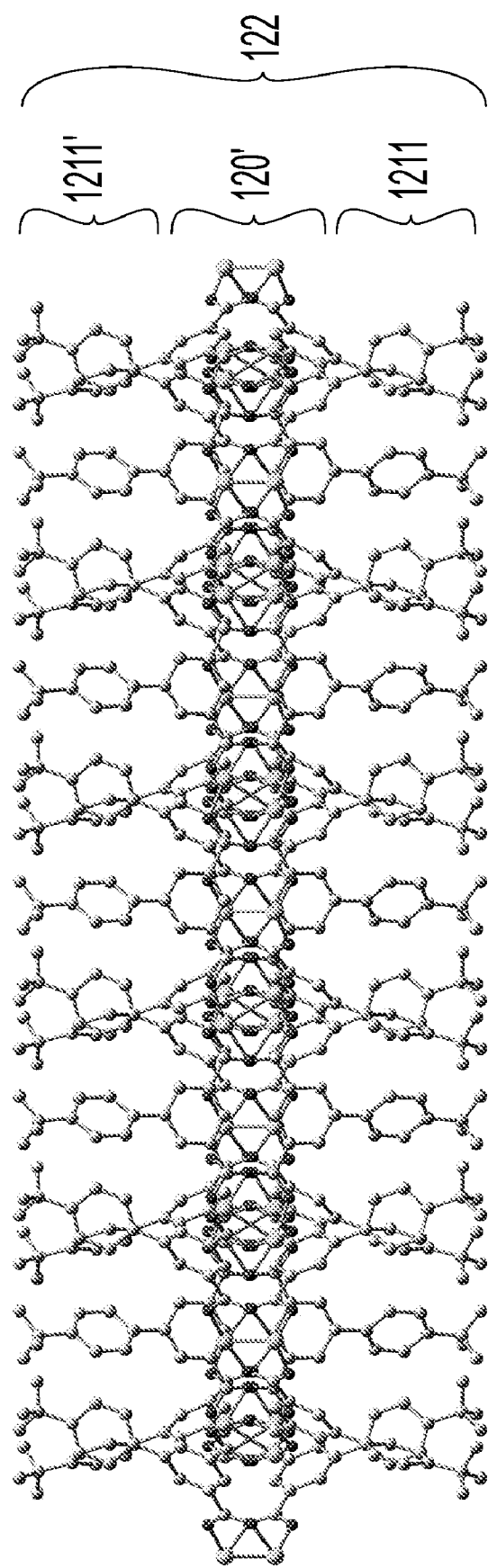

Each di-metal cluster 112 connects with four BBPDC ligands 114 through their hydrophilic moiety carboxylates 115 and each BBDC ligand 114, through its hydrophilic moiety carboxylates 115 connects with two di-metal clusters 112. As with $Ni_8(\mu_3\text{-OH})_4(BBDC)_6$, and as shown in FIG. 50, the di-metal cluster-BBPDC combination expands into a two-dimensional layer 112 with the di-metal cluster layer 1201 sandwiched by two BBPDC ligand layers 1211, 1211'. As shown in FIG. 47, in each layer, every three di-metal clusters 112 are connected by three BBPDC ligands 114 to form generally triangular hydrophilic pores 116 with the tert-butyl groups of every three BBDC ligands 114 pointing alternately in alternate directions. Every six di-metal clusters 112 connect with six BBPDC ligands 114, three of which point generally in one direction and three of which point generally in the opposite direction to form a hydrophobic chamber 118. The volume of the hydrophobic chamber 118 for $Zn_2(BBPDC)_2$ was 1360 Å$^3$, for $Co_2(BBPDC)_2$, 1386 Å$^3$, and for $Cu_2(BBPDC)_2$ 1341 Å$^3$. As shown in FIG. 47, every hydrophobic chamber 118 with six-fold symmetry is encircled by six hydrophilic pores 116, and each hydrophilic pore 116 is surrounded by six hydrophobic chambers 118. In each hydrophobic chamber 118, there are six windows with the opening size of 9.709 Å (atom-to-atom distance) (ca. 6.6 Å when considering van der Waals radii) for $Zn_2(BBPDC)_2$. For $Co_2(BBPDC)_2$, 9.869 Å and ca. 6.8 Å. And, for $Cu_2(BBPDC)_2$, 6.600 Å and ca. 6.5 Å. Every layer connects with adjacent layers through the van der Waals interactions between tert-butyl groups. The triangular hydrophilic pores 116 of each layer pack along the c-direction to form a one-dimensional channel hydrophilic pore 116 with an edge length of 7.822 Å for $Zn_2(BBPDC)_2$, 8.073 Å for $Co_2(BBPDC)_2$, and 7.905 Å for $Cu_2(BBPDC)_2$. Metal atom-to-metal atom distances are ca. 4.9 Å for $Zn_2(BBPDC)_2$, ca. 4.8 Å for $Co_2(BBPDC)_2$, and ca. 4.9 Å for $Cu_2(BBPDC)_2$ when considering van der Waals radii. As shown in FIG. 49, the hydrophobic chambers 118 of each layer pack along the c-direction with the hydrophobic moieties 114', 114" from other layers inserting in the windows of the hydrophobic chambers 118. It can be inferred that the hydrophobic chambers 118 should be the main storage space for gas molecules, while the hydrophilic pores 116 should act as passages to allow the gas molecules to pass into the hydrophobic chambers 118 through the hydrophobic moieties 113. These hydrophobic moieties 113 may effect the observed selective uptake.

Figure 24:
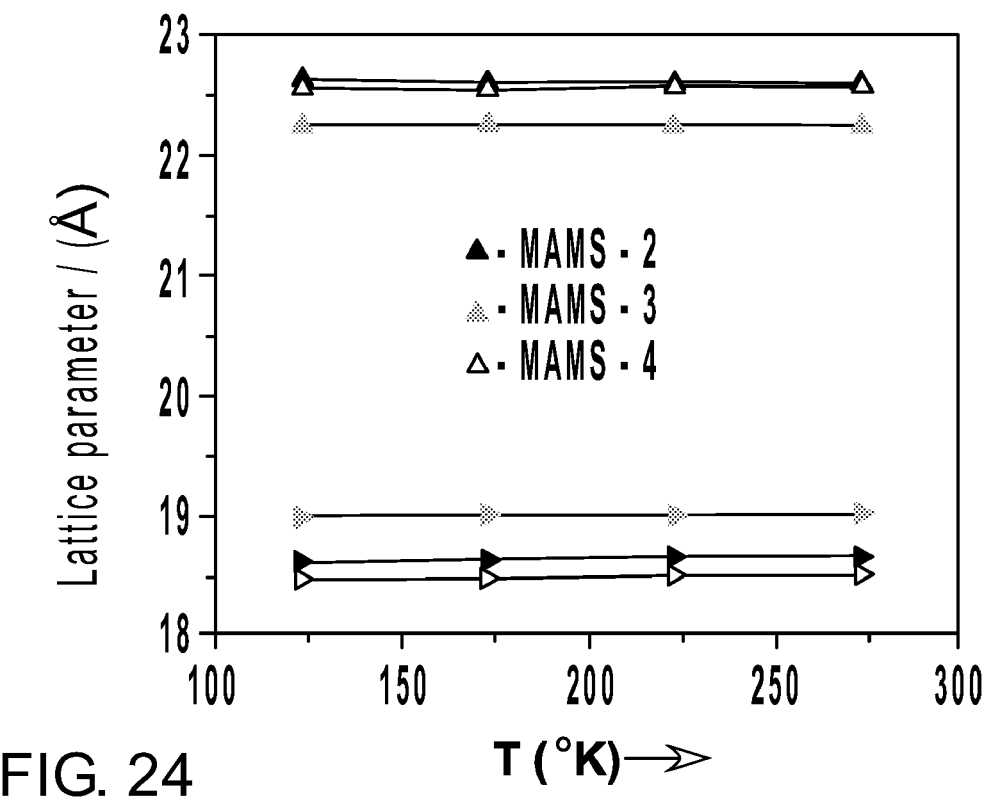
FIG. 24 illustrates various lattice parameters at different temperatures for $Zn_2(BBPDC)_2$, $Co_2(BBPDC)_2$, and $Cu_2(BBPDC)_2$.
Figure 45:
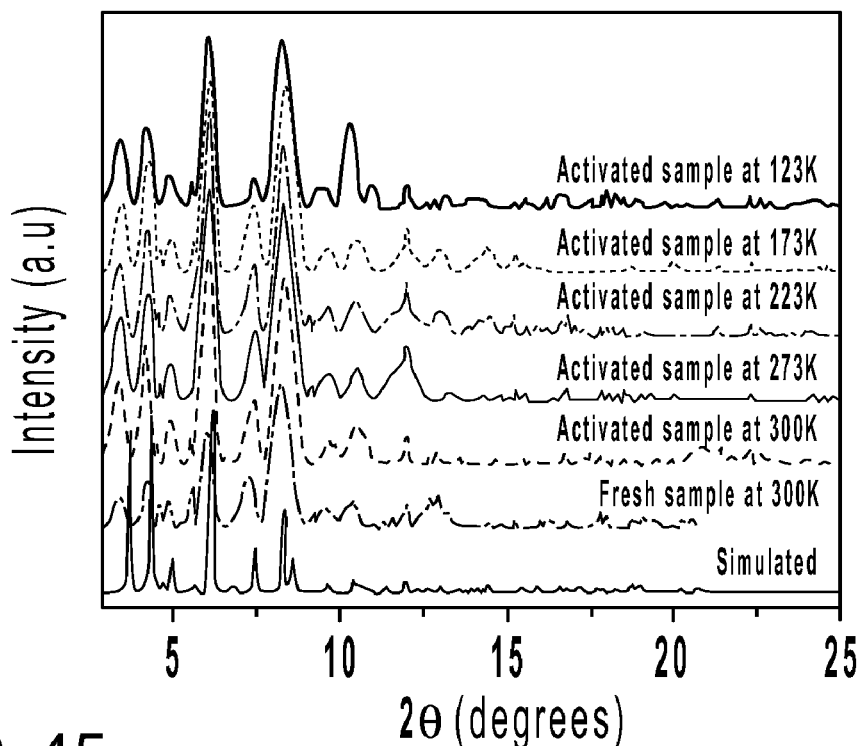
FIG. 45 shows X-ray powder diffraction patterns for fresh $Co_2(BBPDC)_2$ and $Co_2(BBPDC)_2$ activated at various temperatures.
Figure 46:
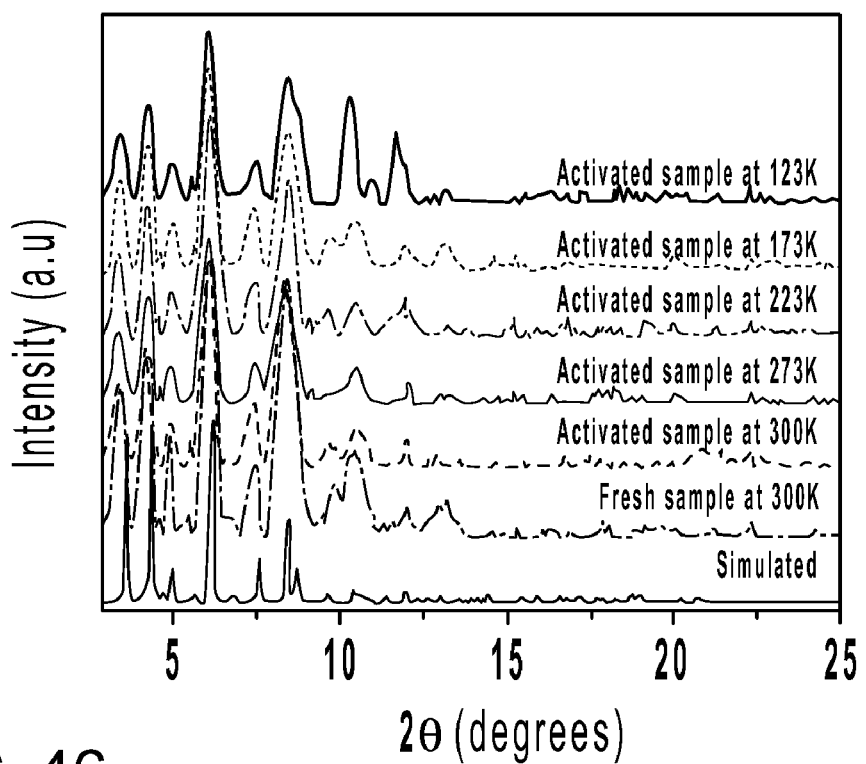
FIG. 46 shows X-ray powder diffraction patterns for fresh (solvated) $Cu_2(BBPDC)_2$ and $Cu_2(BBPDC)_2$ activated at various temperatures.

As discussed above with $Ni_8(\mu_3\text{-OH})_4(BBDC)_6$, and as shown in FIG. 24, the lattice size parameters for $Zn_2(BBPDC)_2$, $Co_2(BBPDC)_2$, and $Cu_2(BBPDC)_2$ show virtually no response to temperature over a wide range. The opening of the temperature-adjustable pore size hydrophobic pore 126 appears to be controlled by the amplitude of the thermal vibration of the hydrophobic moieties 113. As shown in FIG. 45 for $Co_2(BBPDC)_2$ and FIG. 46 for $Cu_2(BBPDC)_2$, the powder X-ray diffraction studies reveal their framework integrities and show no peak shifts at different temperatures. As shown in FIGS. 25 ($Zn_2(BBPDC)_2$), 33 ($Co_2(BBPDC)_2$), and 39 ($Cu_2(BBPDC)_2$), gas adsorption data show the hydrophobic chambers 118 are not accessible when the hydrophilic pores 116 are closed. As discussed herein above, activation results in the freeing of the hydrophilic pores 116 upon activation.

Examples

Commercially available reagents were used as received without further purification. Elemental analyses (C, H, and N) were obtained by Canadian Microanalytical Service, Ltd. Thermogravimetric analyses were performed under $N_2$ on a PerkinElmer TGA 7.

Figure 11:
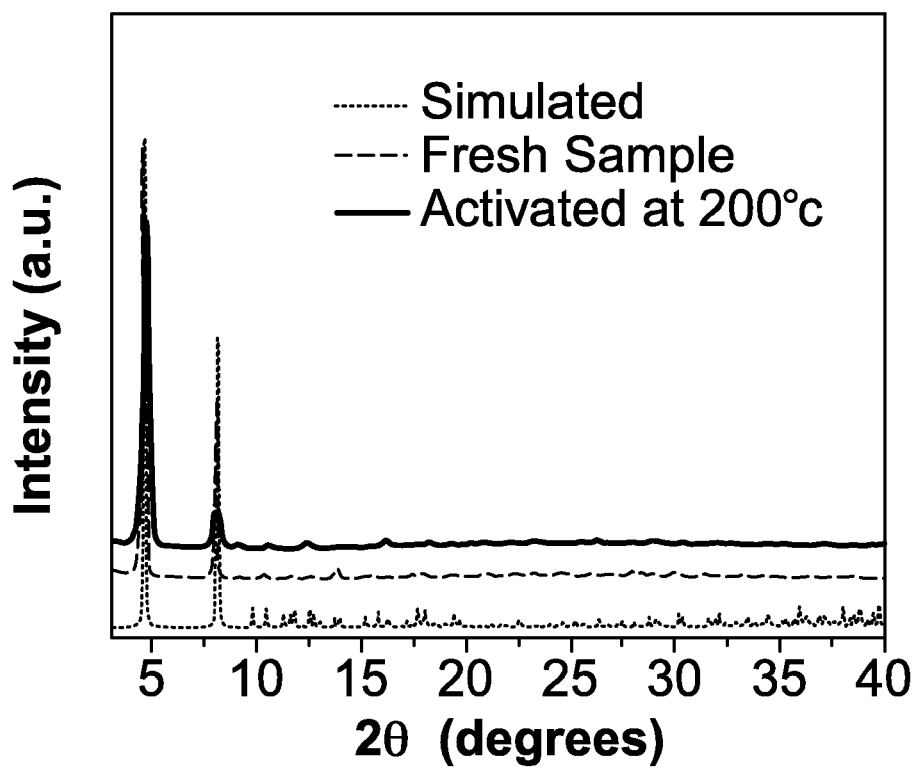
FIG. 11 shows X-ray powder diffraction patterns for fresh (solvated) $Ni_8(\mu_3\text{-}OH)_4(BBDC)_6$ and $Ni_8(\mu_3\text{-}OH)_4(BBDC)_6$ activated at 200 deg. C.

For $Ni_8(\mu_3\text{-OH})_4(BBDC)_6$, single crystal X-ray determination (Table 1 and FIG. 11) was performed on a Bruker Smart Apex® diffractometer (Bruker AXS, Inc., Madison, Wis.) using Mo—Kα radiation ($\lambda$=0.71073 Å). The data were collected on a crystal with dimensions of 0.23 mm×0.08 mm at −60 deg. C. A total of 1321 frames of data were collected using ω-scans with an increment of 0.3 deg. and a counting time of 60 sec/frame. The raw data were processed using SAINT+® (Bruker) to yield the HKL file. Adsorption corrections were applied using SADABS® (Bruker). Direct methods were used to solve the structure, which was refined by full-matrix least-squares on F$^2$ with anisotropic displacement parameters. The hydrogen atoms on carbon and oxygen atoms were calculated in ideal positions with isotropic displacement parameters set to 1.2*$U_{eq}$ of the attached atom.

For $Zn_2(BBPDC)_2$, $Co_2(BBPDC)_2$, and $Cu_2(BBPDC)_2$, single crystal X-ray data (Tables 2-4 and FIGS. 45 and 46) were collected on a Bruker SMART APEX® diffractometer equipped with an Oxford Cryostream (Oxford, England, UK) low temperature device and a fine-focus sealed-tube X-ray source (Mo—Kα radiation, $\lambda$=0.71073 Å, graphite monochromated) operating at 45 kV and 35 mA. Frames were collected with 0.3° intervals in φ and ω for 30 s per frame such that a hemisphere of data were collected. Raw data collection and refinement were done using SMART® (Bruker). Data reduction was performed using SAINT+® (Bruker) and corrected for Lorentz and polarization effects. Adsorption corrections were applied using the SADABS® (Bruker) routine. The structure was solved by direct methods and refined by full-matrix least-squares on F$^2$ with anisotropic displacement using SHELX-97® (Bruker). Non-hydrogen atoms were refined with anisotropic displacement parameters during the final cycles. Hydrogen atoms on carbon were calculated in ideal positions with isotropic displacement parameters set to 1.2*$U_{eq}$ of the attached atom. In all cases, solvent molecules were highly disordered, and attempts to locate and refine the solvent peaks were unsuccessful. Contributions to scattering due to these solvent molecules were removed using the PLATON SQUEEZE® routine of and refined further using the data generated.

As shown in FIG. 10, thermogravimetric analysis (TGA) of $Ni_8(\mu_3\text{-OH})_4(BBDC)_6$ (9.8 mg) was performed with a Perkin-Elmer TGA 7 Thermogravimetric Analyzer under 50.0 mL/min flow of $N_2$. (FIG. 10.) The first weight loss of 6.72 percent (calculated: 6.71 percent) from 50 deg. C. to 120 deg. C. corresponds to the loss of eight free $H_2O$ molecules, followed by the weight loss of 6.42 percent (calculated: 6.71 percent) corresponding to eight coordinated $H_2O$ molecules from 120 deg. C. to 250 deg. C. Beyond 400 deg/C., the framework decomposes completely.

Figure 22:
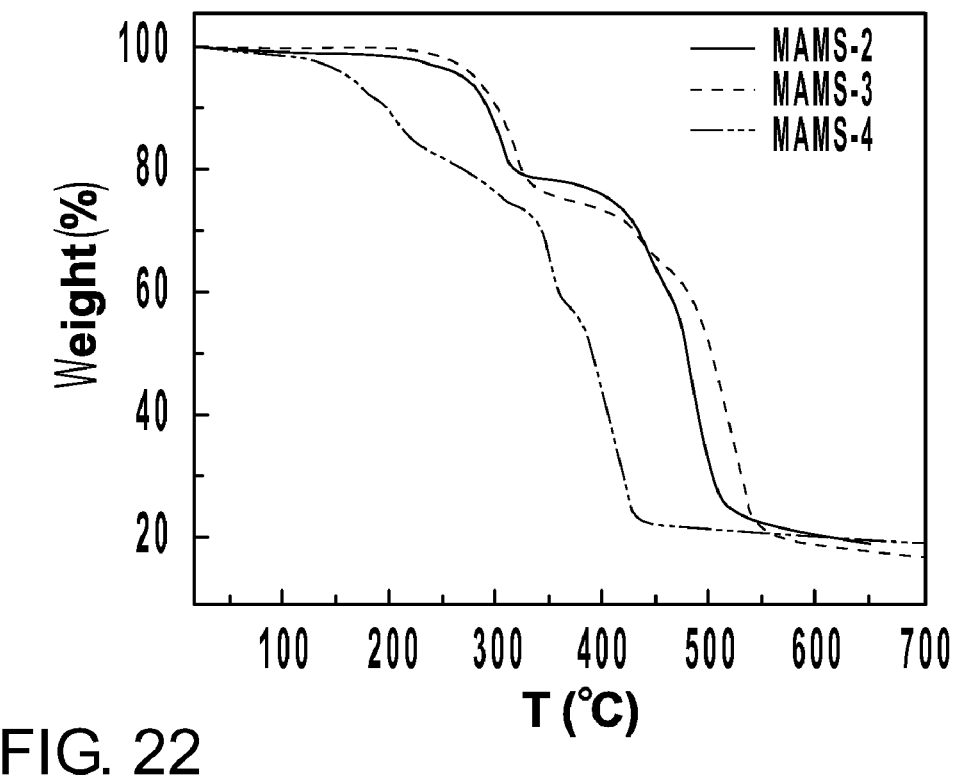
FIG. 22 shows thermogravimetric analyses (TGA) of:
$Zn_2((CH_3)_3CC_6H_4C_6H_3(CO_2)_2)_2(Zn_2(BBPDC)_2)$,
$Co_2((CH_3)_3CC_6H_4C_6H_3(CO_2)_2)_2(Co_2(BBPDC)_2)$, and
$Cu_2((CH_3)_3CC_6H_4C_6H_3(CO_2)_2)_2(Cu_2(BBPDC)_2)$.

TGA analyses for $Zn_2(BBPDC)_2$, $Co_2(BBPDC)_2$, and $Cu_2(BBPDC)_2$ are shown in FIG. 22. As shown in FIG. 22, the first 24.6 percent (calculated=26.0 percent) weight loss of $Zn_2(BBPDC)_2$ from about 300° C. to 420° C. corresponds to the loss of three DMF free guest molecules and two coordinated aqua axial elements. Decomposition of the BBPDC ligands starts at around 430 deg. C. and ends at 650 deg. C. with an overall weight loss of 56.4 percent (calculated=57.2 percent). For $Co_2(BBPDC)_2$, the loss of three DMA free guest molecules and two coordinated aqua axial elements (28, FIG. 5) also starts at around 300 deg. C. and ends at about 420 deg. C. (calculated=29.5 percent and found=28.0 percent), which is followed by the decomposition of the BBPDC ligands with an overall weight loss of 55.0 percent (calculated=55.6 percent). Finally for $Cu_2(BBPDC)_2$, the loss of three DMF free guest molecules and two coordinated aqua axial elements starts at about 150 deg. C and ends at about 350 deg. C (calculated=29.5 percent and found=28.0 percent), which is closely followed by the decomposition of the BBPDC ligands with the weight loss of 54.0 percent (calculated=57.5 percent) ending at around 430 deg. C.

Figure 17:
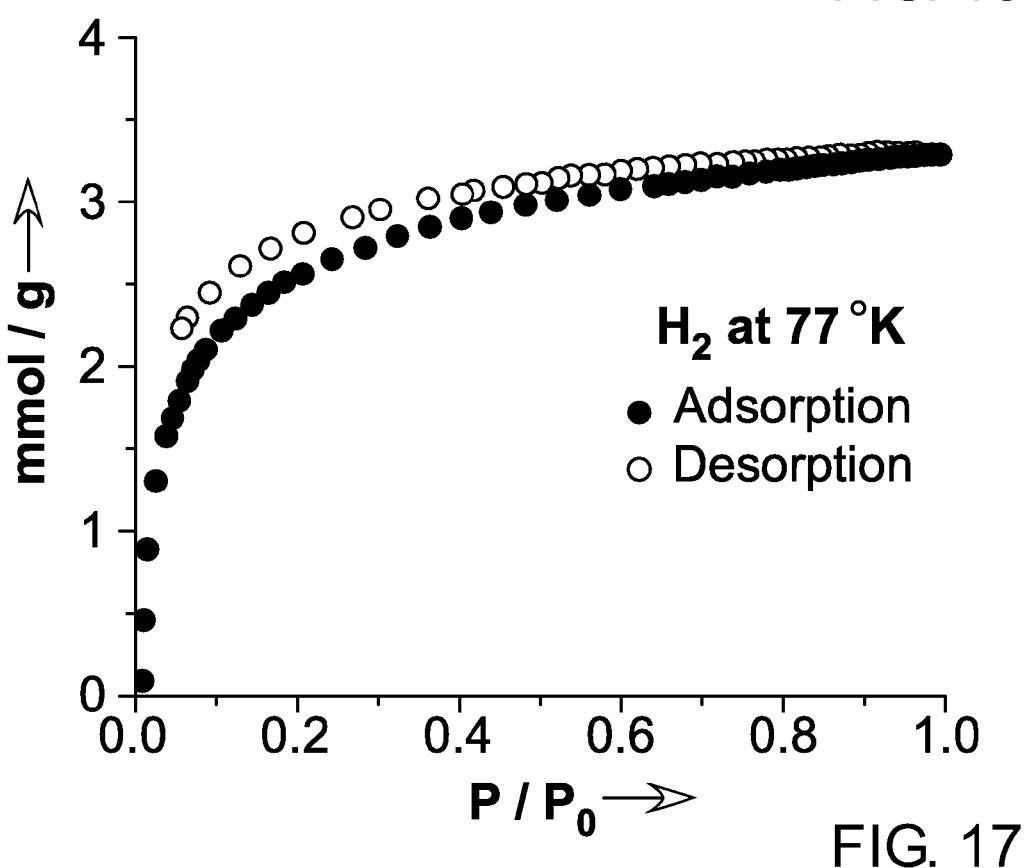
FIG. 17 shows $H_2$ sorption isotherms (adsorption and desorption) at 77 deg. K. for $Ni_8(\mu_3\text{-}OH)_4(BBDC)_6$.
Figure 18:
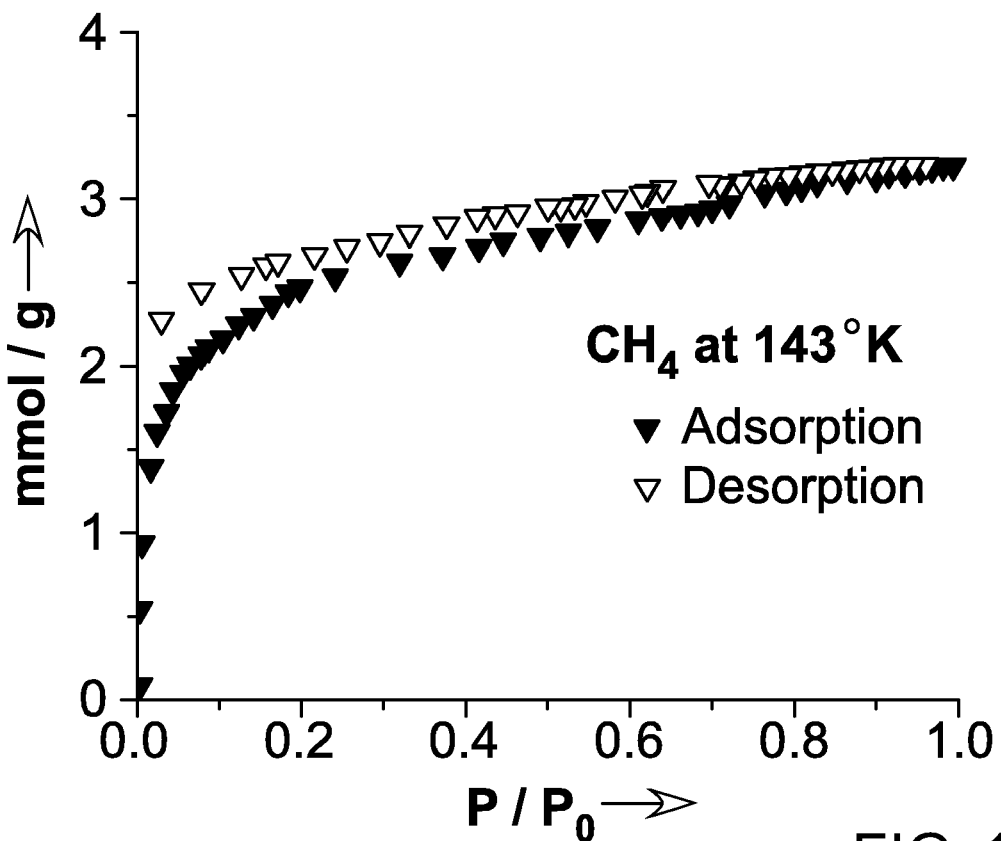
FIG. 18 shows $CH_4$ sorption isotherms (adsorption and desorption) at 143 deg. K. for $Ni_8(\mu_3\text{-}OH)_4(BBDC)_6$.
Figure 19:
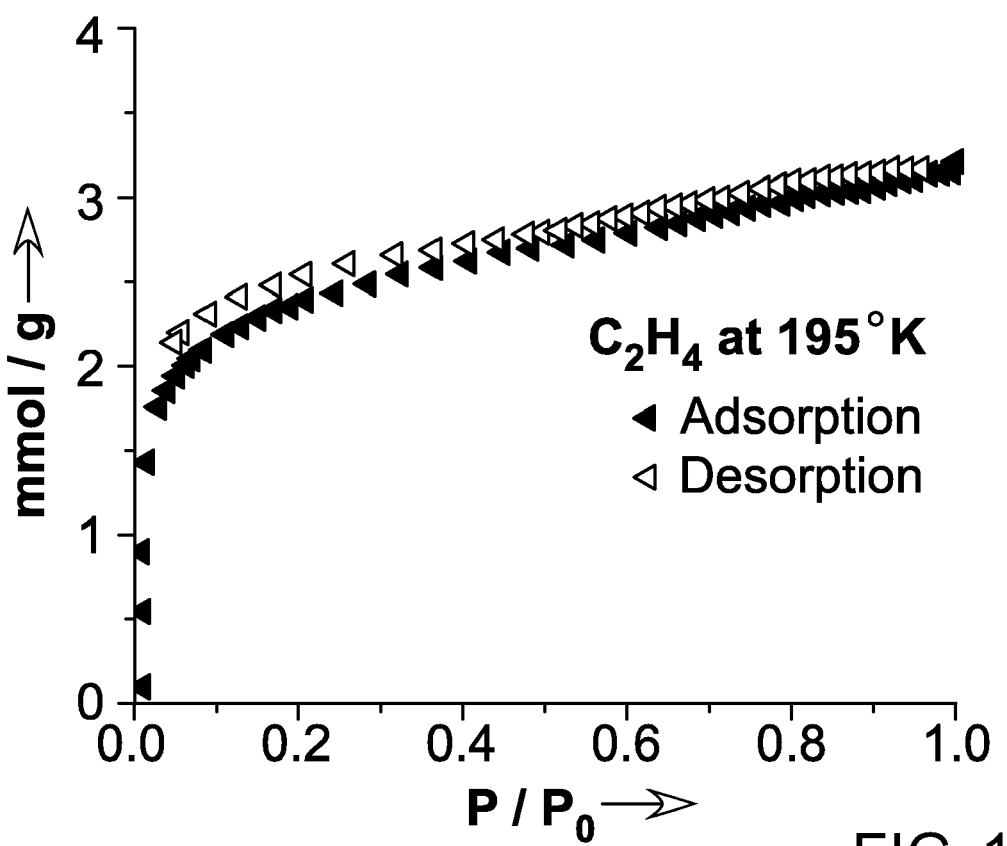
FIG. 19 shows $C_2H_4$ sorption isotherms (adsorption and desorption) at 195 deg. K. for $Ni_8(\mu_3\text{-}OH)_4(BBDC)_6$.

For $Ni_8(\mu_3\text{-}OH)_4(BBDC)_6$, gas adsorption measurements were measured with an SA 3100 surface area and pore size analyzer (Beckman Coulter, Inc., Fullerton, Calif.). The sample was held under dynamic vacuum ($<10^{-3}$ Torr) at 200 deg. C. overnight to remove the free and coordinated water molecules. Before the measurement, the sample was evacuated again by using the "outgas" function of the surface area analyzer for one hour at 200 deg. C. A sample of 40.0 mg was used for $N_2$ (99.999 percent) adsorption measurement, and was maintained at 77K with liquid nitrogen. (FIG. 9a.) In the $H_2$ adsorption measurement, high purity hydrogen (99.9995 percent) and a 40.0 mg sample were used. The regulator and pipe were flushed with hydrogen before connecting to the analyzer. The internal lines of the instrument were flushed three times by utilizing the "flushing lines" function of the program to ensure the purity of hydrogen. The measurement was maintained at 77 deg. K. with liquid nitrogen. (FIGS. 12 and 17.) Similar to the procedures used for $H_2$ measurement at 77 K, highly pure $O_2$ (99.99 percent) (FIG. 9a), CO (99.99 percent) (FIG. 9a), $CH_4$ (99.997 percent) (FIG. 18), $C_2H_4$ (99.5 percent) (FIGS. 15 (175 deg. K.) and 19 (195 deg. K.)), $C_3H_6$ (99.5%) (FIGS. 9c and 9f), iso-$C_4H_{10}$ (99.5 percent) (FIG. 16), $SF_6$ (99.8 percent) (FIG. 16) and $CO_2$ (99.99 percent) (FIG. 13) were used for their respective gas adsorption measurements. All the gases used for the measurements were purchased from Linde Gas LLC, Cincinnati, Ohio. To prevent condensation of CO and $O_2$ at 77 K, the pressure ranges were below 448 Torr and 156 Torr, respectively. To prevent condensation of $O_2$ at 87 K, the pressure range was below 466 Torr. To prevent condensation of $C_2H_4$ at 143 K, the pressure range was below 120 Torr. To prevent condensation of $C_3H_6$ at 195 K, the pressure range was below 110 Torr. To prevent condensation of iso-$C_4H_{10}$ at 241 K, the pressure range was below 210 Torr. For all adsorption isotherms, $P_0$ represents a relative saturation pressure given by the SA 3100 during the measurements. At 77 deg. K., $P_0$ was 757 Torr for $H_2$ (FIG. 12) and $N_2$, 441 Torr for CO, and 151 Torr for $O_2$. At deg. 87 K, $P_0$ was 757 Torr for CO and $N_2$ and 465 Torr for $O_2$. At 113 deg. K., $P_0$ was 757 Torr for CO, $CH_4$, and $N_2$. At 143 K, $P_0$ was 757 Torr for $CH_4$ and 118 Torr for $C_2H_4$. At 175 deg. K., $P_0$ was 757 Torr for $C_2H_4$. At 195 deg. K., $P_0$ was 757 Torr for $C_2H_4$ and $CO_2$ and 108 Torr for $C_3H_6$. At 241 deg. K., $P_0$ was 757 Torr for $C_3H_6$ and 205 Torr for iso-$C_4H_{10}$. At 298 K, $P_0$ was 757 Torr for iso-$C_4H_{10}$ and $SF_6$.

A Beckman Coulter SA3100 surface area and pore size analyzer was utilized for the gas adsorption measurements for $Zn_2(BBPDC)_2$, $Co_2(BBPDC)_2$, and $Cu_2(BBPDC)_2$. NMR data were collected on a Bruker 300 MHz spectrometer. For $Zn_2(BBPDC)_2$ and $Co_2(BBPDC)_2$, the samples were held under dynamic vacuum ($<10^{-3}$ torr) at 300 deg. C., and for $Cu_2(BBPDC)_2$, the temperature was 170 deg. for five hours to remove the free guest solvent molecules (DMF or DMA) and coordinated alpha ligands. Before the measurement, the sample was evacuated again by using the "outgas" function of the surface area analyzer for one hour at 300 deg. C. for $Zn_2(BBPDC)_2$ and $Co_2(BBPDC)_2$ and 170 deg. C. form $Cu_2(BBPDC)_2$. A sample of about 100 mg was used for $N_2$ (99.999 percent) adsorption measurement and was maintained at 77 deg. K. with liquid nitrogen. In the $H_2$ storage measurement, high purity $H_2$ (99.9995 percent) and a 100 mg sample was used. The regulator and pipe were flushed with hydrogen before they were connected to the analyzer. The internal lines of the instrument were flushed three times by utilizing the "flushing lines" function of the program to ensure the purity of $H_2$. The measurement was maintained at 77 deg. K. with liquid nitrogen. Similar to the procedures used for $H_2$ measurement at 77 deg. K., highly pure $O_2$ (99.99 percent), CO (99.99 percent), $CH_4$ (99.997 percent), $C_2H_4$ (99.5 percent), $C_3H_6$ (99.5 percent), iso-$C_4H_{10}$ (99.5 percent), $SF_6$ (99.8 percent) and $CO_2$ (99.99 percent) were used for their respective gas adsorption measurements. All the gases used for the measurements were purchased from Linde Gas, LLC, Cincinnati, Ohio. The temperatures at 87 deg. K., 113 deg. K., 143 deg. K., 195 deg. K. and 231 deg. K. were maintained with a liquid argon bath, iso-pentane-liquid nitrogen bath, n-pentane-liquid nitrogen bath, acetone-dry ice bath, and acetonitrile-dry ice bath, respectively. To prevent condensation of CO and $O_2$ at 77 deg. K., the pressure ranges were below 448 torr and 156 torr, respectively. To prevent condensation of $O_2$ at 87 deg. K., the pressure range was below 466 torr. To prevent condensation of $C_2H_4$ at 143 deg. K., the pressure range was below 120 torr. To prevent condensation of $C_3H_6$ at 195 deg. K., the pressure range was below 110 torr. To prevent condensation of iso-$C_4H_{10}$ at 241 deg. K., the pressure range was below 210 torr. For all adsorption isotherms, $P_0$ represents a relative standard (pressure of the saturation tube of the Beckman Coulter SA 3100 surface area during the measurement): At 77 deg. K., $P_0$ was 757 torr for $H_2$ and $N_2$; 441 torr for CO; and 151 torr for $O_2$. At 87 deg. K., $P_0$ was 757 torr for CO and $N_2$ and 465 torr for $O_2$. At 113 deg. K., $P_0$ was 757 torr for CO, $CH_4$, and $N_2$. At 143 deg. K, $P_0$ was 757 torr for $CH_4$ and 118 torr for $C_2H_4$. At 195 K, $P_0$ was 757 torr for $C_2H_4$ and $CO_2$ and 108 torr for $C_3H_6$. At 241 deg. K., $P_0$ was 757 torr for $C_3H_6$ and 205 torr for iso-$C_4H_{10}$. At 295 deg. K., $P_0$ was 757 torr for iso-$C_4H_{10}$ and $SF_6$.

$Ni_8(\mu_3\text{-}OH)_4(BBDC)_6$ was synthesized by a solvothermal reaction between $Ni(NO_3)_2$ and 5-tert-butyl-1,3-benzenedicarboxylate (BBDC). 5-tert-butyl-1,3-benzenedicarboxylic acid ($H_2BBDC$), (0.075 g, 0.34 mmol) and $Ni(NO_3)_2.6H_2O$ (0.15 g, 0.51 mmol) in 7.5 mL $H_2O$/ethylene glycol (volume ratio 4:1) were placed in a 20 mL Teflon® (E. I. du Pont de Nemours and Company, Wilmington, Del.) container and sealed in an autoclave. The autoclave was heated to 210 deg. C. (heating rate 2 deg. C./min) in a programmable oven at which it stayed for 24 hours before being cooled to room temperature (cooling rate 0.5 deg. C./min). The light green needle-like crystals obtained were washed with distilled water and methanol to give pure solvated $Ni_8(\mu_3\text{-}OH)_4(BBDC)_6$ with the formula $Ni_8(\mu_3\text{-}OH)_4(C_{12}H_{12}O_4)_6(H_2O)_8 \cdot 8H_2O$ (55 percent yield based on $H_2BBDC$). Elemental analysis, calculated (percent): C-40.28, H-5.07, O-32.79. found: C-40.69, H-5.07, O-33.05. IR (cm$^{-1}$): 3305 (w, br), 2960 (m), 1033 (s), 865 (s), 785 (m).

TABLE 1

(Crystal Data - Solvated $Ni_8(\mu_3\text{-}OH)_4(BBDC)_6$)

| | |
|---|---|
| Empirical formula | $C_{36}H_{52}Ni_4O_{21}$ |
| Formula weight | 1055.62 |
| Temperature | 213(2) K |
| Wavelength | 0.71073 Å |
| Crystal system, space group | Monoclinic, P2(1)/c |
| Unit cell dimensions | a = 10.9685 (2) Å alpha = 90.00°; |
| | b = 11.308 (2) Å beta = 96.781(3)°; |
| | c = 38.405 (7) Å gamma = 90.00°. |
| Volume | 4730.1(14) Å$^3$ |
| Z, Calculated density | 4, 1.482 g/cm$^3$ |
| Absorption coefficient | 1.641 mm$^{-1}$ |
| F(000) | 2192 |
| Crystal size | 0.23 × 0.08 × 0.08 mm |
| Theta range for data collection | 1.87 to 23.33° |
| Reflections collected/unique | 16860/6818 [R(int) = 0.0668] |
| Completeness to theta = 18.91 | 99.2% |
| Absorption correction | Empirical |
| Max. and min. transmission | 1.000 and 0.648 |
| Refinement method | Full-matrix least-squares on F$^2$ |
| Data/restraints/parameters | 6818/18/581 |
| Goodness-of-fit on F^2 | 1.021 |
| Final R indices [I > 2σ(I)] | $R_1$ = 0.0609, $wR_2$ = 0.1456 |
| R indices (all data) | $R_1$ = 0.0928, $wR_2$ = 0.1624 |

Figure 9B:
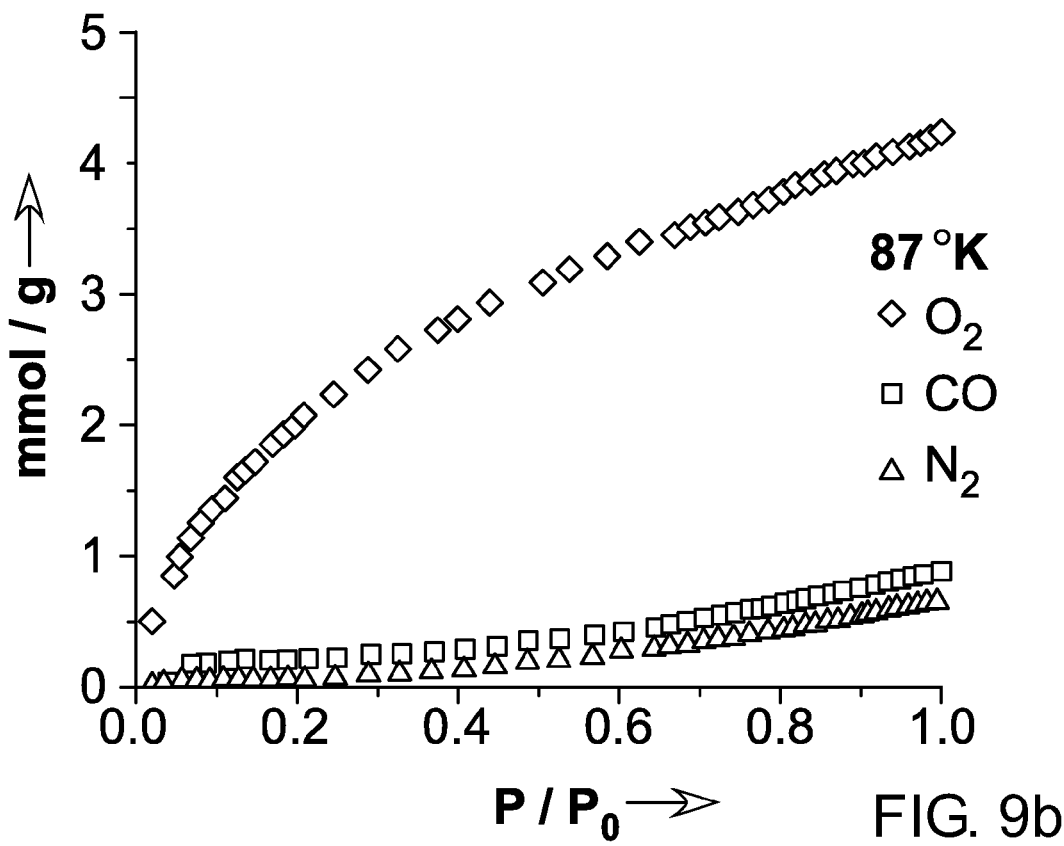

Referring now to FIG. 9a, at 77 deg. K., $Ni_8(\mu_3\text{-}OH)_4$(BBDC)$_6$ excludes CO, N$_2$, and O$_2$, but allows H$_2$ to be adsorbed. When the temperature is raised to the temperature of liquid argon (87 deg. K.), FIG. 9b shows that only a small amount of CO or N$_2$ is adsorbed by MAMS-1. At that temperature, however, $Ni_8(\mu_3\text{-}OH)_4$(BBDC)$_6$ can take up a significant amount of O$_2$. The adsorption isotherm of O$_2$ shows typical Type-I behavior.

Dioxygen (3.46 Å) can be selectively adsorbed from a mixture with N$_2$ (3.64 Å) and CO (3.76 Å), which would imply that at 87 deg. K., the temperature-adjustable pore size hydrophobic pore opening 16 is about 3.5 Å. See FIG. 9b.

Figure 9C:
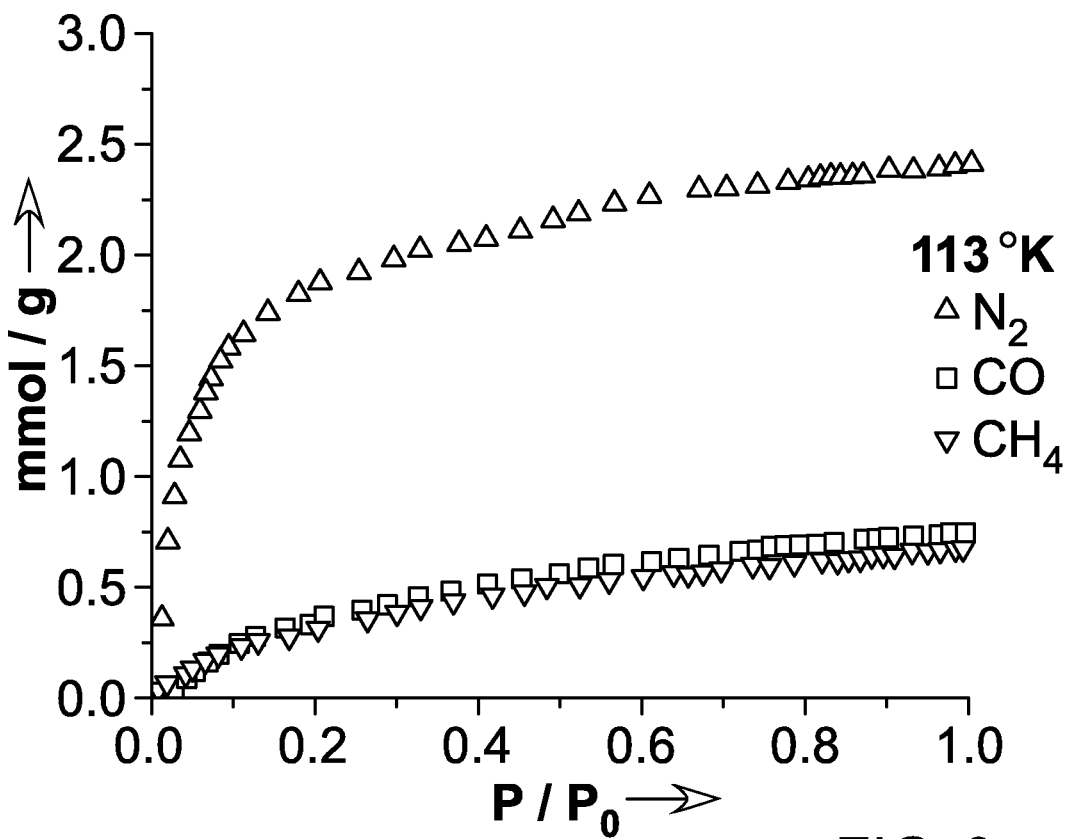

Referring now to FIG. 9c, at 113 deg. K., $Ni_8(\mu_3\text{-}OH)_4$(BBDC)$_6$ can take up a moderate amount of N$_2$, but relatively low quantities of CO (3.76 Å) and CH$_4$ (3.8 Å). Thus, the temperature-adjustable pore size hydrophobic pore opening 26 is wide enough to enable N$_2$ (3.64 Å) to be adsorbed, but molecules with larger kinetic diameters such as CO and CH$_4$ are not.

Figure 9D:
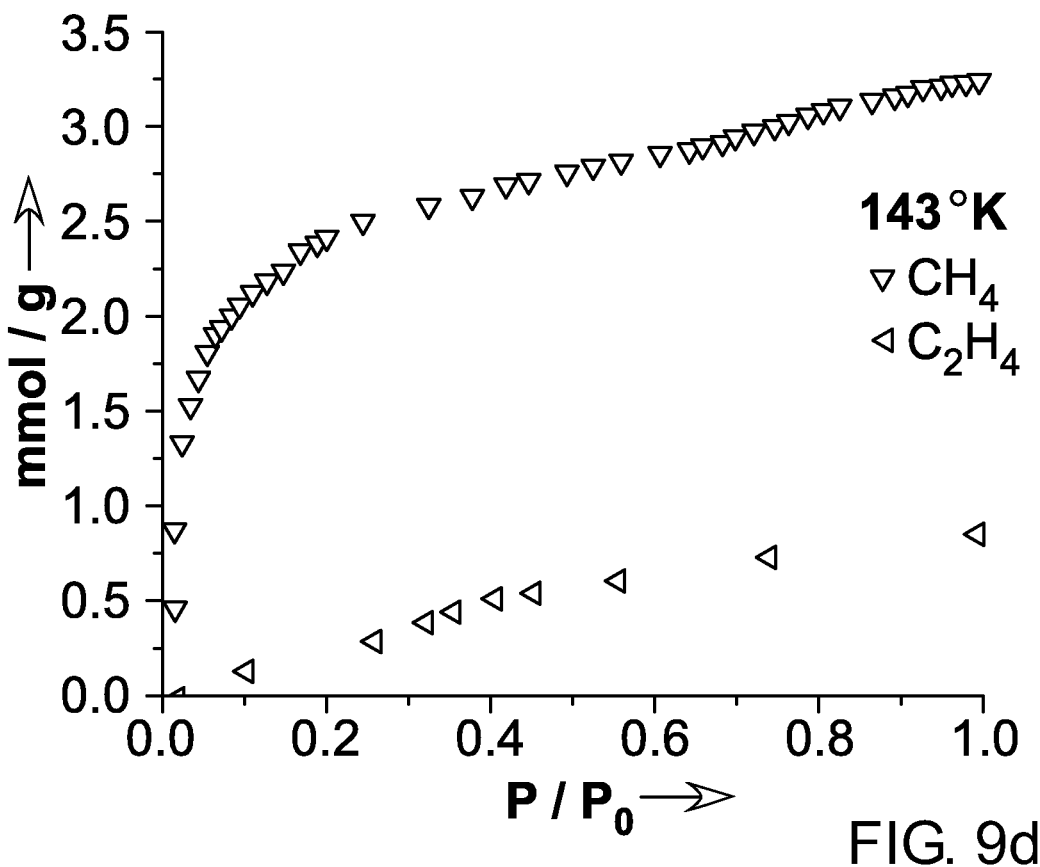
Figure 9E:
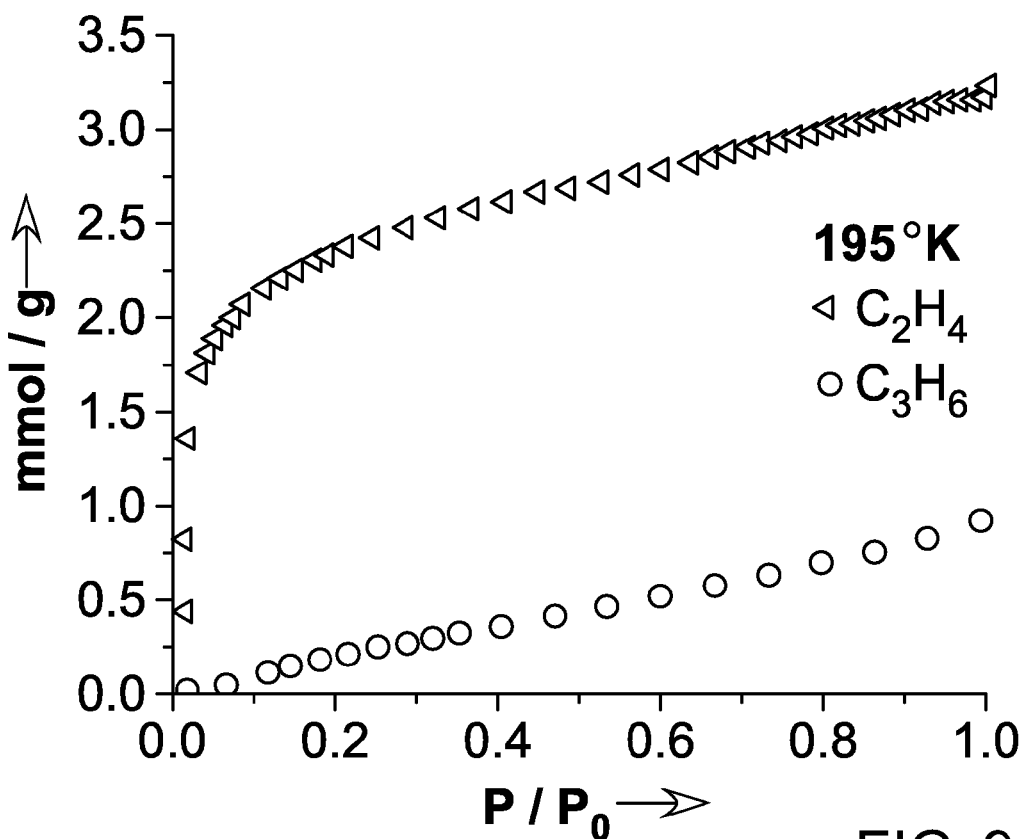
Figure 9F:
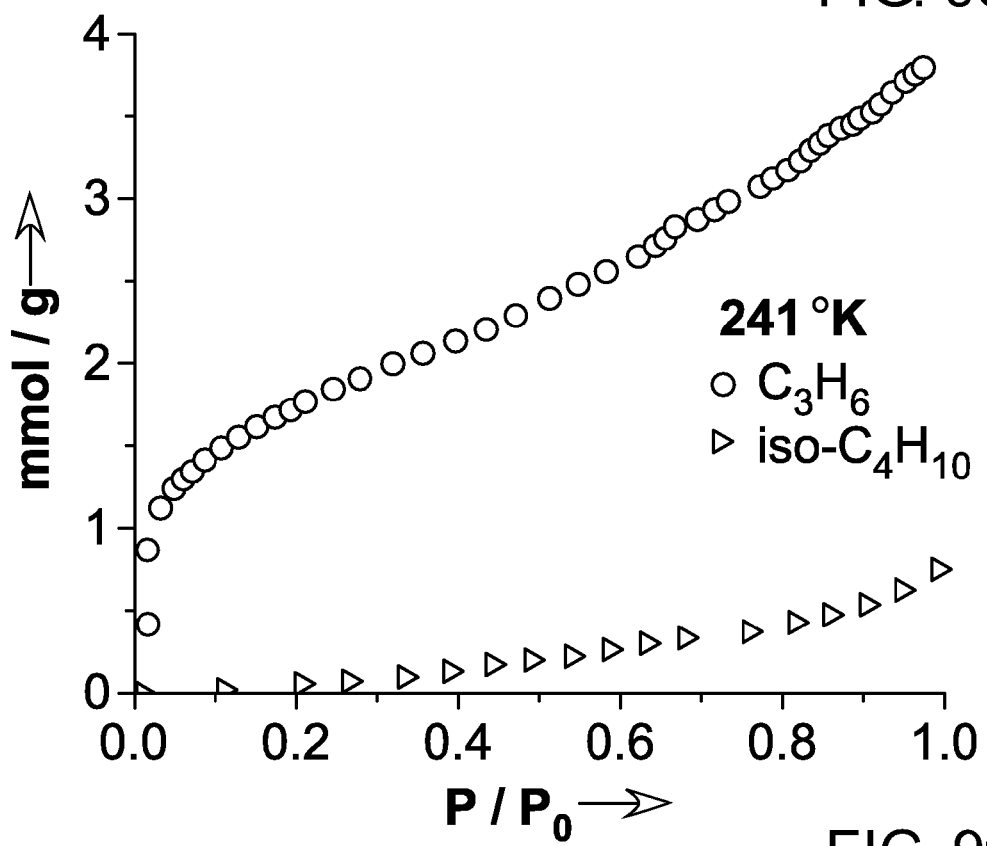

Referring now to FIG. 9d, $Ni_8(\mu_3\text{-}OH)_4$(BBDC)$_6$ appears to distinguish between CH$_4$ and C$_2$H$_4$ (3.8 Å) at 143 deg. K. In addition, C$_2$H$_4$ is distinguished from C$_3$H$_6$ at 195 deg. K. (FIG. 9e) and C$_3$H$_6$ (4.5 Å) from iso-C$_4$H$_{10}$ (5.0 Å) at 241 deg. K. (FIG. 9f).

To synthesize Zn$_2$(BBPDC)$_2$, a mixture of 20 mg Zn(NO$_3$)$_2$.6H$_2$O and 10 mg H$_2$BBPDC in 1.5 mL dimethylformamide (DMF) solvent was sealed in a Pyrex glass tube (ID 8 mm/OD 10 mm) and heated to 120 deg. C. at a rate of 1 deg. C. per minute. After holding at 120 deg. C. for 24 hours, it was cooled to 35 deg. C. at a rate of 0.1 deg. C. per minute. The resulting colorless crystals were washed with DMF twice to give (Zn$_2$(H$_2$O)$_2$(BBPDC)$_2$.3DMF (yield=85 percent based on H$_2$BBPDC). The reaction was amplified to gram quantity using multiple tubes. Elemental analysis of Zn$_2$(BBPDC)$_2$: calculated: C 55.22 percent, H 5.87 percent, and N 4.29 percent and found: C 55.65 percent, H 5.39 percent, and N 3.98 percent.

TABLE 2

(Crystal Data - Solvated $Zn_2(BBPDC)_2$)

| | |
|---|---|
| Empirical formula | $C_{18}H_{18}ZnO_5$ |
| Formula weight | 379.69 |
| Crystal system, space group | Trigonal, P-3c1 |
| Crystal size (mm) | 0.16 × 0.12 × 0.10 |
| Unit cell dimensions | a = 18.6069 (6) Å alpha = 90.00° |
| | b = 18.6069 (6) Å beta = 90.00° |
| | c = 22.6226 (1) Å gamma = 120.00° |
| Volume | 6783.0 (5) Å$^3$ |
| Z, Calculated density | 12, 1.115 g/cm$^3$ |
| GOF | 1.06 |
| $R_1$, $wR_2$$^b$ | 0.0746, 0.2043 |
| M . . . M distance | 2.951 Å |
| M-aqua bonding distance | 1.869 Å |

Figure 26:
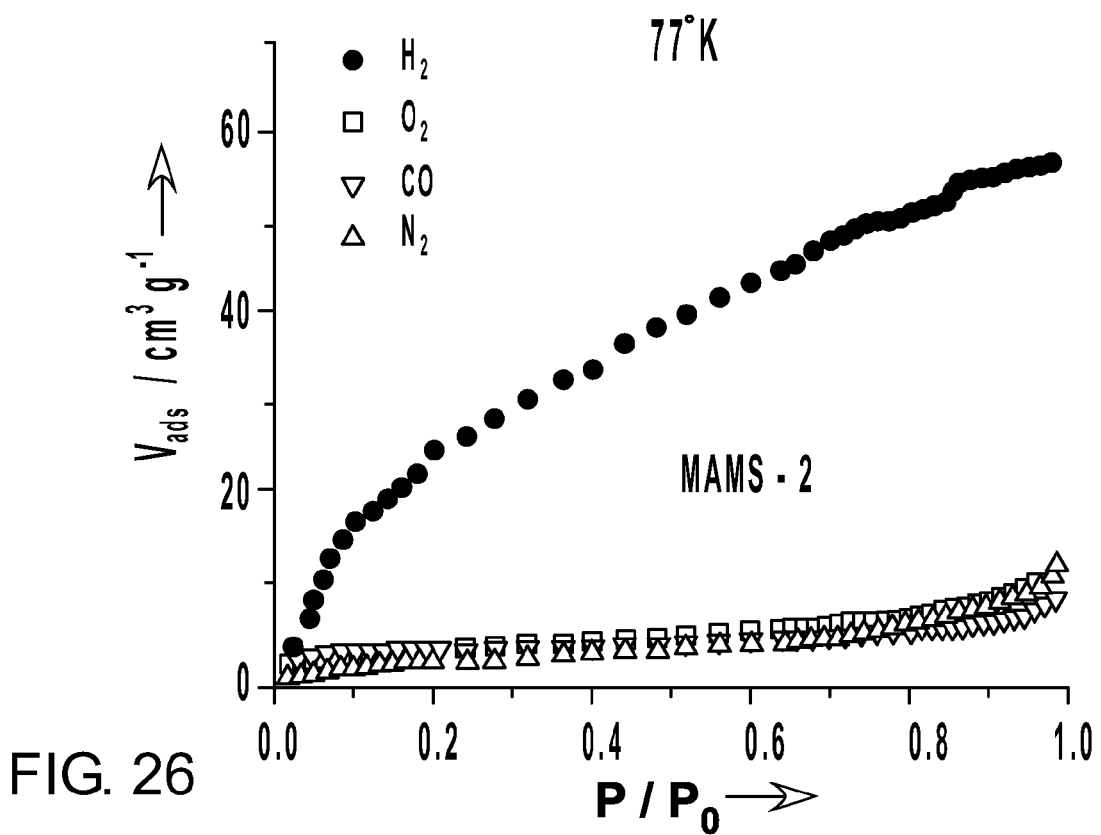
FIGS. 26-32 are gas adsorption isotherms for selected molecular species mixtures at selected temperatures for $Zn_2(BBPDC)_2$.
Figure 27:
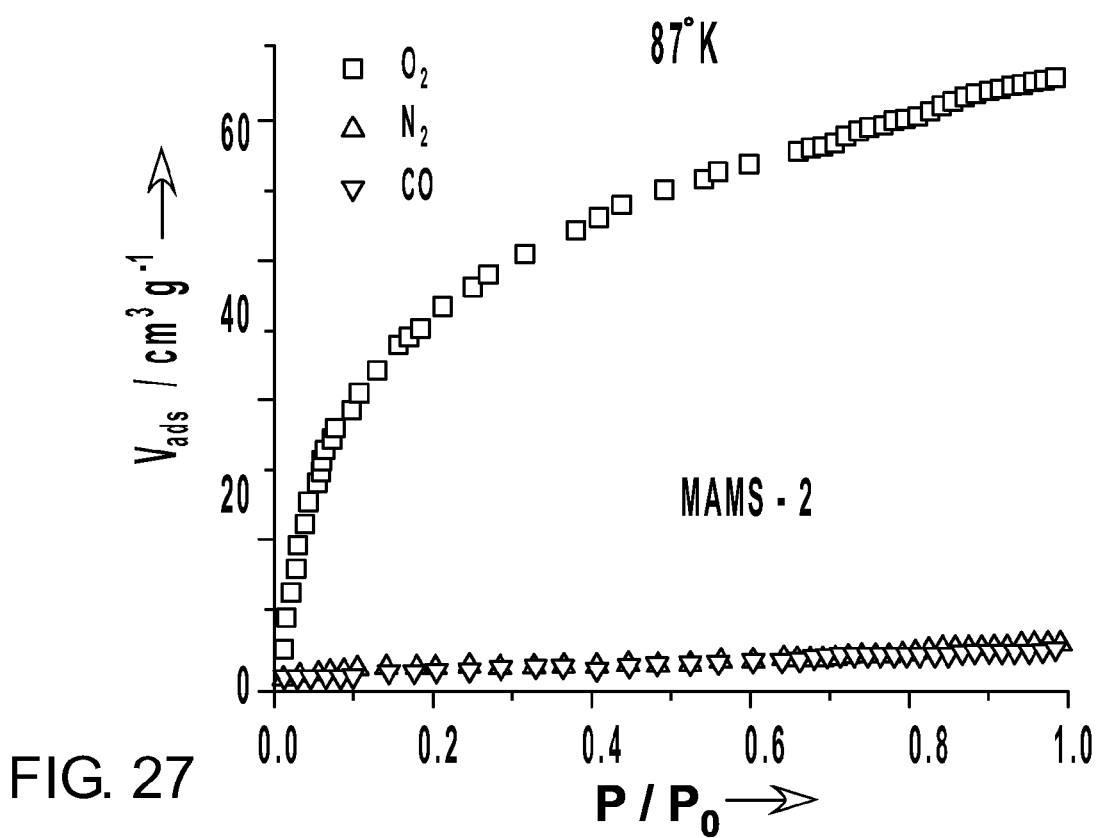
Figure 28:
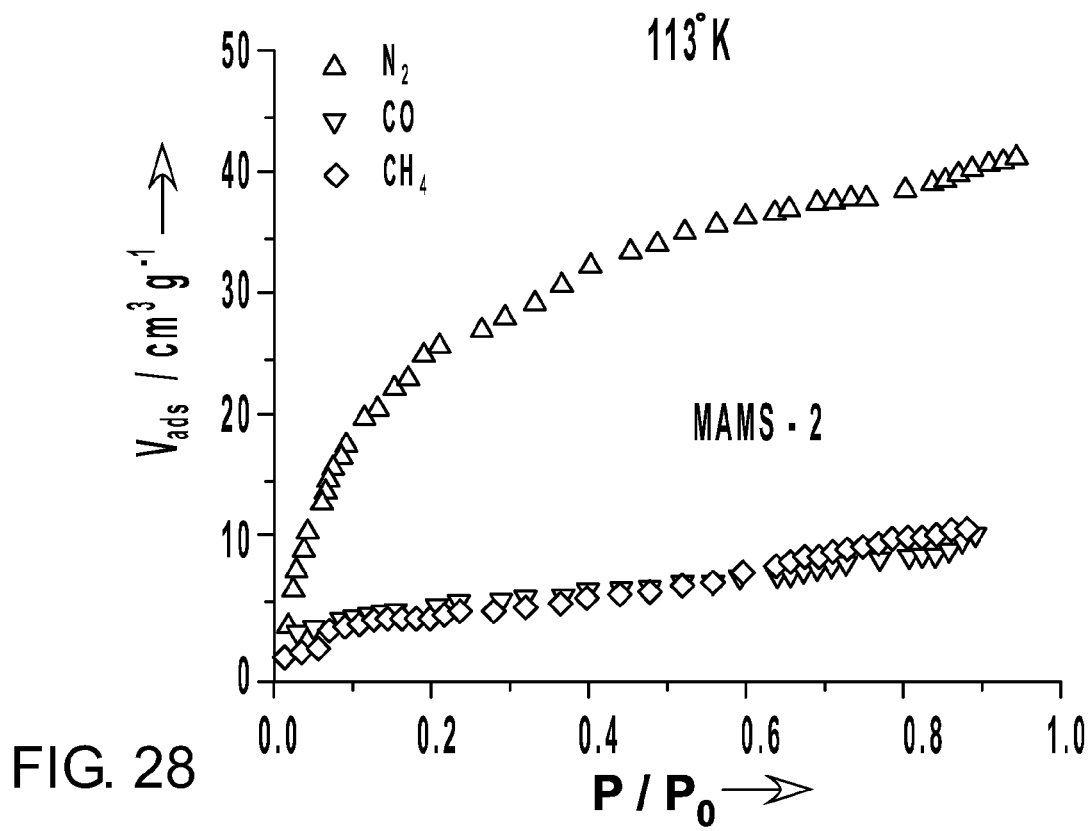

Referring now to FIG. 26 at 77 deg. K., Zn$_2$(BBPDC)$_2$ excludes CO, N$_2$, and O$_2$ but adsorbs H$_2$. When the temperature is raised to liquid argon temperature (87 deg. K., FIG. 27), gas adsorption studies reveal that only a small amount of CO or N$_2$ is adsorbed by Zn$_2$(BBPDC)$_2$. Zn$_2$(BBPDC)$_2$, however, can adsorb a significant amount of O$_2$. The adsorption isotherm of O$_2$ shows Type-I behavior. Dioxygen (3.46 Å) can be selectively adsorbed from a mixture with N$_2$ (3.64 Å) and CO (3.76 Å), which implies that at 87 deg. K. the gate opens to around 3.5 Å.

When the temperature is increased to 113 deg. K. (FIG. 28), Zn$_2$(BBPDC)$_2$ can take up a moderate amount of N$_2$ but relatively low quantities of CO and CH$_4$ (3.8 Å). This implies that at 113 deg. K., the gate opens to about 3.7 Å, wide enough to allow N$_2$ (3.64 Å) to enter the chambers, but molecules with larger kinetic diameters such as CO (3.76 Å) and CH$_4$ (3.8 Å) will stay in the hydrophilic pores. This example indicates the resolution for size discrimination is 0.12 Å.

Figure 29:
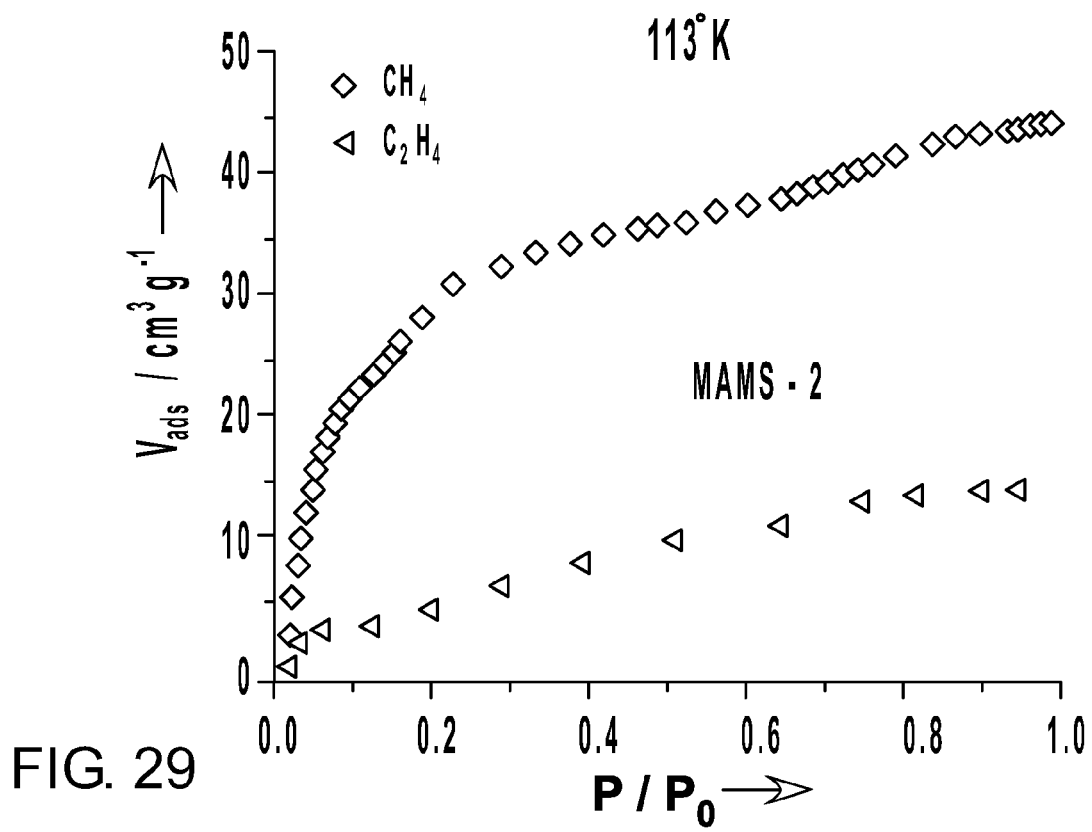
Figure 30:
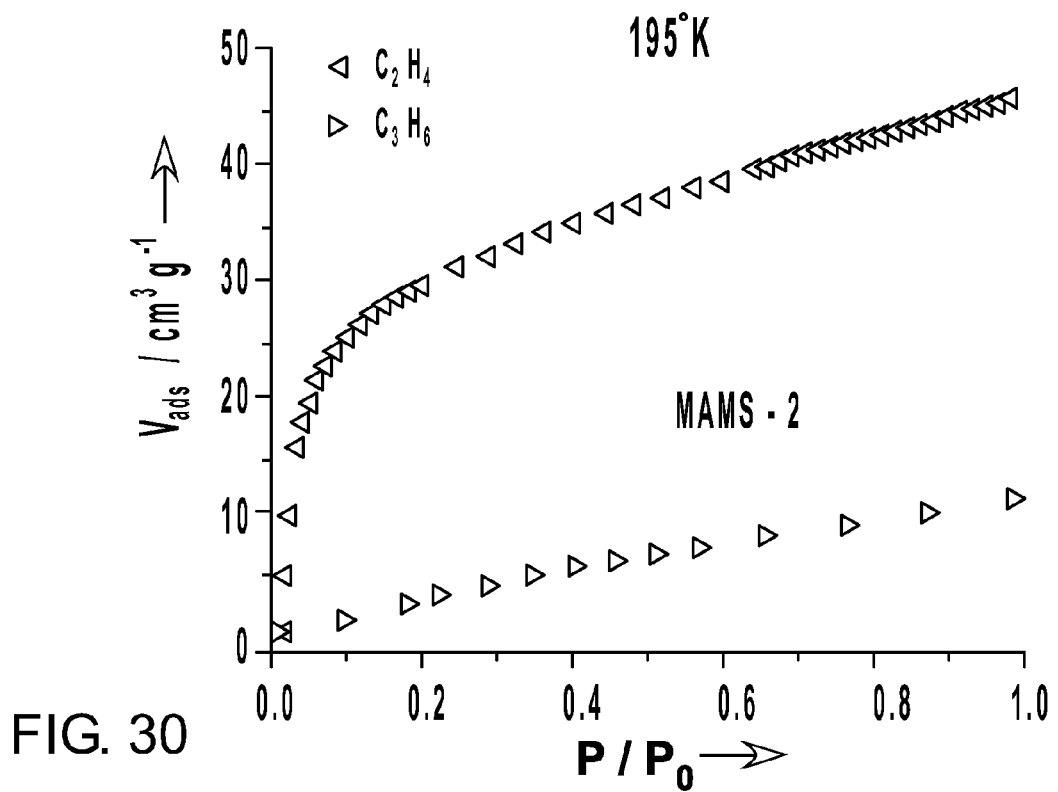
Figure 31:
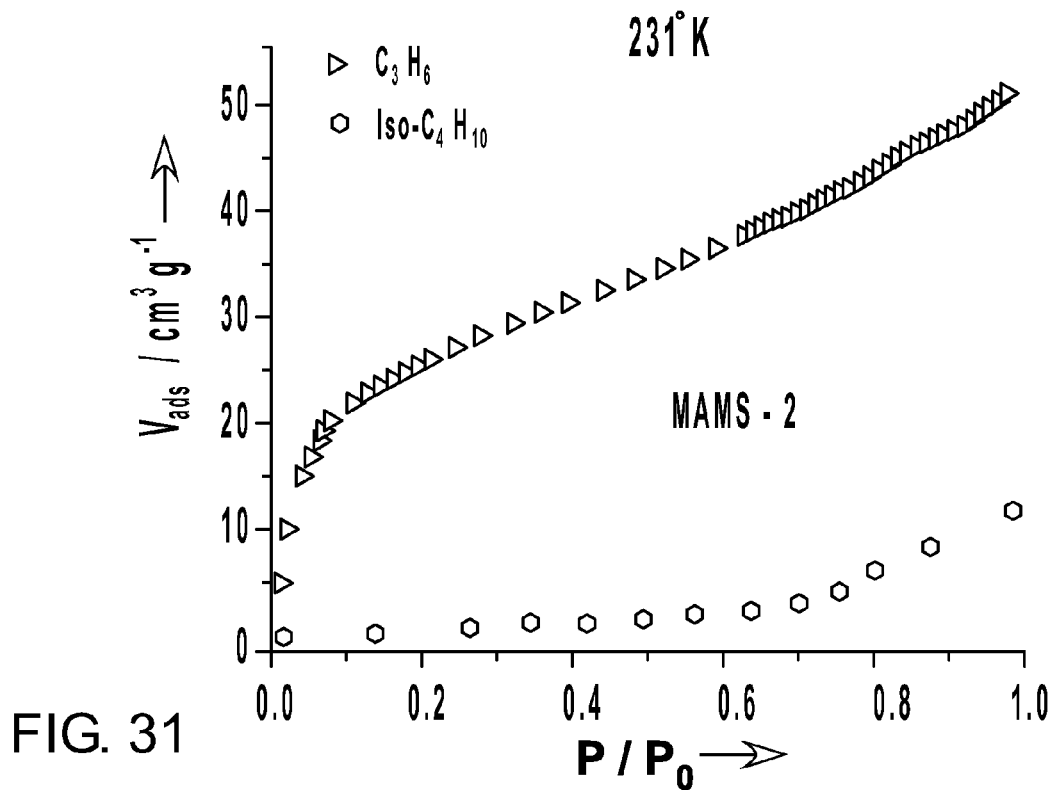
Figure 32:
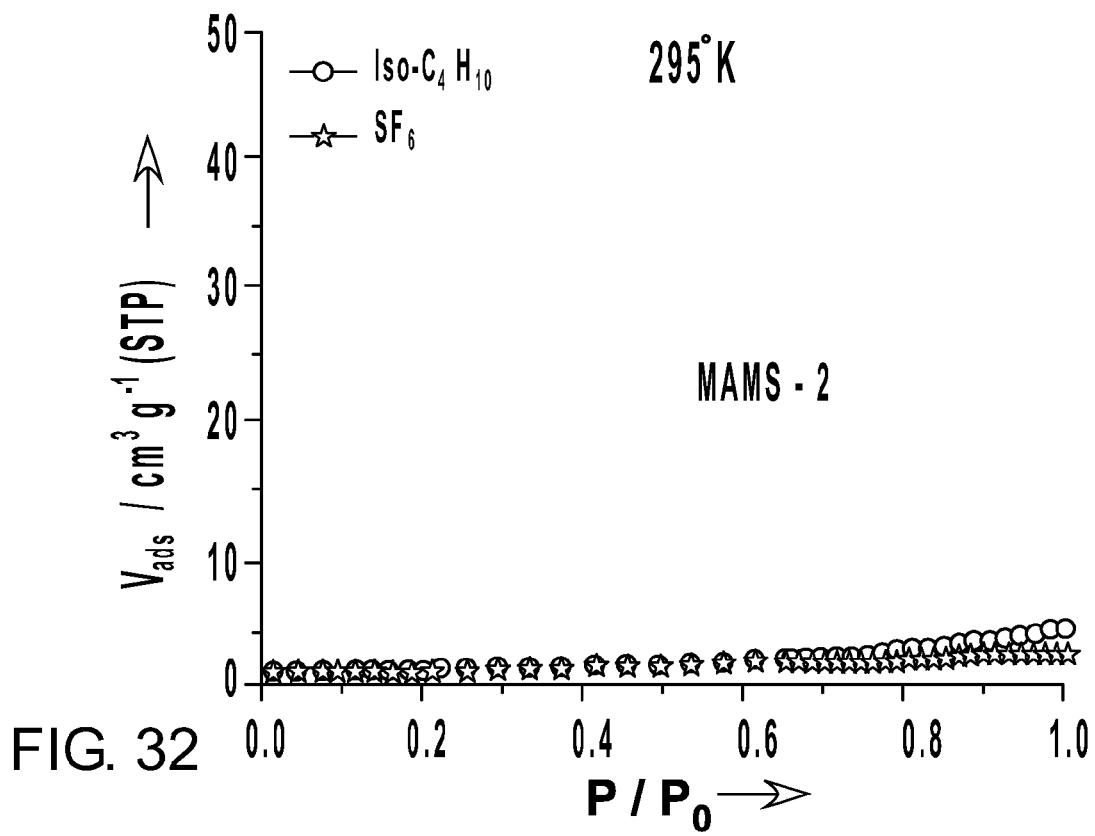

As shown in FIG. 29, Zn$_2$(BBPDC)$_2$ can distinguish CH$_4$ from C$_2$H$_4$ at 143 deg. K. As shown in FIG. 30, Zn$_2$(BBPDC)$_2$ can distinguish C$_2$H$_4$ from C$_3$H$_6$ at 195 deg. K. As shown in FIG. 31, Zn$_2$(BBPDC)$_2$ can distinguish C$_3$H$_6$ from iso-C$_4$H$_{10}$ at 231 deg. K.

To synthesize Co$_2$(BBPDC)$_2$, a mixture of 20 mg Co(NO$_3$)$_2$.6H$_2$O and 10 mg H$_2$BBPDC in 1.5 mL dimethylacetamide (DMA) solvent was sealed in a Pyrex glass tube (ID 8 mm/OD 10 mm) and heated to 120 deg. C. at a rate of 1 deg. C. per minute. After holding at 120 deg. C. for 24 hours, it was cooled to 35 deg. C. at a rate of 0.1 deg. C. per minute. The resulting violet crystals were washed with DMA twice to give pure Co$_2$(BBPDC)$_2$ (Co$_2$(H$_2$O)$_2$(BBPDC)$_2$.3DMA (yield=80 percent based on H$_2$BBPDC). The reaction was amplified to gram quantity using multiple tubes. Elemental analysis for Co$_2$(BBPDC)$_2$: calculated: C 57.20 percent, H 6.30 percent, and N 4.17 percent and found: C 58.85 percent, H 6.16 percent, and N 4.15 percent.

TABLE 3

(Crystal Data - Solvated $Co_2(BBPDC)_2$)

| | |
|---|---|
| Empirical formula | $C_{18}H_{18}CoO_5$ |
| Formula weight | 373.25 |
| Crystal system, space group | Trigonal, P-3c1 |
| Crystal size (mm) | 0.18 × 0.15 × 0.10 |
| Unit cell dimensions | a = 18.9328 (1) Å alpha = 90.00° |
| | b = 18.9328 (1) Å beta = 90.00° |
| | c = 22.307 (3) Å gamma = 120.00° |
| Volume | 6924.7 (1) Å$^3$ |
| Z, Calculated density | 12, 1.074 g/cm$^3$ |
| GOF | 1.459 |
| $R_1$, $wR_2$$^b$ | 0.0665, 0.203 |

TABLE 3-continued (Crystal Data - Solvated $Co_2(BBPDC)_2$)

| | |
|---|---|
| M . . . M distance | 2.876 Å |
| M-aqua bonding distance | 1.978 Å |

Gas adsorption studies of activated $Co_2(BBPDC)_2$ are shown in FIGS. 34-38.

To synthesize $Co_2(BBPDC)_2$, a mixture of 20 mg Cu $(NO_3)_2.2.5H_2O$ and 10 mg $H_2BBPDC$ in 1.5 mL dimethylformamide (DMF) solvent with 3 drops $HBF_4$ (50 percent aqueous solution) added was sealed in a Pyrex glass tube (ID 8 mm/OD 10 mm) and heated to 75 deg. C. at a rate of 0.1 deg. C. per minute. After holding at 75 deg. C. for 24 hours, it was cooled to 35 deg. C. at a rate of 0.1 deg. C. per min. The resulting turquoise crystals were washed with DMA twice to give $(Cu_2(H_2O)_2(BBPDC)_2.3DMF$ (yield=80 percent based on $H_2BBPDC$). The reaction was amplified to gram quantity using multiple tubes. Elemental analysis for MAMS-4: calculated: C 55.43 percent, H 5.89 percent, and N 4.31 percent and found: C 55.13 percent, H 5.54 percent, and N 4.58 percent.

TABLE 4

(Crystal Data - Solvated $Cu_2(BBPDC)_2$)

| | |
|---|---|
| Empirical formula | $C_{18}H_{18}CuO_5$ |
| Formula weight | 377.86 |
| Crystal system, space group | Trigonal, P-3c1 |
| Crystal size (mm) | 0.15 × 0.13 × 0.10 |
| Unit cell dimensions | a = 18.4472 (4) Å alpha = 90.00° |
| | b = 18.4472 (4) Å beta = 90.00° |
| | c = 22.5760 (1) Å gamma = 120.00° |
| Volume | 6653.3 (1) Å$^3$ |
| Z, Calculated density | 12, 1.074 g/cm$^3$ |
| GOF | 1.132 |
| $R_1, wR_2^b$ | 0.0731, 0.2152 |
| M . . . M distance | 2.647 Å |
| M-aqua bonding distance | 2.016 Å |

Gas adsorption studies of activated $Cu_2(BBPDC)_2$ are shown in FIGS. 40-44.

Figure 6:
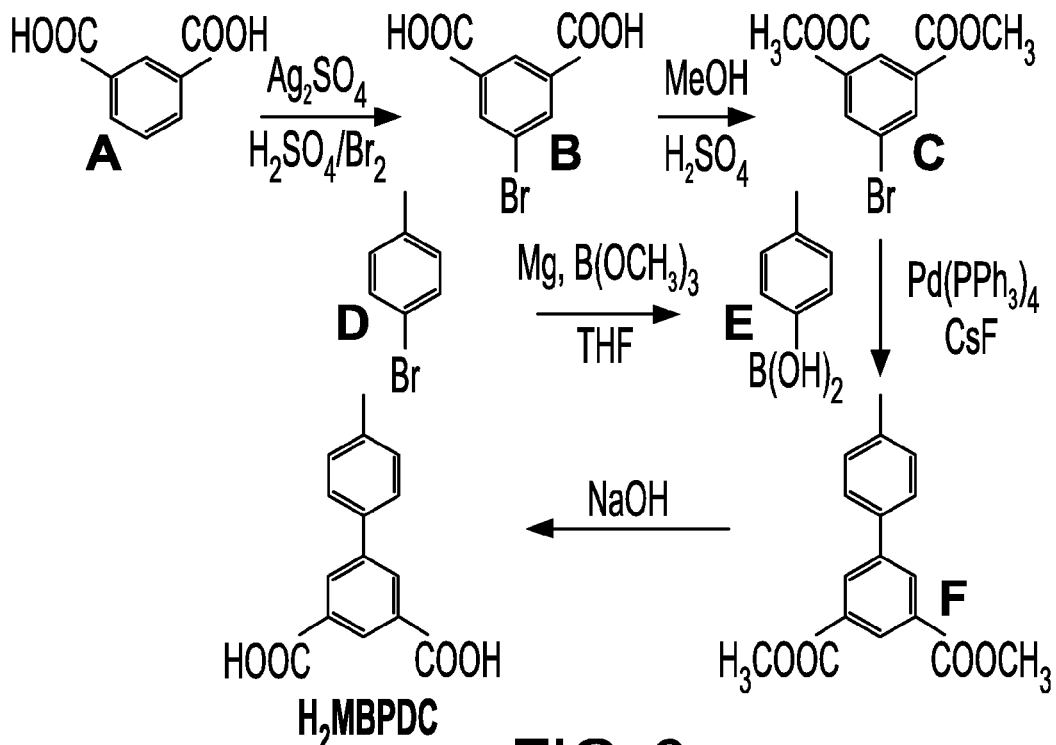
FIG. 6 is a chemical structure drawing rendition of the synthesis of 4'-methyl-biphenyl-3,5-dicarboxylic acid ($H_2$MBPDC).

The 4'-methyl-biphenyl-3,5-dicarboxylic acid ($H_2MBPDC$) precursor for the ligand 4'-methyl-biphenyl-3,5-dicarboxylate (MBPDC) (FIG. 8a) is synthesized as shown in FIG. 6.

Figure 7:
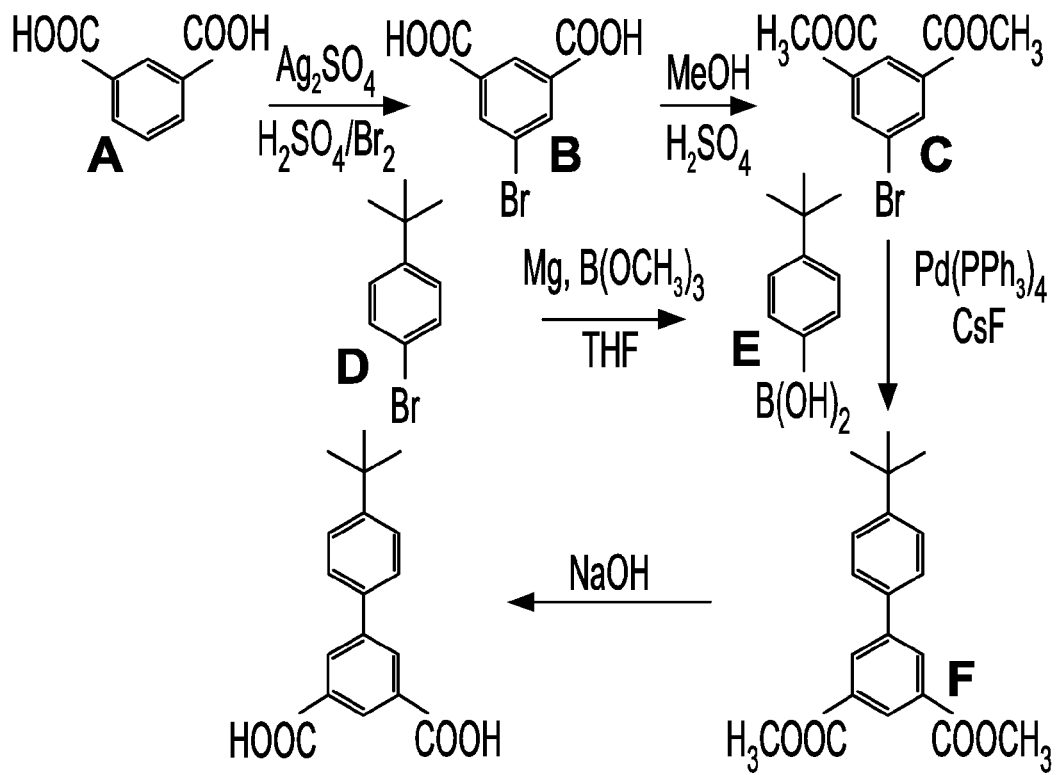
FIG. 7 is a chemical structure drawing rendition of the synthesis of 4'-tert-butyl-biphenyl-3,5-dicarboxylic acid ($H_2$BBPDC).
Figure 8A:
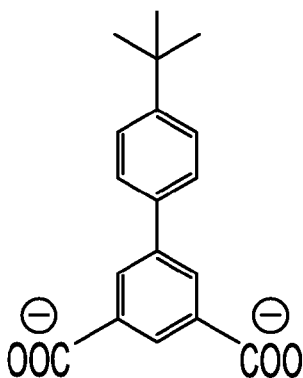
FIGS. 8a-8e are chemical structure drawing renditions of a number of exemplary ligands.
Figure 8A:
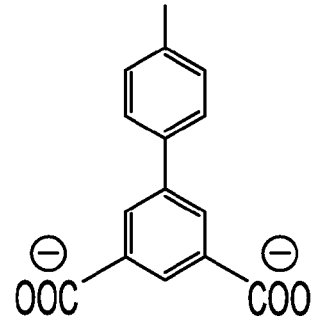
Figure 8A:
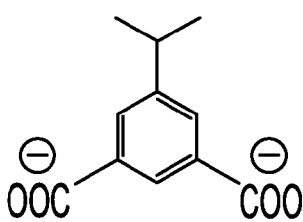
Figure 8A:
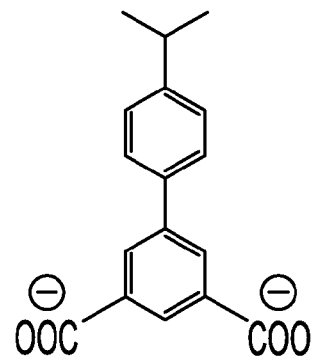
Figure 8A:
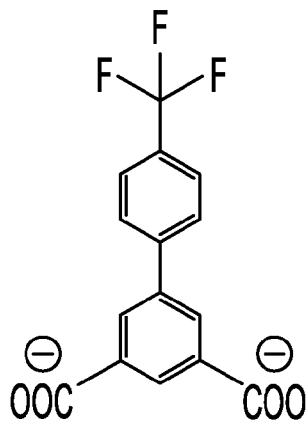
Figure 8B:
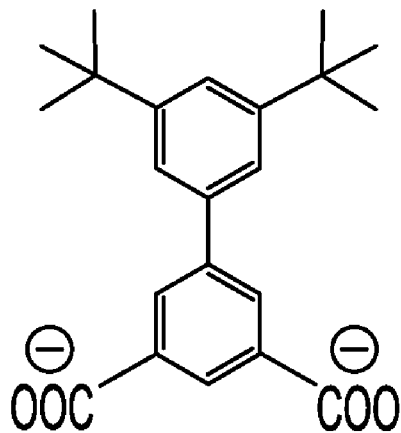
Figure 8B:
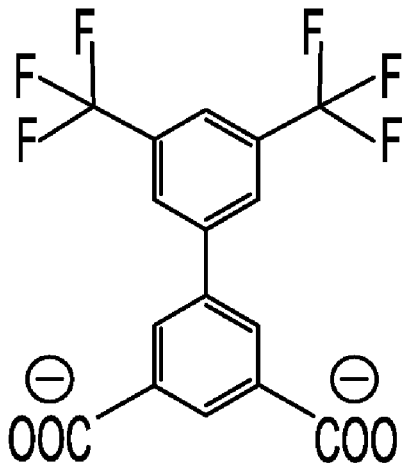
Figure 8C:
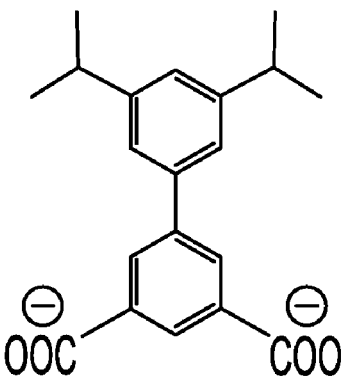
Figure 8C:
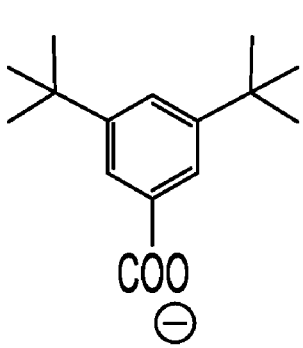
Figure 8C:
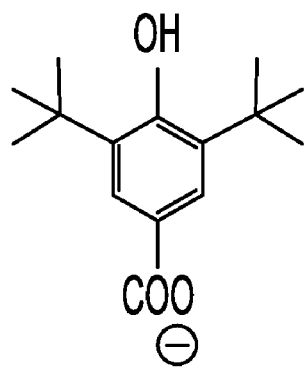
Figure 8C:
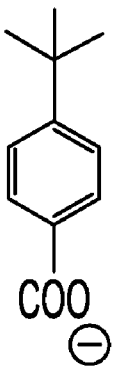
Figure 8C:
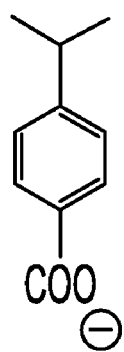
Figure 8D:
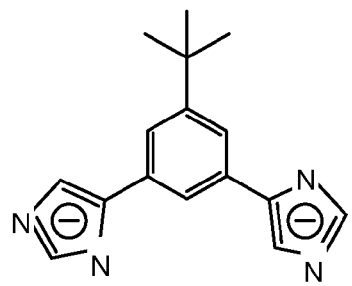
Figure 8D:
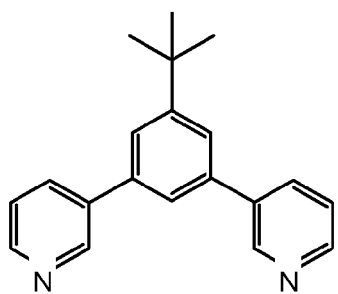
Figure 8D:
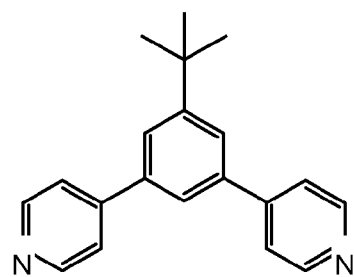
Figure 8D:
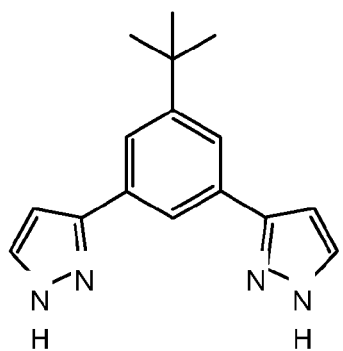
Figure 8D:
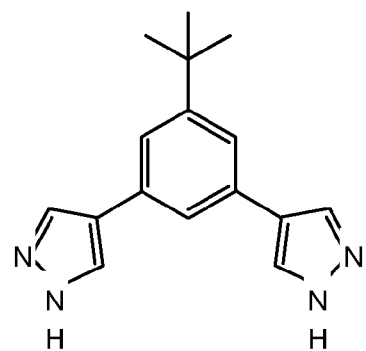
Figure 8E:
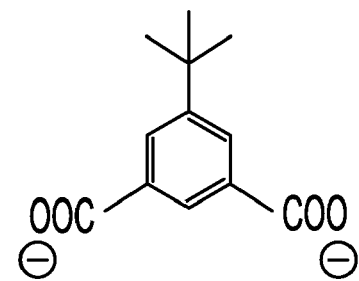
Figure 8E:
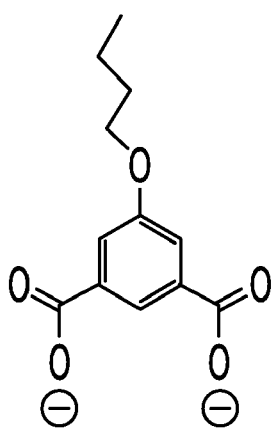
Figure 8E:
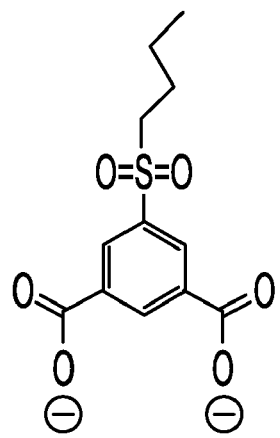
Figure 8E:
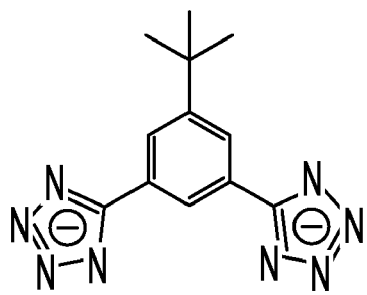

The 4'-tert-butyl-biphenyl-3,5-dicarboxylic acid ($H_2BBPDC$) precursor for the ligand 4'-tert-butyl-biphenyl-3,5-dicarboxylate (BBPDC) (FIG. 8a) is synthesized as shown in FIG. 7 and detailed below.

$H_2BBPDC$ was synthesized as follows: To a 500 mL Schlenk flask, dimethyl-5-bromo-isophtalate (2 g, 0.015 mol), 4-tert-Butyl-phenyl boronic acid (4 g, 0.015 mol), CsF (2.3 g) and $Pd(PPh_3)_4$ (0.2 g) were added. The flask was connected to a Schlenk line while 300 mL 1,2-dimethoxyethane was degassed and added through a cannula. The flask was equipped with a water condenser and refluxed under nitrogen for 48 hours. The solution was dried in a rotary evaporator. Water (100 mL) was added and the solution was extracted with $CHCl_3$. The organic phase was dried with $MgSO_4$. After solvent removal, the crude product was purified by column chromatography (silica, $CHCl_3$) to give the pure product 4'-tert-butyl-biphenyl-3,5-dicarboxylate methyl ester ($^1H$ NMR ($CDCl_3$): 1.4 (s, 9H), 3.9 (s, 3H), 7.3 (d, 2H), 7.5 (d, 2H), 8.4 (s, 2H), 8.6 (s, 1H)). 4'-tert-butyl-biphenyl-3,5-dicarboxylate methyl ester was dissolved in a 100 mL mixture of THF and MeOH (v/v=1:1), to which 20 mL 2N NaOH aqueous solution was added. The mixture was stirred at room temperature overnight. The organic phase was removed. The aqueous phase was acidified with diluted hydrochloric acid to give a white precipitate, which was filtered and washed with water several times to give $H_2BBPDC$ ($^1H$ NMR (DMSO): 1.4 (s, 9H), 7.5 (d, 2H), 7.6 (d, 2H), 8.3 (s, 2H), 8.4 (s, 1H)).

This detailed description in connection with the drawings is intended principally as a description of the present embodiments of the invention, and is not intended to represent the only form in which the present invention may be synthesized, formed, or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. A composition of matter, comprising:
   a plurality of metal clusters;
   a plurality of amphiphilic ligands, each ligand comprising:
      a hydrophobic moiety;
      a first hydrophilic moiety; and
      a second hydrophilic moiety;
   wherein:
      the first hydrophilic moiety bonds to a first metal cluster;
      the second hydrophilic moiety bonds to a second metal cluster;
      the plurality of metal clusters are bonded to a plurality of amphiphilic ligands to form a tri-layer, the tri-layer comprising:
         a first layer of amphiphilic ligands; and
         a second layer of amphiphilic ligands, wherein the plurality of metal clus-' ters are located between, and bonded to, the first amphiphilic ligand layer and the second amphiphilic ligand layer to form a third layer of the tri-layer; and wherein:
      a plurality of tri-layers are held in proximity with each other; and
      the plurality of tri-layers comprise pores having temperature-adjustable pore openings.

2. The composition of matter of claim 1, wherein the pores are hydrophobic pores.

3. The composition of matter of claim 2, wherein:
   the hydrophobic pores having temperature-adjustable pore openings are formed by a plurality of the hydrophobic moieties.

4. The composition of matter of claim 2, wherein a plurality of hydrophobic chambers are formed in the plurality of tri-layers and are molecularly accessible through the hydrophobic pores having temperature-adjustable pore openings.

5. The composition of matter of claim 4, further comprising a plurality of hydrophilic pores in communication with the temperature-adjustable pore openings of the hydrophobic pores.

6. The composition of matter of claim 5, wherein at lest a portion of the hydrophilic pores extending to the boundaries of the composition of matter.

7. The composition of matter of claim 1, wherein the plurality of tri-layers are held in proximity to each other by van der Waals interactions between the hydrophobic moieties of the first amphiphilic ligand layer of a first tri-layer and the second amphiphilic ligand layer of a second tri-layer.

8. The composition of matter of claim 1, wherein the metal clusters comprise metal cations of a metal selected from the group of metals consisting of aluminum, gallium, germanium, the transition metals, including scandium through zinc, yttrium through cadmium, lanthanum through mercury, and actinium, the lanthanides from cerium through lutetium, and the actinides from thorium to the last known element.

9. The composition of matter of claim 1, wherein the amphiphilic ligand is selected from the group consisting of:

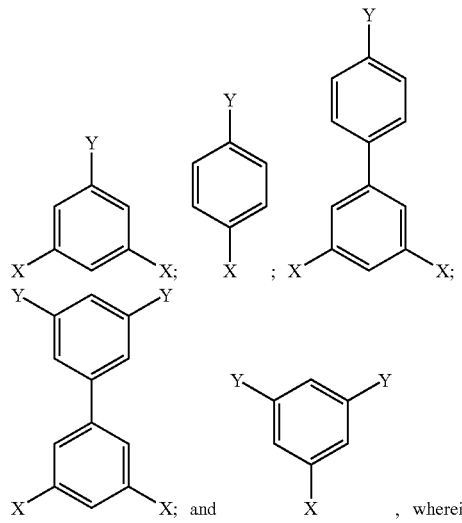

X is at least one of carboxylate, cyano, phosphonate, sulfonate, imidazolate, pyridine, pyrazole, and tetrazolate; and Y is at least one of tert-butyl, methyl, isopropyl, trifluoromethyl, butoxyl, butylsulfonyl, alkyl, halogenated alkyl, alkenyl, alkynyl, and alkoxyl.

10. The composition of matter of claim 9, wherein the amphiphilic ligand is selected from the group of amphiphilic ligands consisting of: 4'-tert-butyl-biphenyl-3,5-dicarboxylate; 4'-methyl-biphenyl-3,5-dicarboxylate; 5-isopropyl-1,3-benzene-dicarboxylate; 4'-isopropyl-biphenyl-3,5-dicarboxylate; 4'-trifluoromethyl-biphenyl-3,5-dicarboxylate; 3',5'-di-tert-butyl-biphenyl-3,5-dicarboxylate; 3,5-di-tert-butyl-benzoate; 3,5-di-tert-butyl-4-hydroxy-benzoate; 4-tert-butyl-benzoate; 4-isopropyl-benzoate; 3',5'-bis-trifluormethyl-biphenyl-3,5-dicarboxylate; 3',5'-diisopropyl-biphenyl-3,5-dicarboxylate; 5-tert-butyl-1,3-benzenediimidazolate; 5-tert-butyl-1,3-benzenedi(3'-pyridine); 5-tert-butyl-1,3-benzenedi(4'-pyridine); 5-tert-butyl-1,3-benzenedi(3'H-3'pyrizole); 5-tert-butyl-1,3-benzenedi(3'H-4'pyrizole); 5-tert-butyl-1,3-benzenedicarboxylate; 5-butoxy-1,3-benzenedicarboxylate; 5-butylsulfonyl-1,3-benzenedicarboxylate; and 5-tert-butyl-1,3-benzeneditetrazolate.

11. A method of synthesizing the 4'-methyl-biphenyl-3,5-dicarboxylate amphiphilic ligand of claim 10 in acid form, comprising the steps of:

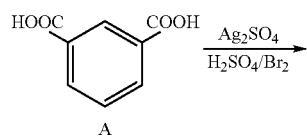

-continued

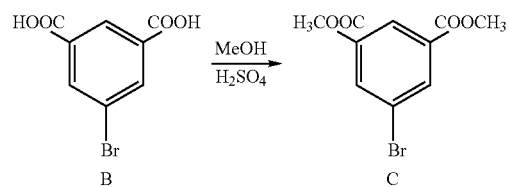

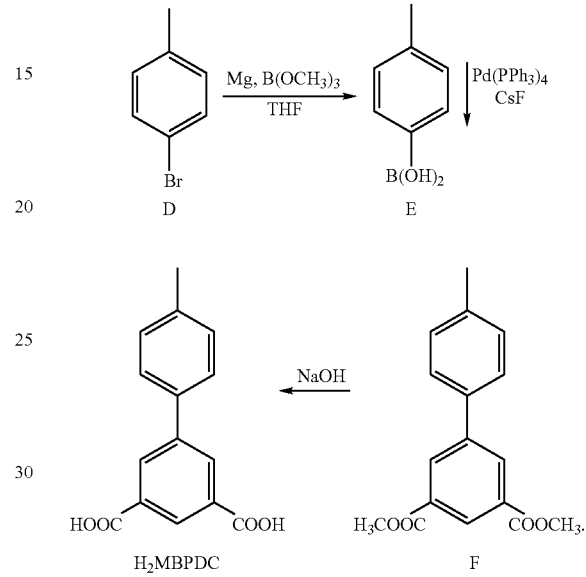

12. A method of synthesizing the 4'-tert-butyl-biphenyl-3,5-dicarboxylate amphiphilic ligand of claim 10 in acid form, comprising the steps of:

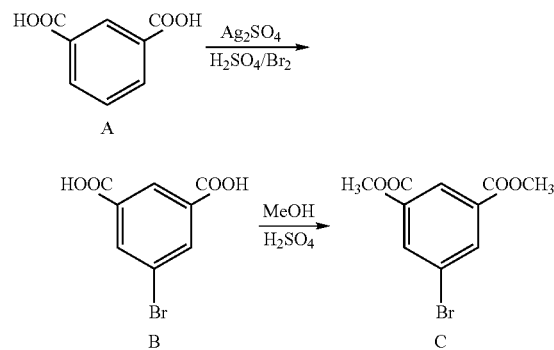

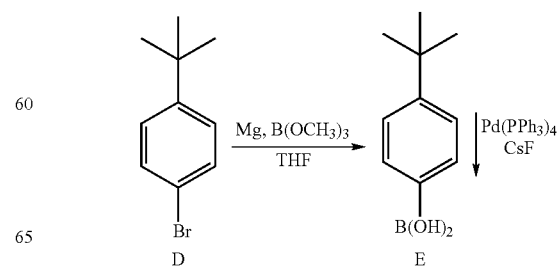

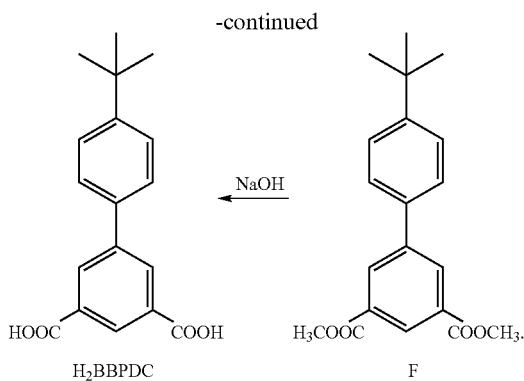

H₂BBPDC           F

13. A method for preparing the composition of matter of claim 1, comprising:

(a) dissolving a metal ion salt of a metal ion, the metal chosen from the list consisting of aluminum, gallium, germanium, the transition metals, including scandium through zinc, yttrium through cadmium, lanthanum through mercury, and actinium, the lanthanides from cerium through lutetium, and the actinides from thorium to the last known element and a source of amphiphilic ligand ions, the amphiphilic ligand ions chosen from the list consisting of:

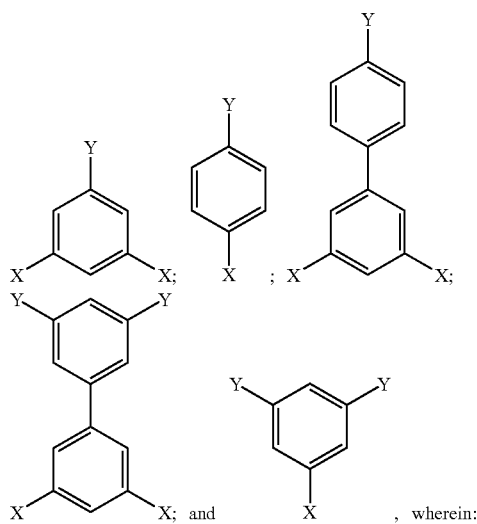

X is at least one of carboxylate, cyano, phosphonate, sulfonate, imidazolate, pyridine, pyrazole, and tetrazolate; and Y is at least one of tert-butyl, methyl, isopropyl, trifluoromethyl, butoxyl, butylsulfonyl, alkyl, halogenated alkyl, alkenyl, alkynyl, and alkoxyl to form a solution;

(b) forming the composition of matter by solvothermal reaction of the solution of metal ions and the amphiphilic ligand ions; and (c) crystallizing the composition of matter from the resultant solution of step (b).

14. The composition of matter of claim 1, wherein the temperature-adjustable pore openings are defined by the equation:

$$D=D_0+\alpha T, \text{ where:}$$

D is the exhibited kinetic opening, in Angstroms, of the temperature-adjustable pore opening;

$D_0$ is the exhibited temperature-adjustable pore opening at 0 deg. K;

$\alpha$ is a constant related to the amphiphilic ligand; and

T is the temperature in degrees Kelvin.

15. A method of using the composition of matter of claim 1, comprising:

(a) maintaining the composition of matter at a preselected temperature to set the size of the temperature-adjustable pore opening;

(b) contacting a gaseous mixture with the composition of matter of claim 1 to selectively adsorb one or more gases with a molecular size smaller than the size of the temperature-adjustable pore opening.

16. The method claim 15, wherein the gaseous mixture comprises a mixture of molecules selected from the group consisting essentially of: $H_2/N_2$, $H_2/CO$, $N_2/O_2$, $N_2/CH_4$, $CH_4/C_2H_4$, and $C_2H_4/C_3H_6$ with the composition of matter of claim 1 to separate the individual molecules from their respective pair.

17. A solvated form of the composition of matter of claim 1 having the molecular formula: $Ni_8(\mu_3\text{-OH})_4(C_{12}H_{12}O_4)_6 (H_2O)_8 \cdot 8H_2O$, wherein $(C_{12}H_{12}O_4)$ is the molecular formula for 5-tert-butyl-1,3-benzenedicarboxylate.

18. A desolvated composition of matter according to claim 17 having the molecular formula: $Ni_8(\mu_3\text{-OH})_4(C_{12}H_{12}O_4)_6$, wherein the temperature-adjustable pore opening is defined by the equation:

$$D=0.0076T+2.76, \text{ where:}$$

D is the exhibited kinetic opening, in Angstroms, of the exhibited temperature-adjustable pore size opening; and T is the temperature in degrees Kelvin.

19. The composition of matter of claim 1, wherein the composition is selected from the group of compositions consisting of the molecular formulas:

$Zn_2(H_2O)_2((CH_3)_3CC_6H_4C_6H_3(CO_2)_2)_2$,
$Co_2(H_2O)_2((CH_3)_3CC_6H_4C_6H_3(CO_2)_2)_2$,
$Cu_2(H_2O)_2((CH_3)_3CC_6H_4C_6H_3(CO_2)_2)_2$, wherein $(CH_3)_3CC_6H_4C_6H_3(CO_2)_2$ is the molecular formula for 4'-tert-butyl-biphenyl-3,5-dicarboxylate.

20. The composition of matter of claim 19, wherein the temperature-adjustable pore openings are defined by the equation:

$$D=0.0073T+2.83, \text{ where:}$$

D is the exhibited kinetic opening, in Angstroms, of the temperature-adjustable pore opening; and T is the temperature in degrees Kelvin.

21. A method of using the composition of matter of claim 19, comprising:

(a) maintaining the composition of matter at a preselected temperature to set the size of the temperature-adjustable pore opening;

(b) contacting a gaseous mixture with the composition of matter of claim 20 to selectively adsorb one or more gases with a molecular size smaller than the size of the temperature-adjustable pore opening.

22. The method claim 21, wherein the gaseous mixture comprises a mixture of molecules selected from the group consisting of: $H_2/N_2$, $H_2/CO$, $N_2/O_2$, $N_2/CH_4$, $CH_4/C_2H_4$, and $C_2H_4/C_3H_6$ with the composition of matter of claim 20 to separate the individual molecules from their respective pair.

23. The composition of matter according to claim 19, wherein the solvated form of the composition is selected from the group of compositions consisting of the molecular formulas:

$Zn_2(H_2O)_2((CH_3)_3CC_6H_4C_6H_3(CO_2)_2)_2 \cdot (HCON(CH_3)_2)$, $Co_2(H_2O)_2((CH_3)_3CC_6H_4C_6H_3(CO_2)_2)_2 \cdot 3(CH_3CON(CH_3)_2)$, and $Cu_2(H_2O)_2((CH_3)_3CC_6H_4C_6H_3(CO_2)_2)_2 \cdot 3(HCON(CH_3)_2)$.

24. A method for preparing the composition of matter of claim 23, comprising:
   (a) dissolving a source of metal ions selected from the group of metals consisting of zinc, cobalt, and copper and a source of 4'-tert-butyl-biphenyl-3,5-dicarboxylate ions in a solvent to form a solution of 4'-tert-butyl-biphenyl-3,5-dicarboxylate ions and ions selected from the group of metals consisting of zinc, cobalt, and copper;
   (b) forming the composition of matter by solvothermal reaction of the 4'-tert-butyl-biphenyl-3,5-dicarboxylate ions and ions selected from the group of metals consisting of zinc, cobalt, and copper; and
   (c) crystallizing the composition of matter from the resultant solution of step (b).

* * * * *